(12) United States Patent
Choi et al.

(10) Patent No.: US 11,998,345 B2
(45) Date of Patent: Jun. 4, 2024

(54) SENSING DEVICE AND METHOD FOR PROCESSING SENSING DATA

(71) Applicant: NEOFECT CO., LTD., Seongnam-si (KR)

(72) Inventors: Young Geun Choi, Yongin-si (KR); Sung Gon Moon, Seoul (KR); Byung Geol Park, Icheon-si (KR); Seo Jeong Han, Seongnam-si (KR); Jin Young Cho, Yongin-si (KR); Keun Hyeok Yoo, Hwaseong-si (KR); Eun Jung Kim, Seoul (KR); Do Kyeong Ha, Seongnam-si (KR); Kyung Hwan Yoo, Seongnam-si (KR)

(73) Assignee: NEOFECT CO., LTD., Seongnam-si (KR)

( * ) Notice: Subject to any disclaimer, the term of this patent is extended or adjusted under 35 U.S.C. 154(b) by 713 days.

(21) Appl. No.: 17/143,713

(22) Filed: Jan. 7, 2021

(65) Prior Publication Data

US 2021/0121120 A1    Apr. 29, 2021

Related U.S. Application Data

(63) Continuation of application No. PCT/KR2020/014145, filed on Oct. 16, 2020.

(30) Foreign Application Priority Data

Oct. 18, 2019    (KR) .......................... 10-2019-0129923
Mar. 30, 2020    (KR) .......................... 10-2020-0037971

(Continued)

(51) Int. Cl.
*A61B 5/00* (2006.01)
*A61B 5/103* (2006.01)

(52) U.S. Cl.
CPC .......... *A61B 5/4023* (2013.01); *A61B 5/1036* (2013.01); *A61B 5/7203* (2013.01);
(Continued)

(58) Field of Classification Search
CPC ................ A61B 5/1036; A61B 5/1038; A61B 5/72–7217; A61B 5/4023;
(Continued)

(56) References Cited

U.S. PATENT DOCUMENTS 5,790,256 A * 8/1998 Brown ................. A61B 5/1036
600/592
6,331,893 B1    12/2001 Brown et al.
(Continued)

FOREIGN PATENT DOCUMENTS

JP    2016-209546 A    12/2016
KR    10-0651639 B1    12/2006
(Continued)

OTHER PUBLICATIONS

Archive.org, Contin Technology, "Pressure Sensor Pad", Jul. 14, 2020. Retrieved from www.contintechd.com/pressure-sensor-pad (Year: 2020).*
(Continued)

*Primary Examiner* — David J. McCrosky
(74) *Attorney, Agent, or Firm* — Studebaker & Brackett PC

(57) ABSTRACT

The present disclosure relates to a sensing device and a method for processing sensing data.

15 Claims, 48 Drawing Sheets

(30) Foreign Application Priority Data

May 12, 2020 (KR) .................. 10-2020-0056463
Sep. 7, 2020 (KR) .................. 10-2020-0113521

(52) U.S. Cl.
CPC .......... *A61B 5/742* (2013.01); *A61B 2505/09* (2013.01); *A61B 2562/0247* (2013.01); *A61B 2562/046* (2013.01); *A61B 2562/164* (2013.01)

(58) Field of Classification Search
CPC ...... A61B 2562/0247; A61B 2562/164; A61B 2562/046
See application file for complete search history.

(56) References Cited

U.S. PATENT DOCUMENTS

| | | | |
|---|---|---|---|
| 2015/0148696 A1* | 5/2015 | Lall | A61B 5/7217 600/510 |
| 2016/0128642 A1 | 5/2016 | Barralon | |
| 2016/0135744 A1 | 5/2016 | Sarrafzadeh et al. | |

FOREIGN PATENT DOCUMENTS

| KR | 10-2013-0122343 A | 11/2013 |
|---|---|---|
| KR | 10-2014-0120181 A | 10/2014 |
| KR | 10-2014-0141052 A | 12/2014 |
| KR | 10-2015-0041903 A | 4/2015 |
| KR | 10-1522905 B1 | 5/2015 |
| KR | 10-2016-0050863 A | 5/2016 |
| KR | 10-2016-0096506 A | 8/2016 |
| KR | 10-2018-0009472 A | 1/2018 |
| KR | 10-2018-0049541 A | 5/2018 |
| KR | 10-2018-0071102 A | 6/2018 |
| KR | 10-2019-0091592 A | 8/2019 |

OTHER PUBLICATIONS

Archive.org, Sensor Products Inc. "Pressure Pad Sensor", Dec. 28, 2018. Retrieved from www.sensorprod.com/glossary/pressure-pad-sensor/pressure-pad-sensor.php (Year: 2018).*
International Search Report issued in PCT/KR2020/014145; dated Jan. 29, 2021.
The extended European search report issued by the European Patent Office dated Apr. 4, 2022, which corresponds to European Application No. 20828936.3-1113 and is related to U.S. Appl. No. 17/143,713.
An Office Action mailed by the Korean Intellectual Property Office dated Jul. 21, 2021, which corresponds to Korean Patent Application No. 10-2020-0037971 and is related to U.S. Appl. No. 17/143,713.
An Office Action mailed by the Korean Intellectual Property Office dated Jul. 29, 2021, which corresponds to Korean Patent Application No. 10-2020-0056463 and is related to U.S. Appl. No. 17/143,713.
An Office Action mailed by the Korean Intellectual Property Office dated Dec. 14, 2021, which corresponds to Korean Patent Application No. 10-2020-0113521 and is related to U.S. Appl. No. 17/143,713.
Sankar Rangarajan et al.; "Design Optimization of Pressure Sensing Floor for Multimodal Human-Computer Interaction"; In: "Human-Computer Interaction"; Oct. 1, 2008; total pp. 30; InTech; XP055293641; ISBN: 978-953-76-1919-0.

* cited by examiner

FIG. 2A
FIG. 2B
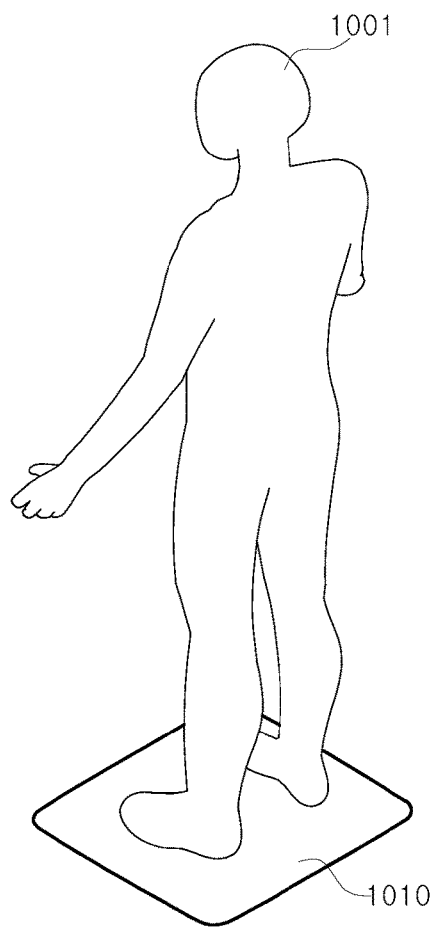
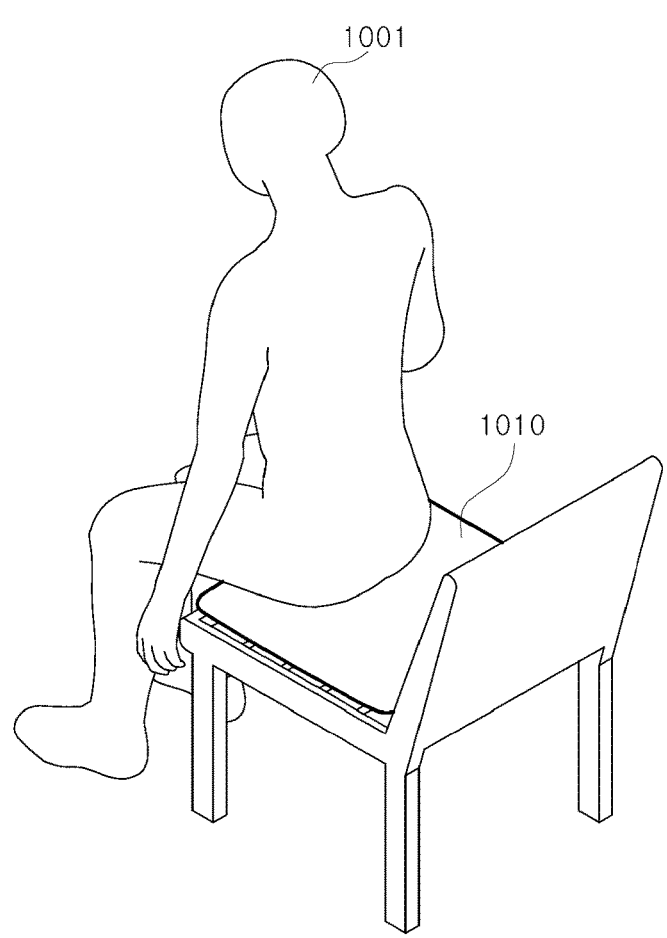

1200

1220

1220

|  | Open | Close |
|---|---|---|
| COP movement length | 323mm | 323mm |
| COP movement area | 534mm$^2$ | 534mm$^2$ |
| Average speed | 4.42mm/s | 4.42mm/s |

SENSING DEVICE AND METHOD FOR PROCESSING SENSING DATA

CROSS-REFERENCE TO RELATED APPLICATIONS

The present application is a continuation of International Patent Application No. PCT/KR2020/014145, filed on Oct. 16, 2020, which is based upon and claims the benefit of priorities to Korean Patent Application Nos. 10-2019-0129923, 10-2020-0037971, 10-2020-0056463 and 10-2020-0113521, filed respectively on Oct. 18, 2019, Mar. 30, 2020, May 12, 2020 and Sep. 7, 2020. The disclosures of the above-listed applications are hereby incorporated by reference herein in their entirety.

BACKGROUND

The present disclosure relates to a sensing device and a method for processing sensing data.

Recently, a sensing device has been used that collects sensing data about a variety of information, such as pressure, acceleration, and tilts, about users, transmits the collected sensing data to a computer, and outputs or analyzes the sensing data in real time.

The sensing device may be used to assess balance keeping ability of the user based on sensing data or enhance the balance keeping ability.

As an example, the sensing device is used as a training device for enhancing balance ability, in the fields of sports, such as baseball and golf, in which it is important to balance both feet and move the center of mass. As another example, the sensing device is used as a training device or a rehabilitation device for raising balance ability for patients with musculoskeletal and nervous system damage or old people with deteriorated balance ability.

As such a sensing device transmits and outputs the collected sensing data to a computer in real time, it is important to provide a current state of the user, such as a left and right balance level, an upper and lower balance level, plantar pressure, or movement of the center of mass, in real time.

Meanwhile, a physical feature may vary for each user. When the sensing device is implemented as sensing physical features of the users of various groups, as a variety of noise are included in sensing data, accurate sensing data may not to be provided to the users. As a result, there is a problem in which reliability of sensing data is degraded.

Furthermore, as the sensing device is implemented in a complicated manner, there is a problem in which it is impossible to carry the sensing device.

SUMMARY

Embodiments of the present disclosure provide a sensing device for sensing physical features of users of various groups and providing a user with accurate sensing data to improve reliability of the sensing data and a method for processing sensing data.

Embodiments of the present disclosure provide a sensing device easily carried.

The technical problems to be solved by the present disclosure are not limited to the aforementioned problems, and any other technical problems not mentioned herein will be clearly understood from the following description by those skilled in the art to which the present disclosure pertains.

According to an embodiment, a sensing device may include a base and a sensing pad that is disposed on the base and measures pressure applied by a user.

Furthermore, the base may include a mounting part detachably equipped with the sensing pad.

Furthermore, the mounting part may include a first groove formed in a shape corresponding to the sensing pad in an upper surface of the base. The sensing pad may be detachably mounted on the first groove.

Furthermore, the mounting part may further include at least one second groove formed to be connected with a partial area of an outer portion of the first groove.

Furthermore, the sensing pad may include a first magnetic body. The base may include a second magnetic body forming gravitation with the first magnetic body and may fix the mounted sensing pad.

Furthermore, the sensing pad may further include a mounting detecting unit that detects whether the sensing pad is mounted on the base.

Furthermore, the sensing pad may further include a controller that receives whether the sensing pad is mounted from the mounting detecting unit and executes a balance training program corresponding to the received result.

Furthermore, the sensing pad may include a first pad that comes into selective contact with the base, a second pad that is provided on an upper portion of the first pad and comes into contact with a body part of the user, and a sensor array that is provided between the first pad and the second pad and measures the pressure applied by the user.

Furthermore, the sensing pad may further include a rigid supporting part disposed between the first pad and the sensor array.

Furthermore, the sensing pad may include a plurality of pressure sensors arranged spaced apart from each other at a certain interval.

Furthermore, the sensing pad may display a reference line for guiding the user to a contact location of a body part of the user on an upper surface.

Furthermore, the reference line may include a plurality of first reference lines which are extended in a transverse direction and are displayed spaced apart from each other at a certain interval in a longitudinal direction.

Furthermore, the reference line may include a plurality of second reference lines which are extended in a longitudinal direction and are displayed spaced apart from each other at a certain interval in a transverse direction.

Furthermore, the sensing device may further include a handrail that is detachably combined with the base and supports at least a portion of a body part of the user.

Furthermore, the sensing device may further include a body sensor that is attached to an upper body of the user and measures a tilt of the upper body of the user.

Furthermore, the sensing pad may include a plurality of sensors that obtain sensing data by the pressure applied by the user. The sensing device may further include a controller that controls the sensing pad and the plurality of sensors. The controller may determine whether an extraction area condition of a first extraction area set in the sensing data is met, may extract data in the first extraction area to generate extraction data, when the extraction area condition of the first extraction area is met, and may set a second extraction area different from the first extraction area, when the extraction area condition of the first extraction area is not met. The plurality of sensors may output sensing values within a specific numerical value range. The sensing data may include number information which is the number of sensors which output sensing values. The first extraction area may be set to have a smaller size than the sensing data. The extraction area condition may be set based on number information about each sensing value included in an extraction area.

Furthermore, the sensing pad may output a sensing value depending on pressure applied to a plurality of pressure sensors arranged at a specific interval on a plane.

Furthermore, the sensing data may further include arrangement location information about an arrangement location of each pressure sensor disposed on the sensing pad.

Furthermore, the extraction area condition may be set based on first number information and second number information. The first number information may be obtained by adding number information about sensing values of first sensing value or less among a plurality of sensing values in the sensing data. The first sensing value may be a sensing value of the smallest numerical value among a plurality of sensing values included in the extraction area. The second number information may be obtained by adding number information about sensing values of second sensing value or more among the plurality of sensing values in the sensing data. The second sensing value may be a sensing value of the largest numerical value among the plurality of sensing values included in the extraction area.

Furthermore, the extraction area condition may be that the first number information and the second number information are less than or equal to a threshold.

Furthermore, the extraction area condition may be that the first number information and the second number information are 0.

Furthermore, the extraction area condition may be that a difference between the smallest sensing value among sensing values, the number information of which is not 0 in the sensing data, and the first sensing value is identical to a difference between the largest sensing value and the second sensing value.

Furthermore, the controller may change sensing values of less than a predetermined valid sensing value among a plurality of sensing values in the sensing data to 0, before determining whether the extraction area condition of the first extraction area is met.

Furthermore, the sensing device may further include a communication unit that transmits the extraction data to a computer. A size of the first extraction area may be set according to a data transfer rate.

Furthermore, the sensing device may further include a storage unit storing extraction area information about an extraction area generating the extraction data for the user. The controller may generate the extraction data based on the extraction area information stored in the storage unit, when sensing data for the user is additionally obtained.

According to an embodiment, a method for processing sensing data in a sensing device including a plurality of sensors may include obtaining sensing data of a user by means of the plurality of sensors configured to output sensing values within a specific numerical value range, determining whether an extraction area condition of a first extraction area set in the sensing data is met, extracting data in the first extraction area to generate extraction data, when the condition is met, and setting a second extraction area, when the condition is not met. The sensing data may include number information which is the number of sensors which output sensing values. The first extraction area may be set to have a smaller size than the sensing data. The extraction area condition may be set based on number information about each sensing value included in an extraction area.

The sensing device may further include a sensing module that includes a plurality of pressure measuring units that is provided on the sensing pad in a matrix and measures plantar pressure by a load of both feet applied to the sensing pad and a control module that determines whether plantar pressure data obtained from the pressure measuring units is noise based on a unique reference value.

Furthermore, the control module may include an alignment unit that aligns the plantar pressure data obtained from the pressure measuring units depending on coordinates of the pressure measuring units to generate a plantar pressure data matrix, an extraction unit that extracts first maximum data having a maximum value in n rows and second maximum data having a maximum value in m columns, on the basis of target data of the n rows and the m columns in the plantar pressure data matrix, a calculation unit that determines one of the first maximum data and the second maximum data as reference data and calculate a unique reference value based on the reference data, and a determination unit that determines whether the target data is noise based on the unique reference value.

Furthermore, the reference data may be a smaller value between the first maximum data and the second maximum data.

Furthermore, the unique reference value may be a value obtained by assigning a weight to the reference data.

Furthermore, the weight may be 0.5 to 0.7.

Furthermore, the sensing device may further include a display device that displays the plantar pressure data matrix, in which filtering of the noise is completed in the control module, on a screen.

According to an embodiment, a method for processing sensing data may include obtaining, by a control module, a plurality of plantar pressure data from a plurality of pressure measuring units provided as a matrix on a sensing pad to which a load of both feet is applied, generating, by the control module, a plantar pressure data matrix obtained by aligning the plantar pressure data depending on coordinates of the pressure measuring units, extracting, by the control module, first maximum data having a maximum value in n rows and second maximum data having a maximum value in m columns, on the basis of target data of the n rows and the m columns in the plantar pressure data matrix, determining, by the control module, one of the first maximum data and the second maximum data as reference data and calculating, by the control module, a unique reference value based on the reference data, and determining, by the control module, whether the target data is noise based on the unique reference value.

Furthermore, the reference data may be a smaller value between the first maximum data and the second maximum data.

Furthermore, the unique reference value may be a value obtained by assigning a weight to the reference data.

Furthermore, the weight may be 0.5 to 0.7.

Furthermore, the determining whether the target data is the noise may include determining, by the control module, the target data as the noise and filtering, by the control module, the noise, when a condition where the target data is less than the unique reference value is met.

Furthermore, the method may further include displaying the plantar pressure data matrix, in which filtering of the noise is completed in the control module, on a screen of a display device.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIGS. 2A and 2B are drawings illustrating an appearance in which a sensing pad is used alone according to the present disclosure;

DETAILED DESCRIPTION

Figure 1:
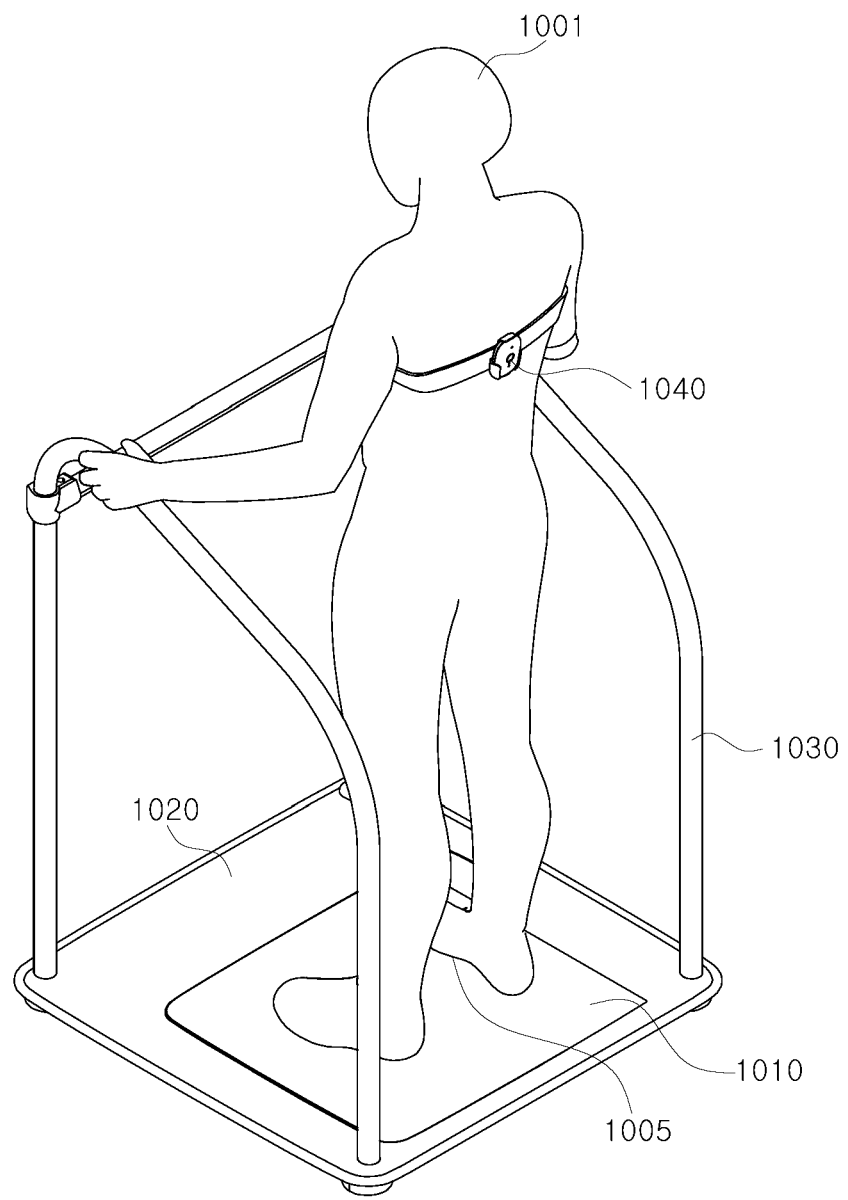
FIG. 1 is a drawing illustrating a sensing device according to the present disclosure.

Advantages, features, and methods of accomplishing the same will become apparent with reference to embodiments described in detail below together with the accompanying drawings. However, the present disclosure is not limited by embodiments disclosed hereinafter, and may be implemented in various forms. Rather, these embodiments are provided to so that this disclosure will be through and complete and will fully convey the concept of the invention to those skilled in the art, and the present disclosure will only be defined by the appended claims.

Terms used in the specification are used to describe embodiments of the present disclosure and are not intended to limit the scope of the present disclosure. In the specification, the terms of a singular form may include plural forms unless otherwise specified. The expressions "comprise" and/or "comprising" used herein indicate existence of one or more other elements other than stated elements but do not exclude presence of additional elements. Like reference numerals designate like elements throughout the specification, and the term "and/or" may include each of stated elements and one or more combinations of the stated elements. The terms such as "first" and "second" are used to describe various elements, but it is obvious that such elements are not restricted to the above terms. The above terms are used only to distinguish one element from the other. Thus, it is obvious that a first element described hereinafter may be a second element within the technical scope of the present disclosure.

Unless otherwise defined herein, all terms (including technical and scientific terms) used in the specification may have the same meaning that is generally understood by a person skilled in the art. Also, terms which are defined in a dictionary and commonly used should be interpreted as not in an idealized or overly formal detect unless expressly so defined.

Spatially relative terms, such as "below", "beneath", "lower", "above", "upper", and the like, may be used herein to describe the relationship of one component to another component as illustrated in the figures. It will be understood that the spatially relative terms are intended to encompass different orientations of components in use or operation, in addition to the orientation depicted in the figures. For example, when the component in the figures is turned over, components described as "below" or "beneath" other components would then be oriented "above" the other components. Thus, the term "below" may encompass both an orientation of above and below. The component may be otherwise oriented, and the spatially relative descriptors used herein may be spatially interpreted according to orientation accordingly.

Hereinafter, an embodiment of the present disclosure will be described in detail with reference to the accompanying drawings.

FIG. 1 is a drawing illustrating a sensing device according to the present disclosure. FIGS. 2A and 2B are drawings illustrating an appearance in which a sensing pad is used alone according to the present disclosure.

Referring to FIG. 1, in the sensing device according to the present disclosure, the sensing device may include a sensing pad 1010 and a base 1020.

The sensing pad 1010 may obtain a balance state of a user.

Referring to FIGS. 1 to 2B, the sensing pad 1010 of the present disclosure may be disposed and used on the base 1020, may be used alone as shown in FIG. 2A, or may be used together with another object (e.g., a chair or the like) as shown in FIG. 2B, according to an embodiment. In other words, the sensing pad 1010 may be detachably formed on the base 1020 to improve portability and may be used to be suitable for various training/assessment situations.

In an embodiment, the sensing pad 1010 may include a plurality of pressure sensors and may measure pressure according to a contact of a specific body part 1005 of the user 1001 to obtain a balance state of the user 1001.

For example, the sensing pad 1010 may measure pressure applied through both feet of the user 1001 as shown in FIGS. 1 and 2A to obtain a balance state of the user 1001, or may measure pressure applied through the hips of the user 1001 as shown in FIG. 2B to obtain a balance state of the user 1001, and the body part 1005 of the user 1001, which comes into contact with the sensing pad 1010, is not limited thereto.

Hereinafter, a description will be given in detail of the sensing pad 1010 according to various embodiments.

Figure 3A:
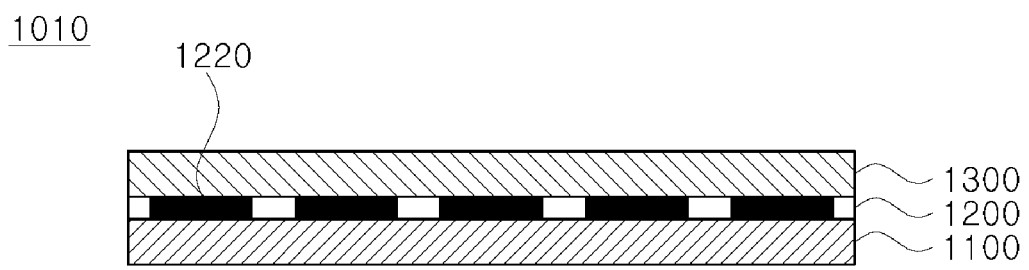
FIGS. 3A and 3B are drawings illustrating a configuration of a sensing pad according to the present disclosure.
Figure 3B:
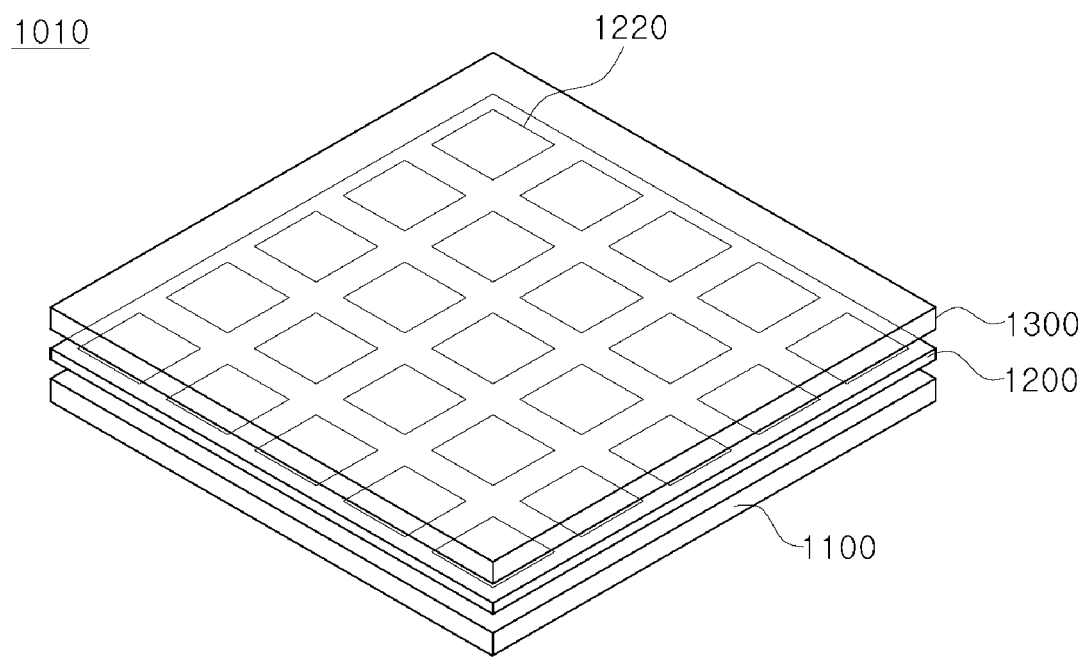

FIGS. 3A and 3B are drawings illustrating a configuration of a sensing pad according to the present disclosure.

Referring to FIGS. 3A and 3B, a sensing pad 1010 according to the present disclosure may include a first pad 1100, a sensor array 1200, and a second pad 1300.

A lower surface of the first pad 1100 may come into contact with a supporting surface (e.g., a base, the ground, or the like).

The second pad 1300 may be provided on an upper portion of the first pad 1100. A specific body part (e.g., feet, hips, or the like) may come into contact with an upper surface of the second pad 1300.

In an embodiment, the first pad 1100 and the second pad 1300 may be formed of a material (e.g., silicon or the like) having elasticity. On the other hand, the first pad 1100 and the second pad 1300 may be formed of a high-stiffness material. A description will be given below of it.

Figure 4:
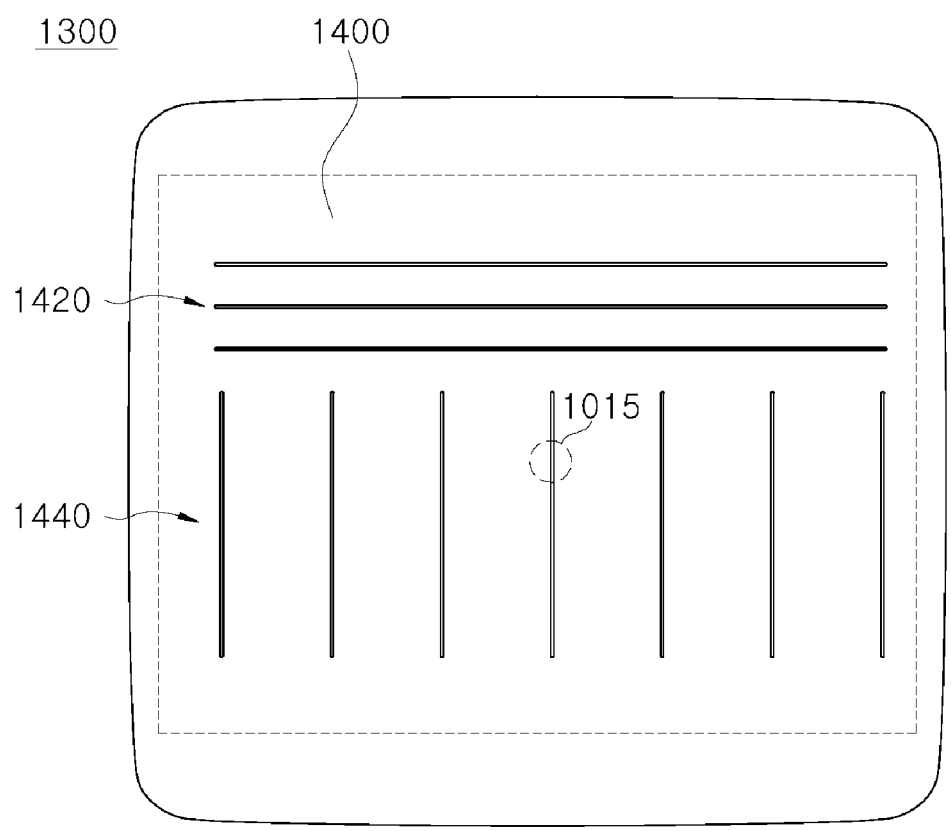
FIG. 4 is a drawing illustrating a reference line of a second pad according to the present disclosure.

FIG. 4 is a drawing illustrating a reference line of a second pad according to the present disclosure.

Referring to FIG. 4, in the present embodiment, a reference line 1400 for guiding a user to a contact location of a specific body part of the user, which is in contact, may be displayed on an upper surface of a second pad 1300.

As a detailed example, the reference line 1400 may be to guide the user such that the center of pressure (COP) of the user is located on a target area 1015. The target area 1015 may be, but is not limited to, a central area of the second pad 1300 as shown in FIG. 4.

For example, for training/assessment of measuring movement of the COP of the user or the like using a sensing pad 1010, the reference line 1400 for placing the COP of the user on an initial location (a target area) may be displayed. A description will be given in detail below of a detailed training/assessment method.

In the present embodiment, the reference line 1400 may include a first reference line 1420 for guiding the user to a front and rear location of the specific body part of the user, which is in contact with the upper surface of the second pad 1300, and a second reference line 1440 for guiding the user to a left and right location.

Figure 5:
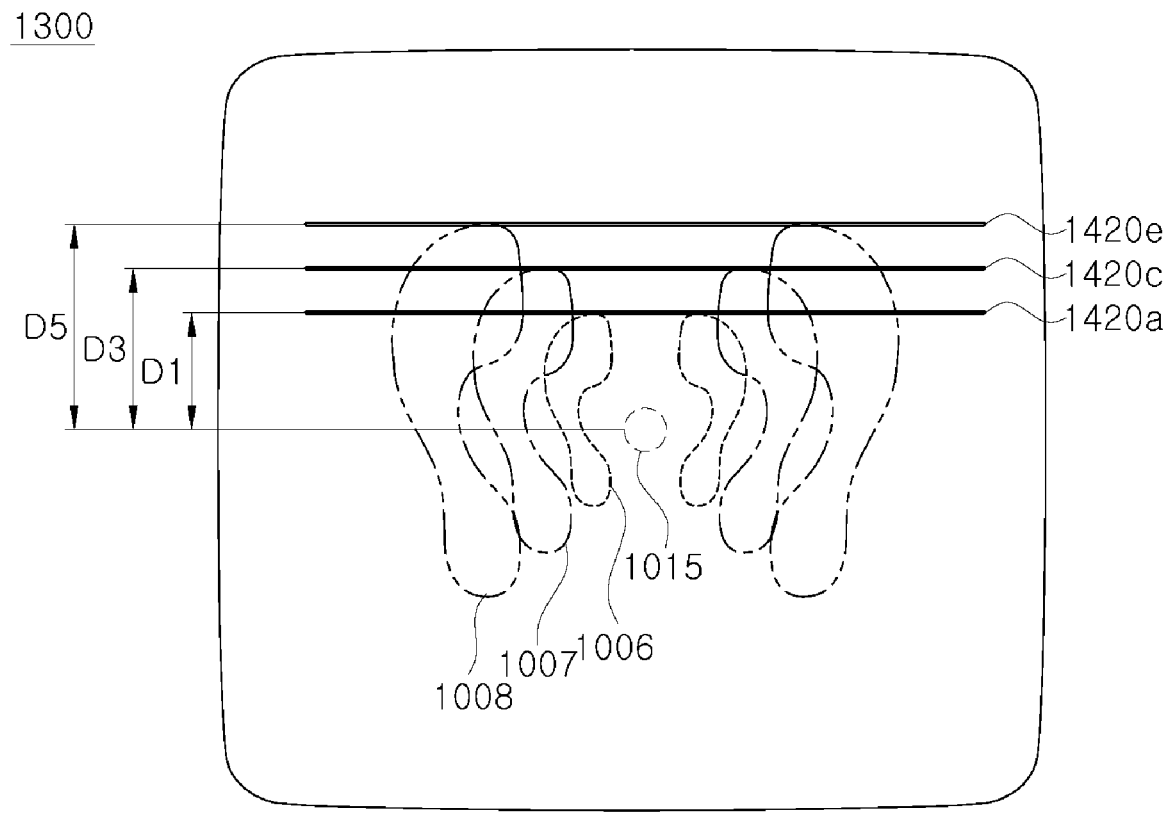
FIGS. 5, 6, and 7 are drawings illustrating a first reference line of a second pad according to the present disclosure.
Figure 5:
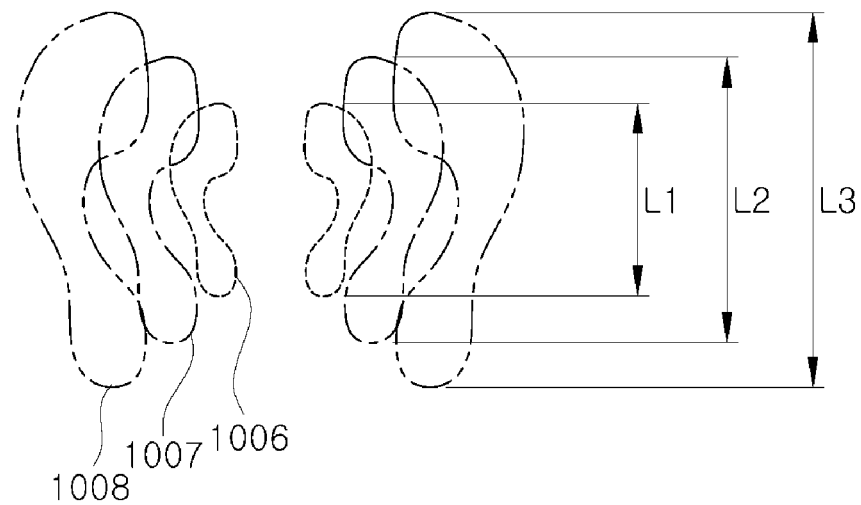
Figure 6:
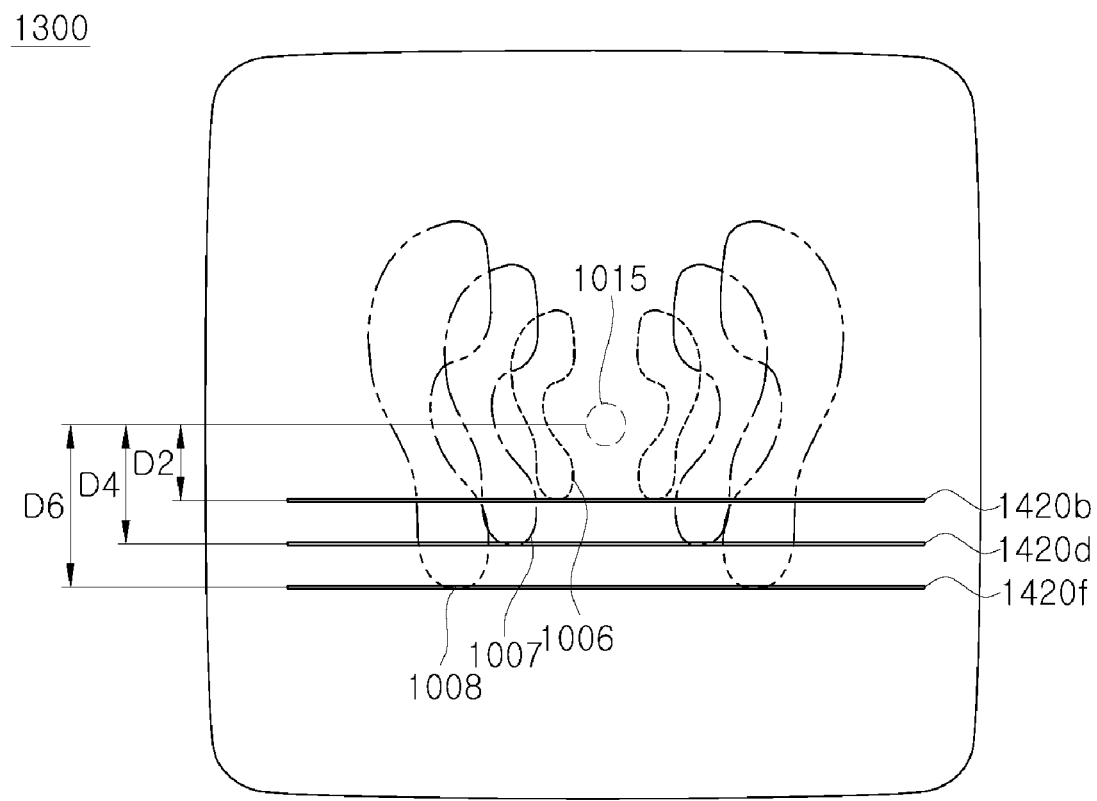
Figure 6:
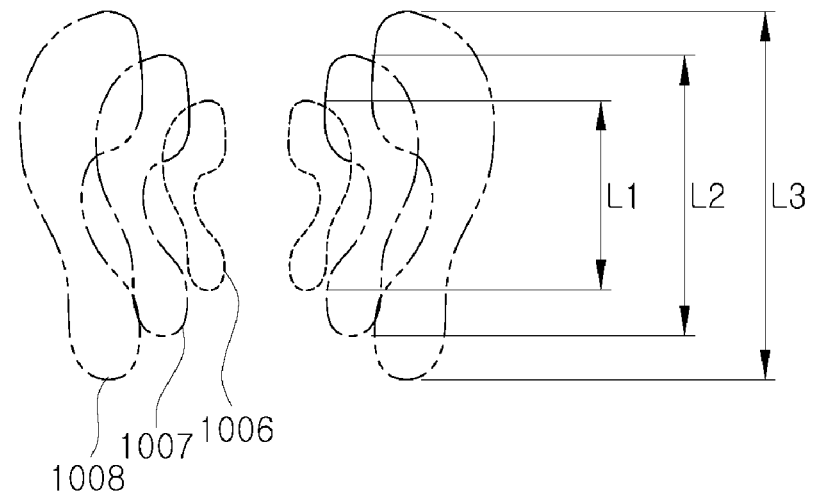
Figure 7:
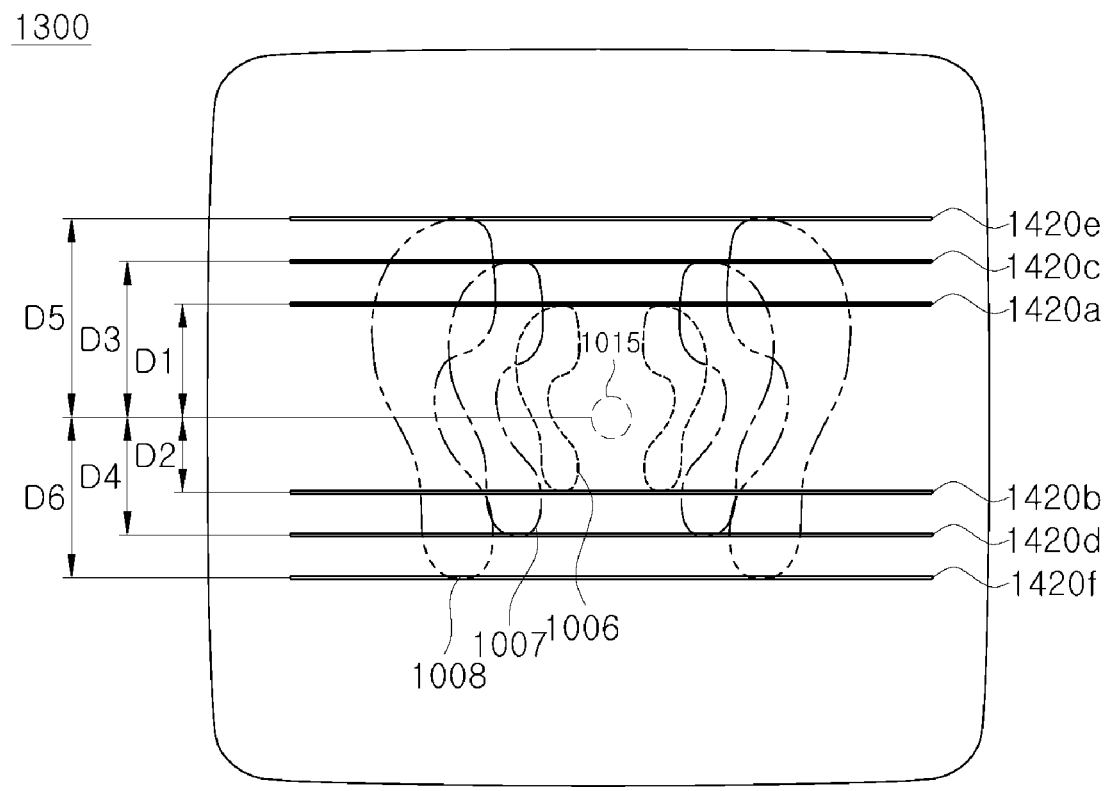
Figure 7:
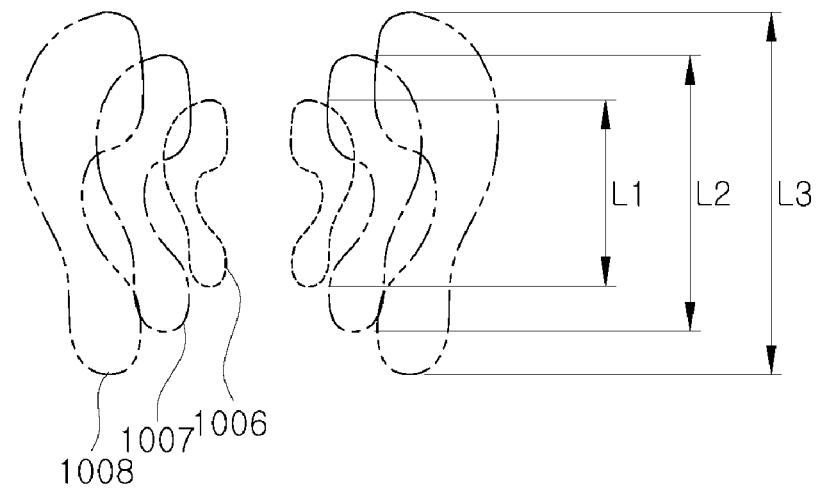

FIGS. 5 to 7 are drawings illustrating a first reference line of a second pad according to the present disclosure.

Hereinafter, an embodiment of the first reference line will be described with an example where both feet of a user come into contact with an upper surface of a second pad 1300 for convenience of description.

Referring to FIGS. 5 to 7, in the present embodiment, a plurality of first reference lines 1420a, 1420b, 1420c, 1420d, 1420e, and 1420f may be displayed extended in a transverse direction and spaced apart from each other at a certain interval in a longitudinal direction. Furthermore, each of the plurality of first reference lines 1420a, 1420b, 1420c, 1420d, 1420e, and 1420f may be to guide the user to a front and rear location of a foot corresponding to a different length.

As a detailed example, the first reference lines 1420a, 1420b, 1420c, 1420d, 1420e, and 1420f for guiding feet of specific lengths may include at least one of first front reference lines 1420a, 1420c, and 1420e on which front ends (toe ends) of feet are located and first rear reference lines 1420b, 1420d, and 1420f on which rear ends (heels) of feet are located.

Referring to FIG. 5, the first front reference lines 1420a, 1420c, and 1420e for respectively guiding feet of different lengths L1, L2, and L3 may be located spaced in a forward direction from a target area 1015 at distances D1, D3, and D5 obtained by multiplying a first reference value by the foot lengths L1, L2, and L3.

Preferably, the first reference value may be 0.6. Because the COP of a normal person is located on average from a toe end to a point of about 60% of a foot length (i.e., a point of about 40% of the foot length from a heel), a front and rear location of the feet may be guided such that a front and rear location of the COP is close to the target area 1015 when the first reference value is 0.6. Furthermore, in this case, when a front and rear location of the target area 1015 is set to a point of about 40% from the bottom side of the second pad 1300, a front and rear location of the feet of the user may be guided to be located on the center of the second pad 1300.

For example, when the first reference value is 0.6 and when a plurality of foot lengths to be guided are 200 mm (L1), 250 mm (L2), and 300 mm, respectively, the first front reference lines 1420a, 1420c, and 1420e may be located spaced in a forward direction from the target area 1015 at 120 mm (D1), 150 mm (D2), and 180 mm (D5). Users respectively corresponding to the foot lengths L1, L2, and L3 may be guided to place their toe ends on the first front reference lines 1420a, 1420c, and 1420e, respectively. In this case, the first front reference lines 1420a, 1420c, and 1420e may be displayed spaced apart from each other in a longitudinal direction at 300 mm.

Referring to FIG. 6, first rear reference lines 1420b, 1420d, and 1420f for respectively guiding feet of different lengths L1, L2, and L3 may be located spaced in a backward direction from the target area 1015 at distances D2, D4, and D6 obtained by multiplying a second reference value by the foot lengths L1, L2, and L3. As described above, preferably, the second reference value may be 0.4.

For example, when the second reference value is 0.4 and when a plurality of foot lengths to be guided are 200 mm (L1), 250 mm (L2), and 300 mm (L3), respectively, the first rear reference lines 1420*b*, 1420*d*, and 1420*f* may be located spaced in a backward direction from the target area 1015 at 80 mm (D2), 100 mm (D4), and 120 mm (D6). The users respectively corresponding to the foot lengths L1, L2, and L3 may be guided to place their heels on the first rear reference lines 1420*b*, 1420*d*, and 1420*f*, respectively. In this case, the first rear reference lines 1420*b*, 1420*d*, and 1420*f* may be displayed spaced apart from each other in a longitudinal direction at 20 mm.

Referring to FIG. 7, in the present embodiment, the first reference line for guiding feet of specific lengths L1, L2, and L3 may include all the first front reference lines 1420*a*, 1420*c*, and 1420*e* and the first rear reference lines 1420*b*, 1420*d*, and 1420*f*. In this case, a distance between the first front reference line and the first rear reference line for guiding the feet of the specific length may be the specific length.

Furthermore, in the present embodiment, although not illustrated in the drawing, the foot lengths L1, L2, and L3 respectively guided by the first reference lines may be further displayed on the upper surface of the second pad 1300. Furthermore, the number of the first reference lines (i.e., the number of foot lengths guided) may be freely made up and thus users of various foot lengths may be simply guided to place their COPs on a target area.

Referring again to FIG. 4, a plurality of second reference lines 1440 for guiding a left and right location of a specific body part of the user may be displayed extended in a longitudinal direction and spaced apart from each other at a certain interval in a transverse direction.

As a detailed example, the plurality of second reference lines may be located spaced apart from each other at both sides at a certain interval with respect to the target area 1015. In this case, side ends of both feet may be guided to be located on a pair of second reference lines symmetric about the target area 1015 to be guided such that left and right locations of the COP are close to the target area 1015.

As the above-mentioned first reference lines 1420 and the above-mentioned second reference lines 1440 are displayed on the upper surface of the second pad 1300, when a variety of training/assessment start, the user may be simply guided such that the COP of the user is located on an initial location (the target area 1015).

A sensor array 1200 may be provided between a first pad 1100 and the second pad 1300.

Figure 8A:
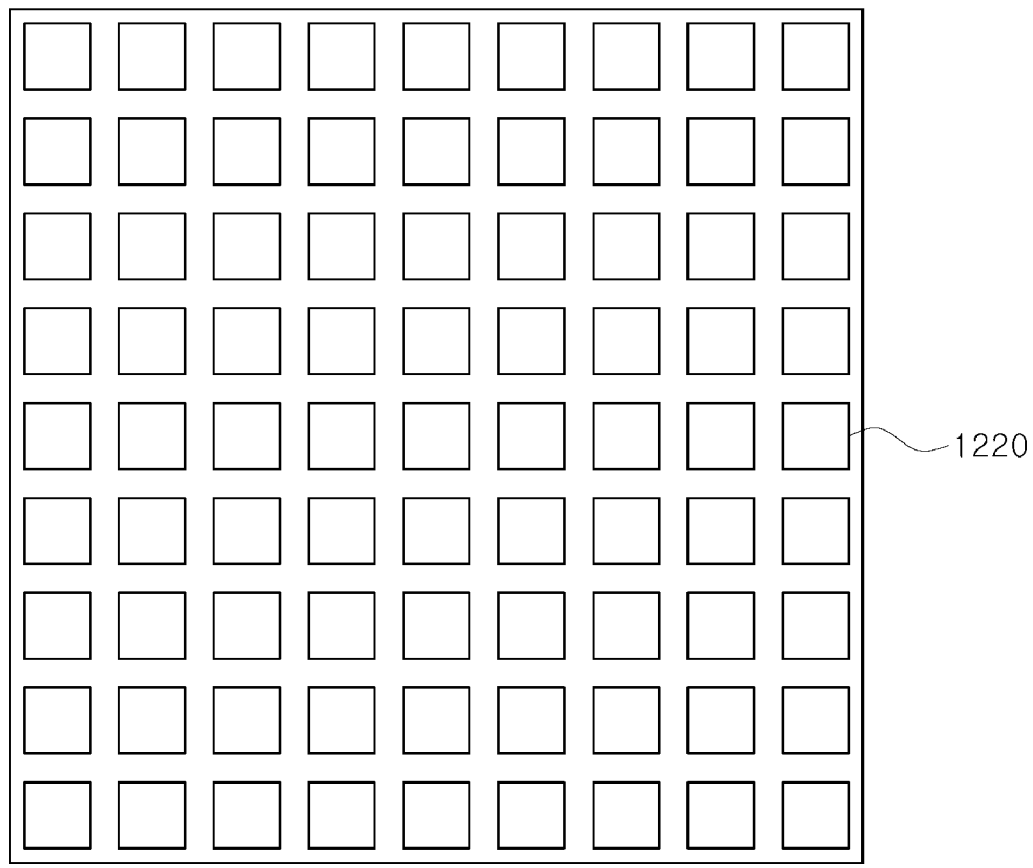
FIGS. 8A and 8B are a plan view and a cross-sectional view of a sensing pad according to the present disclosure.
Figure 8B:

FIGS. 8A and 8B are a plan view and a cross-sectional view of a sensing pad according to the present disclosure.

In the present embodiment, a sensor array 1200 may include a plurality of pressure sensors 1220 arranged at a certain interval on a plane. The plurality of pressure sensors 1220 may sense a load applied to each thereof.

As a detailed example, the plurality of pressure sensors 1220 may be arranged spaced apart from each other at a certain interval to have a plurality of columns and a plurality of rows on the sensor array 1200 as shown in FIG. 8A. On the other hand, as shown in FIG. 8B, the plurality of pressure sensors 1220 may be positioned adjacent to each other such that there are not spaced apart from each other.

Figure 9:
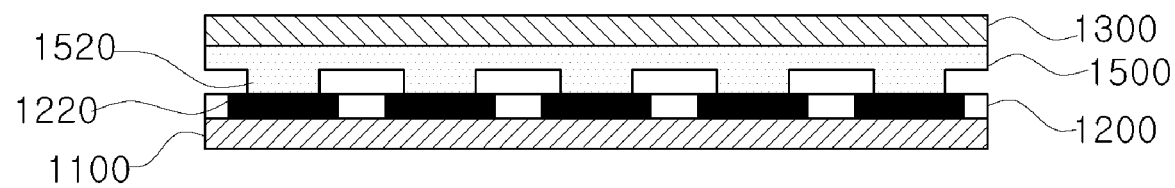
FIGS. 9, 10A, 10B, 10C, 11A, 11B, 12A, and 12B are drawings illustrating a protrusion according to the present disclosure.
Figure 10A:
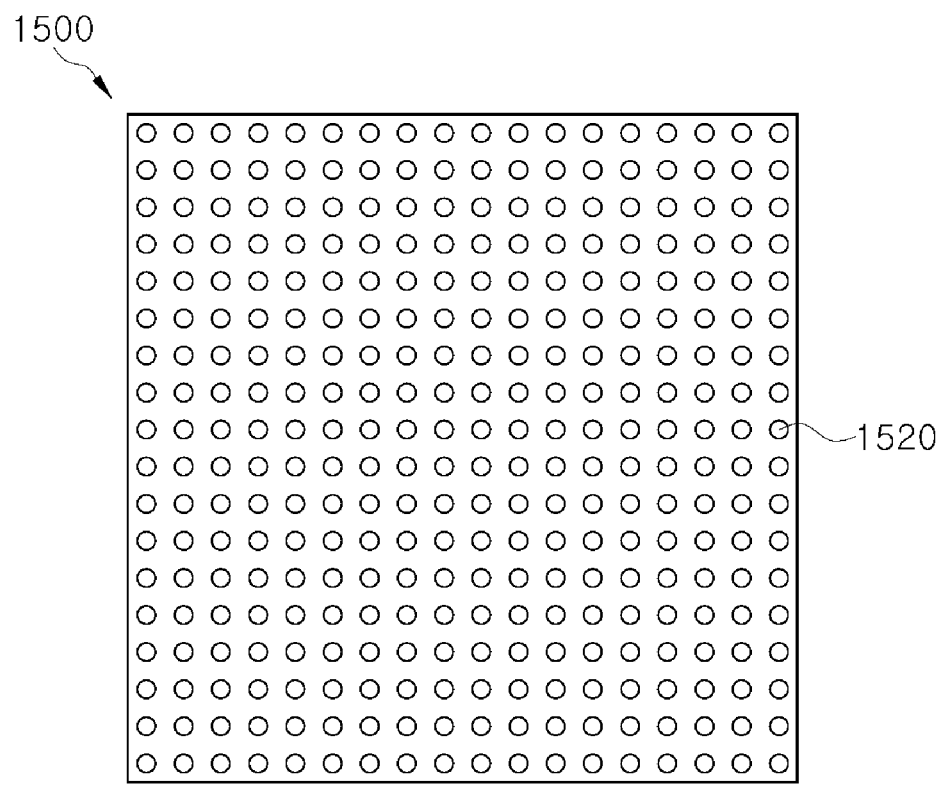
Figure 10B:
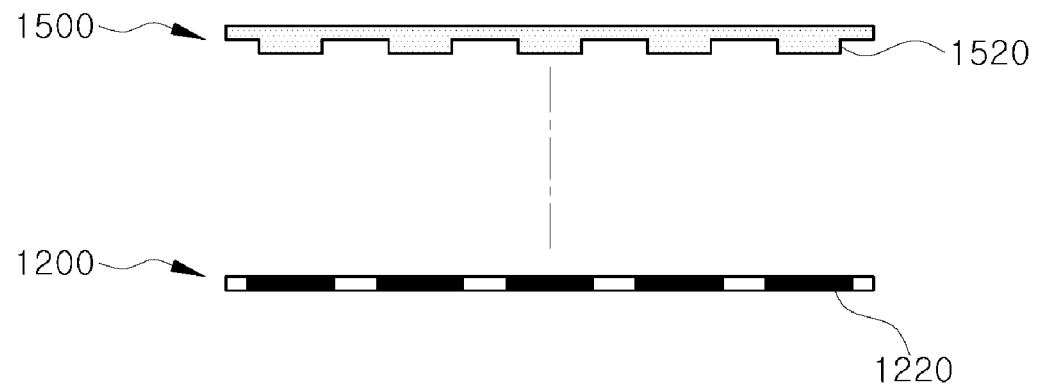
Figure 10C:
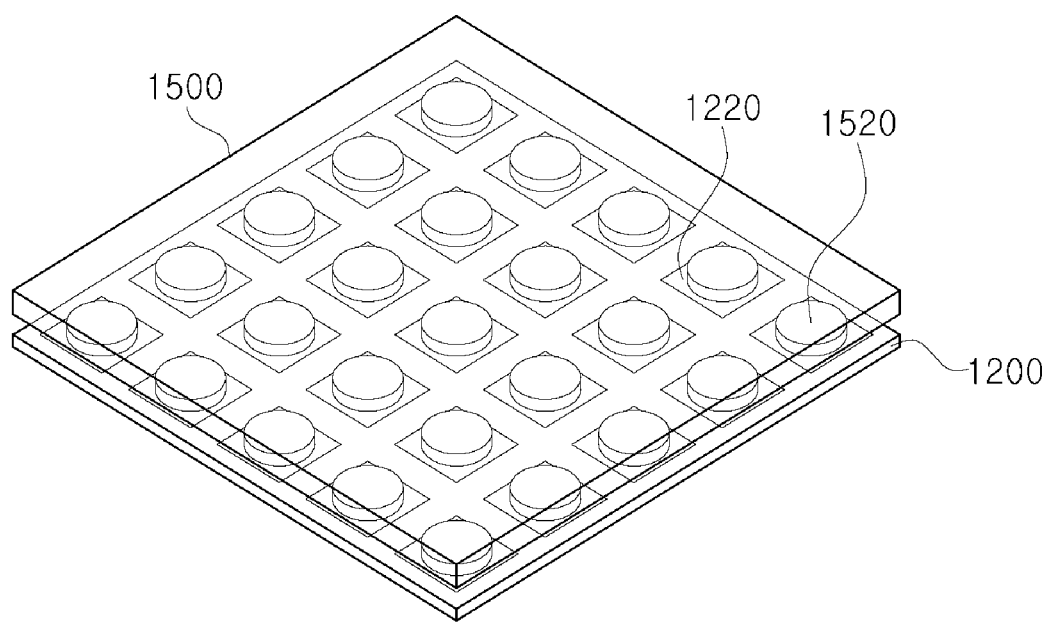

FIG. 9 is a cross-sectional view of a sensing pad further including a protrusion portion according to the present disclosure. FIGS. 10A to 10C are drawings illustrating a configuration of a protrusion portion and a relationship between the protrusion portion and a sensing pad according to the present disclosure.

Referring to FIG. 9, a sensing pad 1010 according to the present disclosure may further include a protrusion portion 1500 provided between a sensor array 1200 and a second pad 1300.

Referring to FIGS. 10A to 10C, in the present embodiment, a plurality of protrusions 1520 may be formed spaced apart from each other at a certain interval to have a plurality of columns and a plurality of rows, on a lower surface of the protrusion portion 1500.

As a detailed example, the plurality of protrusions 1520 may be protruded and formed to correspond one to one to a plurality of pressure sensors 1220 arranged on the sensor array 1200. For example, a cross section of the protrusion 1520 may be formed to be smaller than an area of the pressure sensor 1220, and each protrusion 1520 may be made up to come into contact with the center of the corresponding pressure sensor 1220.

Figure 11A:
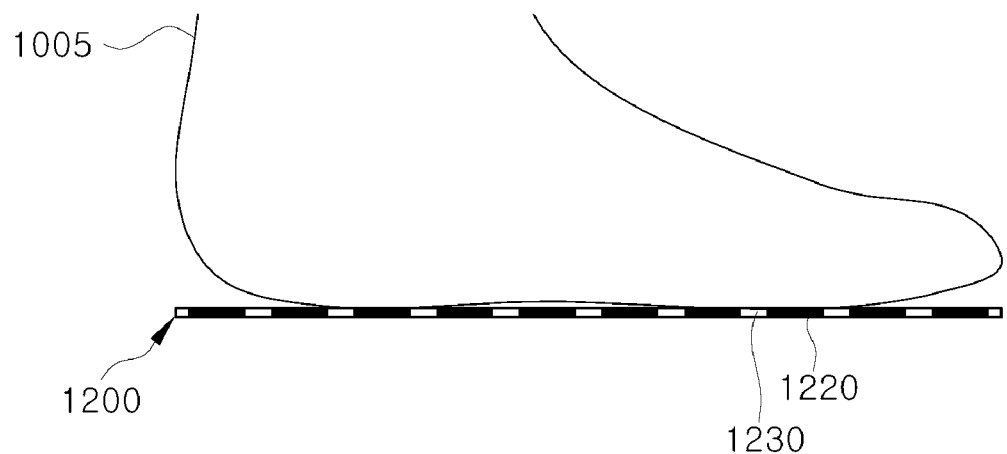
Figure 11B:
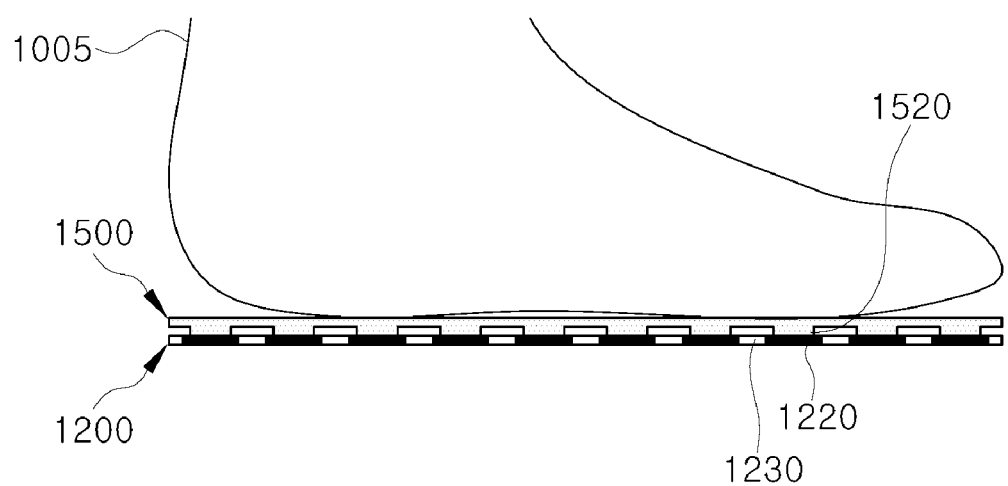
Figure 12A:
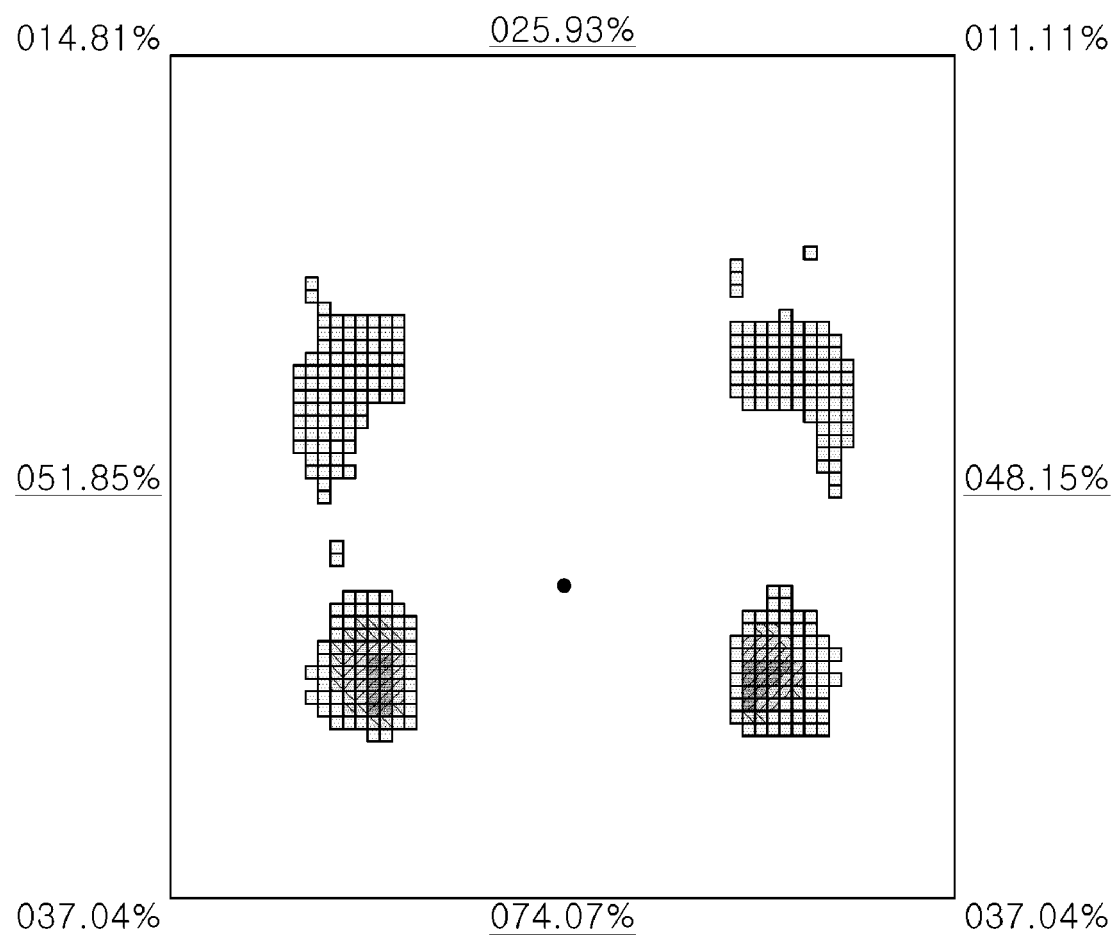
Figure 12B:
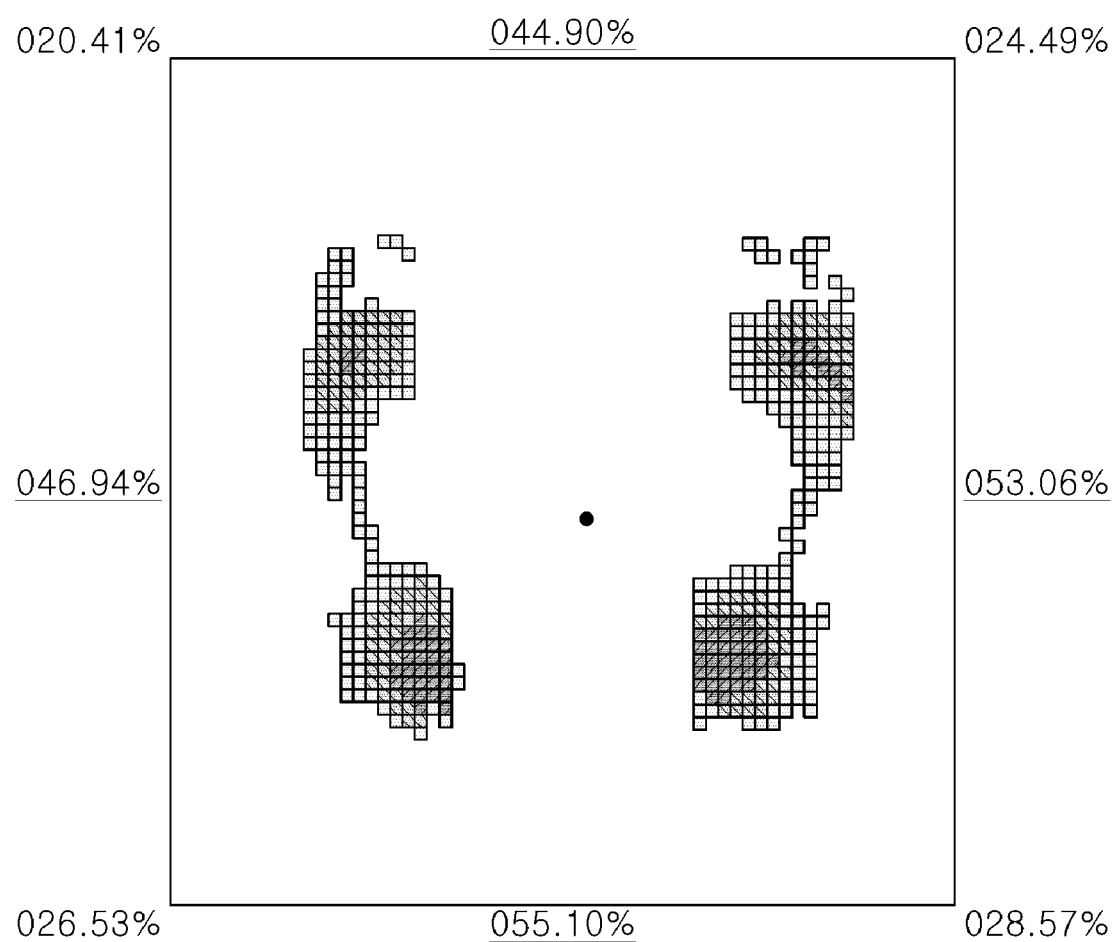

FIGS. 11A and 11B are drawings illustrating an appearance in which a foot of a user comes into contact with a sensing pad according to each of an embodiment in which a protrusion portion is excluded and an embodiment in which a protrusion portion is added (omitting a configuration of a first pad 1100 and a second pad 1300 for convenience of description). FIGS. 12A and 12B are drawings illustrating a result of measuring pressure according to each embodiment.

As shown in FIG. 11A, according to the embodiment in which the protrusion portion is excluded, as a body part 1005 of a user comes into contact with a sensor array 1200, when a load is applied to the sensor array 1200, the applied load may be distributed to an area 1230 in which a pressure sensor is not disposed as well as a plurality of pressure sensors 1220 positioned on the sensor array 1200.

On the other hand, as shown in FIG. 11B, according to the embodiment in which a protrusion portion 1500 is added, as each protrusion 1520 formed on the protrusion portion 1500 delivers a load to each pressure sensor 1220 disposed on the sensor array 1200, a load distributed to the area 1230 in which a pressure sensor is not disposed may be minimized.

In detail, referring to FIGS. 12A and 12B, a measurement value of each pressure sensor 1220 may be indicated lower when the protrusion portion 1500 is excluded (FIG. 12A) than when the protrusion portion 1500 is added (FIG. 12B) due to the distribution of the load. Furthermore, thus, the number of pressure sensors 1220 to which a load of a recognizable range or less is applied may be increased, and, as shown in FIG. 12A, there are the plurality of pressure sensors 1220, each of which does not output a measurement value although a load is actually applied to it. On the other hand, in case of FIG. 12B, as each protrusion 1520 of the protrusion portion 1500 separately delivers a load to each pressure sensor 1220 to minimize distribution of the load, a more accurate measurement value may be obtained than when the protrusion portion 1500 is excluded.

Furthermore, although not illustrated in the drawing, a sensing pad according to the present disclosure may have a plurality of protrusions formed to protrude from a lower surface of a second pad. In detail, the plurality of protrusions may be formed on the lower surface of the second pad to correspond one to one to a plurality of pressure sensors arranged on the sensing pad. That is, in the case, a configuration of a protrusion portion may fail to be separately and additionally provided, and the plurality of protrusions may be formed to protrude from the lower surface of the second pad combined to an upper surface of the sensing pad. Because the relationship between the protrusions and the pressure sensors is described in detail above, a detailed description thereof will be omitted.

Furthermore, although not illustrated in the drawing, the sensing pad according to the present disclosure may further include a rigid supporting part which is provided on a lower portion of the sensing pad and is formed of a rigid material or a variable stiffness material. That is, the sensing pad may further include the rigid supporting part formed of a high stiffness material (e.g., a rigid rubber or the like) if necessary to improve stability of the pressure sensor or improve the sense of use of the user.

Furthermore, in another embodiment, the sensing pad may fail to separately and additionally have the configuration of the rigid supporting part, and the first pad 1100 and the second pad 1300 may be formed of a rigid material or a variable stiffness material.

Although not illustrated in the drawing, a sensing pad 1010 according to the present disclosure may include at least one of a power supply unit, a communication unit, an output unit, a mounting detecting unit, and a controller.

The power supply unit may supply power to each component of the sensing pad 1010. In an embodiment, the power supply unit may be a wired power connection configuration (e.g., a USB type) capable of connecting an external power source to the sensing pad 1010. In another embodiment, the power supply unit may be a configuration (e.g., a battery) detachable from the sensing pad 1010. In another embodiment, the power supply unit may be a configuration capable of performing charging using a charger adapter.

In an embodiment, the communication unit may be connected with a computer or a body sensor module 1040 described below in a wired or wireless manner. For example, the communication unit may communicate with the computer or the body sensor module 1040 using, but not limited to, Bluetooth® communication, Bluetooth® low energy (BLE) communication, near field communication, WLAN (Wi-Fi) communication, Zigbee communication, infrared data association (IrDA) communication, Wi-Fi direct (WFD) communication, ultra wideband (UWB) communication, ANT+ communication, or a WIFI communication method.

In an embodiment, the output unit may output a power state, a charging state, or a connection state of the sensing pad 1010. Alternatively, the output unit may output a balance training program or a balance training result.

The mounting detecting unit may detect a training situation of the sensing pad 1010. In detail, the mounting detecting unit may detect an environment where a user uses the sensing pad 1010. For example, the mounting detecting unit may detect whether the sensing pad 1010 is mounted on a base 1020, whether the sensing pad 1010 is placed on the ground, whether the sensing pad 1010 is used together with another object (e.g., a chair or the like), or the like.

A detailed method where the mounting detecting unit detects the training situation of the sensing pad 1010 is not limited thereto. For example, when one or more magnets are included in the base 1020, the mounting detecting unit may include a hall sensor to detect whether the sensing pad 1010 is mounted on the base 1020. For another example, the mounting detecting unit may detect a height of the sensing pad for the ground to detect a training situation of the sensing pad 1010.

The controller may receive a training mode and may execute a training program corresponding to the received training mode or may calculate a training result. According to an embodiment, the controller may be provided in the sensing pad 1010 or may be located outside the sensing pad 1010 like an application installed in a mobile terminal of the user.

In an embodiment, the controller may receive a training mode from the user, may execute a training program corresponding to the received training mode, and may output a training program screen on an output unit of the sensing pad 1010 or an external display device.

In another embodiment, the controller may receive a training situation from the mounting detecting unit, may execute a balance training program corresponding to the received training situation, and may output a training program screen on the output unit of the sensing pad 1010 or the external display device. That is, when a training program corresponding to each training situation (an environment where the user uses the sensing pad) is previously stored and when a specific training situation is received from the mounting detecting unit, a corresponding training program may be automatically executed without a separate setting or input or a selection screen of an executable training program may be output. For example, the controller may automatically execute a training program with which the feet of the user come into contact, when a state where the sensing pad is mounted on the base is received, and may automatically execute a training program with which the hips of the user come into contact, when a state where the sensing pad is disposed on a chair is received.

Figure 13:
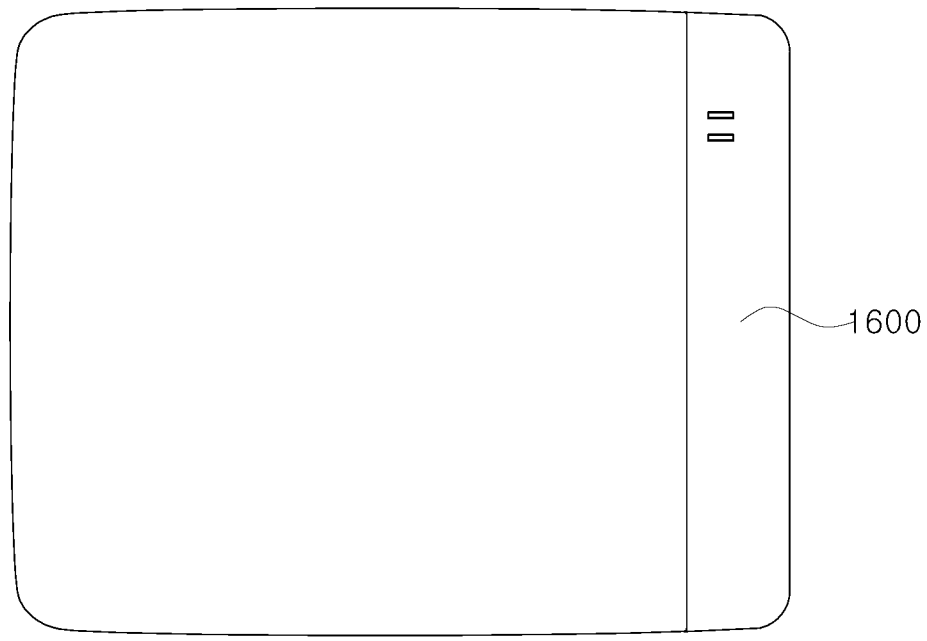
FIG. 13 is a plan view of a sensing pad further including an electronic module according to the present disclosure.

FIG. 13 is a plan view of a sensing pad further including an electronic module according to the present disclosure.

Referring to FIG. 13, an electronic module 1600 may be provided at one side or both sides of a sensing pad 1010 according to the present disclosure. The electronic module 1600 may include at least one of the power supply unit, the communication unit, the output unit, the mounting detecting unit, and the controller, which are described above.

In the present embodiment, when the electronic module 1600 is provided at one side of the sensing pad 1010, there is an effect where a user may distinguish between the front and the rear and between the left and the right with respect to a location where the electronic module 1600 is disposed. Furthermore, although the electronic module 1600 is provided at only one side, because the user may hold the electronic module 1600 to move upon carrying it, there is a simple feature in carrying it.

Furthermore, when the electronic module 1600 is provide at both sides of the sensing pad 1010, when the sensing pad 1010 is formed of a flexible material, and when magnets with different polarities are included in both ends of the sensing pad 1010, as the user folds the sensing pad 1010 to fix it using the magnets positioned at both the ends, there is a feature where the user may conveniently carry the sensing pad 1010.

In the present embodiment, the sensing pad 1010 may include one or more magnets, and the one or more magnets may play a role in fixing the sensing pad 1010 when the sensing pad 1010 is disposed on a base 1020. Furthermore, the sensing pad 1010 may be configured to include magnets with different polarities at its one side and the other side such that the one side and the other side of the sensing pad 1010 are attachable to each other.

Referring again to FIG. 1, the base 1020 and a handrail 1030 are indicated in the form of being attached to each other, but the handrail 1030 is detachable from the base 1020. Thus, the handrail 1030 may be used by being assembled only when need for use, and only the base 1020 may be used.

The base 1020 may be supported on the ground, which may include a mounting part on which the sensing pad 1010 is mounted.

Figure 14A:
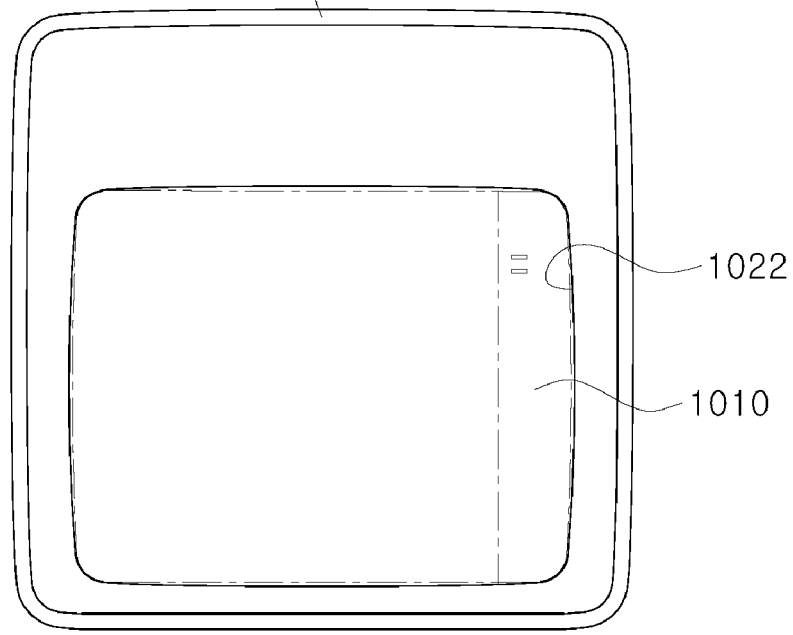
FIGS. 14A, 14B, and 14C are drawings illustrating a mounting part of a base according to the present disclosure.
Figure 14B:
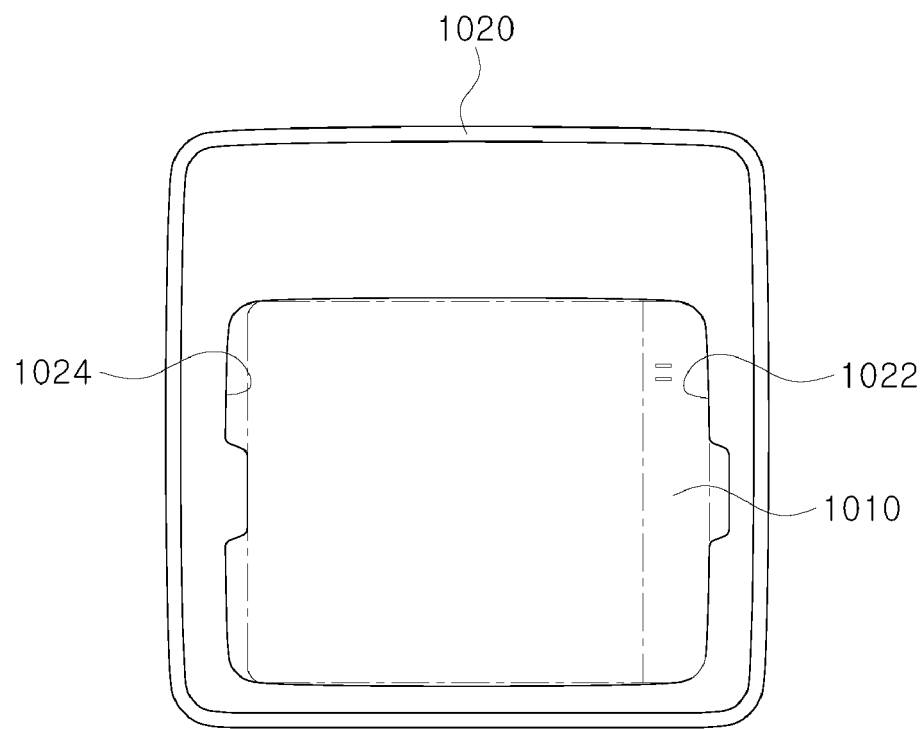
Figure 14C:
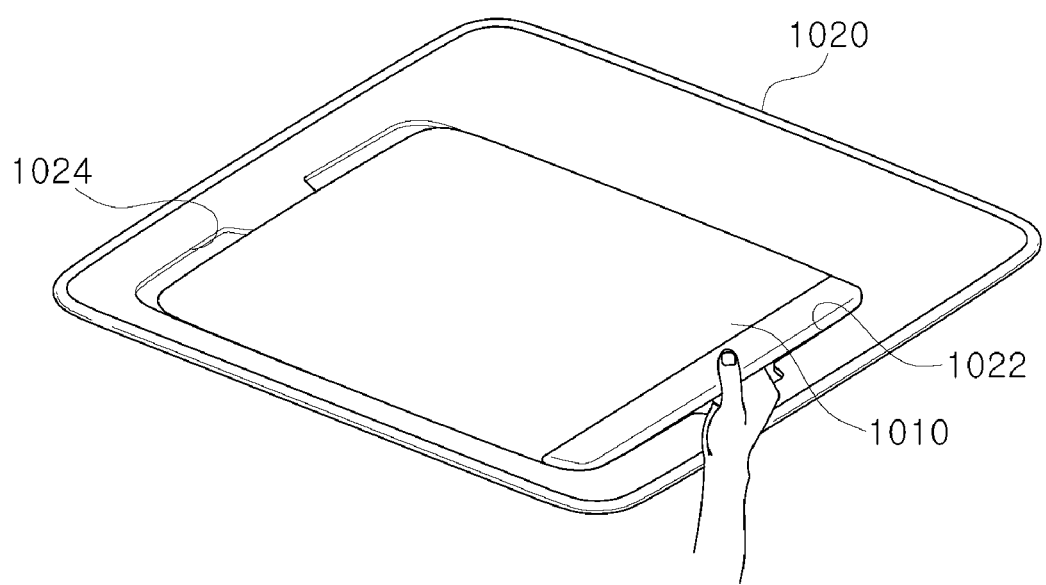

FIGS. 14A to 14C are drawings illustrating a mounting part of a base according to the present disclosure.

Referring to FIG. 14A, in the present embodiment, to fix a sensing pad 1010 disposed on a base 1020, the mounting part may include a first groove 1022 formed in a shape corresponding to the sensing pad 1010 in an upper surface of the base 1020. That is, in this case, the sensing pad 1010 may be detachably mounted on the first groove 1022.

Referring to FIGS. 14B and 14C, in the present embodiment, the mounting part may further include at least one second groove 1024 formed to be connected with a partial region of an outer portion of the first groove 1022. That is, the second groove 1024 may play a role in assisting a user to easily demount the sensing pad 1010 mounted on the first groove 1022. Because FIGS. 14B and 14C are only an example of the second groove 1024, the second groove 1024 may be formed to vary in shape and number in the range of not limiting the fixing of the sensing pad 1010, and depths of the first groove 1022 and the second groove 1024 may be the same as or differ from each other.

In the present embodiment, the sensing pad 1010 and the base 1020 may be configured to include magnetic bodies with different polarities, thus fixing the sensing pad 1010 disposed on the base 1020. That is, the base 1020 may be configured to, when the sensing pad 1010 includes a first magnetic body, include a second magnetic body forming gravitation with the first magnetic body.

As described above, the handrail 1030 is detachable from the base 1020, which is composed in a prefabricated manner. The handrail 1030 may play a role such that the user may hold on and stand up in sit to stand training described below and may also play a role in supporting a body part of the user in standing assessment or training on the sensing pad 1010.

Referring again to FIG. 1, the sensing device according to the present disclosure may further include a body sensor module 1040.

Figure 15:
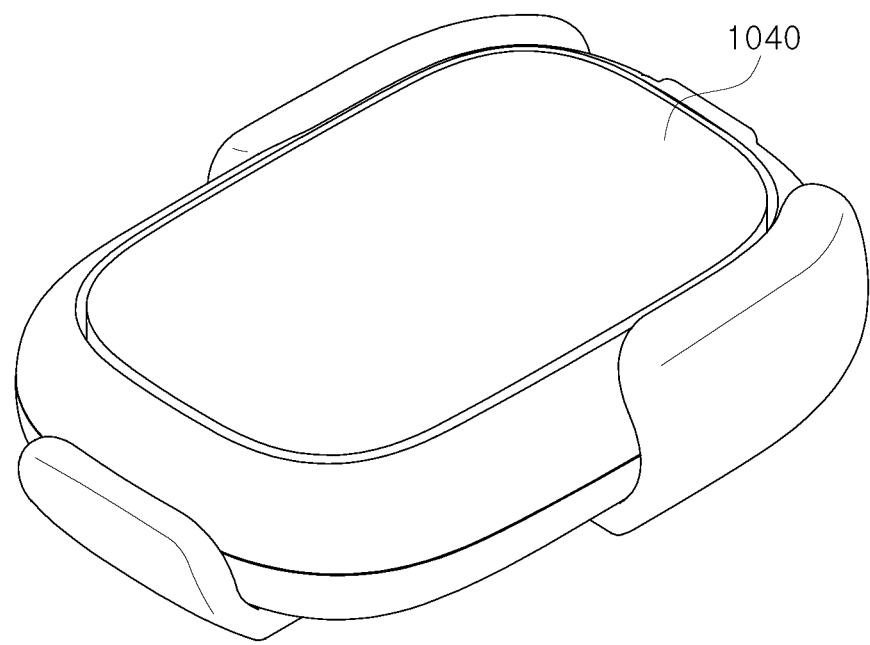
FIG. 15 is a drawing illustrating a body sensor module according to the present disclosure.

FIG. 15 is a drawing illustrating a body sensor module according to the present disclosure.

Referring to FIG. 15, a body sensor module 1040 may include all of sensors capable of measuring a tilt. Particularly, an inertial measurement unit (IMU) sensor may be included as a sensor which measures a tilt.

In the present embodiment, a tilt of the upper body of a user may be measured using the body sensor module 1040, and the reason why it is measured is because it is difficult to determine whether the user is measured in his or her correct posture using only measured pressure measurement data upon balance assessment or balance training of the user.

As the user tilts his or her upper body as an incorrect posture to obtain pressure measurement data required in assessment or training, upon balance assessment or balance training, a pressure of a titled side on the sensing pad 1010 may be measured to be higher. In such a case, when balance assessment or balance training of the user is performed using only the sensing pad 1010, although the user is in an incorrect posture, the result may be derived as being correct.

Thus, the body sensor module 1040 may be used together to determine whether the user adds pressure using a tilt of his or her upper body or the like, upon balance assessment or balance training.

In the present embodiment, the body sensor module 1040 may be disposed between the fifth spine and the seventh spine. In detail, this is because the tilt of the upper part of the user is derived as 0 when the body sensor module 1040 is disposed in the location between the fifth spine and the seventh spine. However, the location where the body sensor module 1040 is disposed is not limited to the example, and the body sensor module 1040 may be disposed in a location where the tilt of the upper body of the user becomes 0 or a location which the tilt becomes a criterion rather than 0.

In the present embodiment, the body sensor module 1040 may include only one body sensor. In another embodiment, the body sensor module 1040 may include a plurality of body sensors.

When the plurality of body sensors are included in the body sensor module 1040, they may be arranged spaced apart from each other over a certain distance to determine whether the user is in a bent posture, upon balance assessment or balance training for the user.

Because a computer determines whether the user stands correctly in an accurate posture using a tilt value of the body sensor module 1040, the result that the posture of the user is a correct posture may be derived, when the posture of the user is bent, but when the user stands such that a portion where the body sensor module 1040 is disposed becomes 0 in tilt, when using only one sensor. Accordingly, as an incorrect result is derived although the posture of the user is incorrect, the user may continue proceeding with training or assessment in the incorrect posture. Thus, for the plurality of sensors in the body sensor module 1040 to accurately measure a tilt of the body of the user, the plurality of sensors may be arranged spaced apart from each other at a certain distance in the body sensor module 1040.

In the present embodiment, as one sensor is included in the body sensor module 1040 and as a band worn on the body of the user is formed widely, the plurality of body sensor module 1040 spaced apart from each other over a certain distance on the band may be included.

In the present embodiment, as one sensor is included in the body sensor module 1040 and as a band and the body sensor module 1040, which are worn on the body of the user, are plural in number, the band including the one body sensor module 1040 may be plural in number to be attached to the user. Furthermore, in such a case, when the bands are divided and attached to the upper body and the lower body, there is an effect where it is easy to determine whether the user perfectly sits or perfectly stands in the 'sit to stand' training described below.

In the present embodiment, the body sensor module 1040 may be connected with a communication unit of the sensing pad 1010 in a wired or wireless manner to transmit a tilt sensor data value obtained by the body sensor module 1040 to the sensing pad 1010. Alternatively, on the other hand, a pressure sensor data value obtained by the sensing pad 1010 may be transmitted to the body sensor module 1040.

Receiving the tilt sensor data value from the body sensor module 1040, the sensing pad 1010 may collect the tilt sensor data value and the pressure sensor data value and may transmit the collected value to the computer.

The tilt sensor data value and the pressure sensor data value transmitted to the computer may be transmitted as raw data itself and may be transmitted in the formed of processed data.

In the present embodiment, for power supply to the body sensor module 1040, a wired power connection configuration may be included to connect an external power source like the above-mentioned power supply of the sensing pad 1010. At this time, the wired power connection configuration may be a USB type. In another embodiment, a removable internal power source may be included in the body sensor module 1040 itself. In another embodiment, the body sensor module 1040 may be charged and used using a charger adapter.

The body sensor module 1040 may be a sensor which measures a tilt of the upper body of the user, which may be formed to be detachably attached to the user. In a manner detachably attached to the user, in an embodiment, a band worn on the body may be used. The band may be formed to be attachable or detachable by the user, and the body sensor module 1040 disposed on the band may also be composed to be detachable from the band.

The band may include a pocket form to insert the body sensor module 1040 therein. Alternatively, the band may be composed to detachably attach the body sensor module 1040 to the band itself.

In the present embodiment, the body sensor module 1040 may include an output unit (e.g., an LED or the like) for displaying a state of a power source and may indicate a charging state or a connection state.

For example, although not illustrated separately, a sensing device according to the present disclosure may further include a computer. The computer may receive sensor values measured from the plurality of pressure sensors in the sensing pad 1010 or the body sensor module 1040, and may calculate the COP using pressure values measured from the plurality of pressure sensors to determine a balance level of the user or may compare a tilt measured from the body sensor module 1040 with a tilt value which becomes a criterion to determine the balance level of the user.

The result of the balance level determined by the computer may be reflected in content stored in a memory to be displayed. Furthermore, the computer may guide the user to maintain his or her balance on a variety of content described below to proceed with training for developing balance ability.

Furthermore, although not illustrated separately, the sensing device according to the present disclosure may further include a display device for providing balance assessment and balance training. The display device may be moved.

Figure 16A:
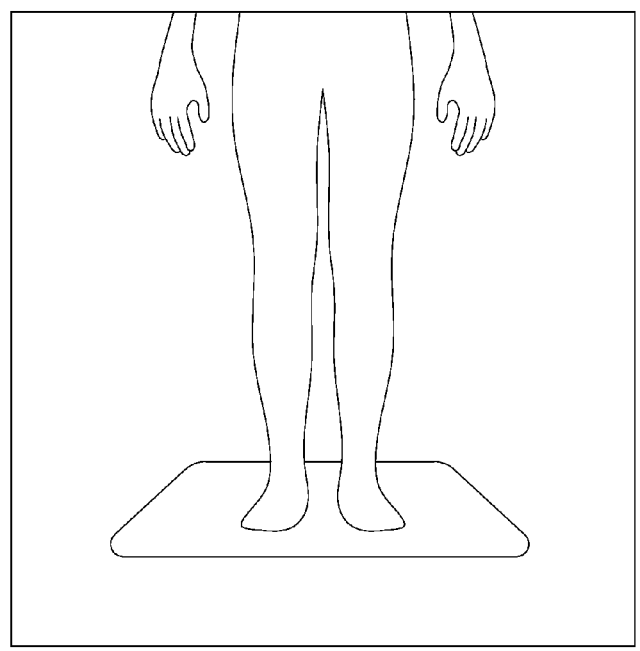
FIGS. 16A, 16B, and 16C are drawings illustrating a manner which performs static assessment according to the present disclosure.
Figure 16B:
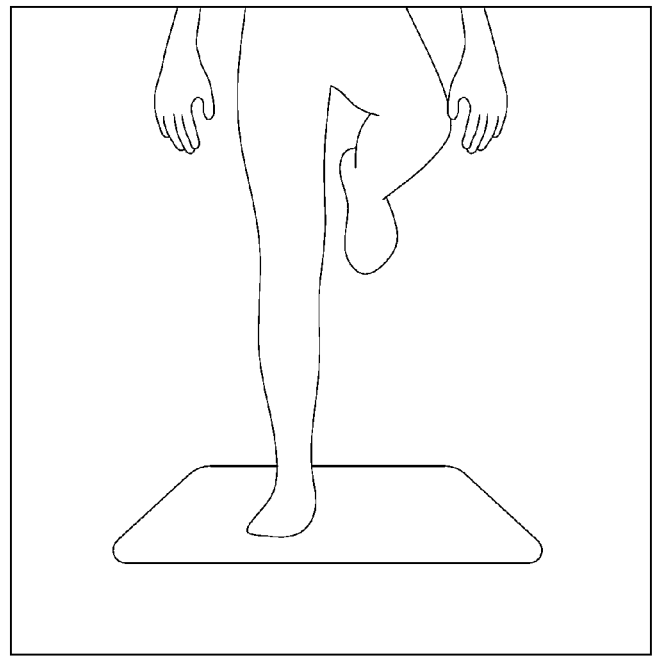
Figure 16C:
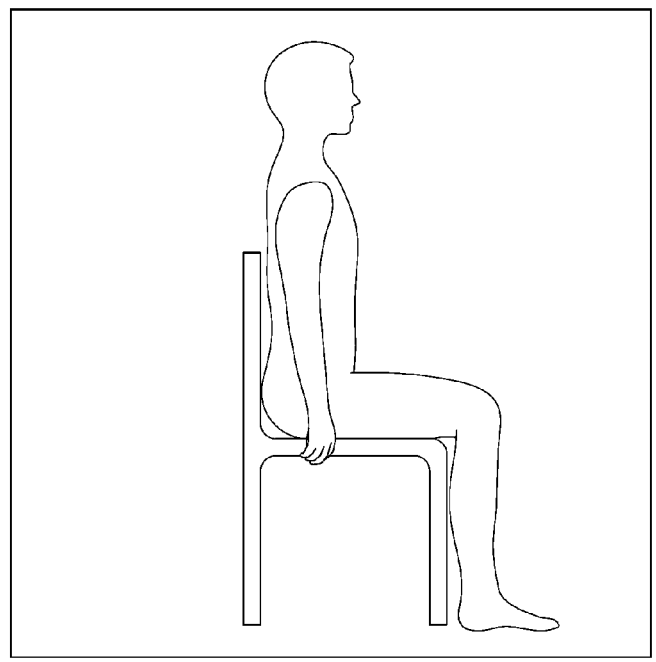

FIGS. 16A to 16C are drawings illustrating a manner which performs static assessment according to the present disclosure. FIGS. 17A to 18B are drawings illustrating a manner which performs dynamic assessment according to the present disclosure. FIGS. 19A and 19B are drawings illustrating a manner which performs pressure assessment according to the present disclosure.

FIG. 16A is assessment for a state standing still, which is assessment using eyes. A body sensor module 1040 may be used together, and the number of times of measurement and a measurement time may be set. A movement distance of the COP, a movement length image of the COP, a movement area of the COP, or an average speed of the COP may be derived as the result of the assessment.

FIG. 16B is assessment for a state lifting one leg, which is assessment using eyes and legs. The legs may be divided into the right and the left. The body sensor module 1040 may be used together, and the number of times of measurement and a measurement time may be set. A movement distance of the COP, a movement length image of the COP, a movement area of the COP, or an average speed of the COP may be derived as the result of the assessment.

FIG. 16C is assessment for a state sitting still, which is assessment using eyes. The body sensor module 1040 may be used together, and the number of times of measurement and a measurement time may be set. A movement distance of the COP, a movement length image of the COP, a movement area of the COP, or an average speed of the COP may be derived as the result of the assessment.

Figure 17A:
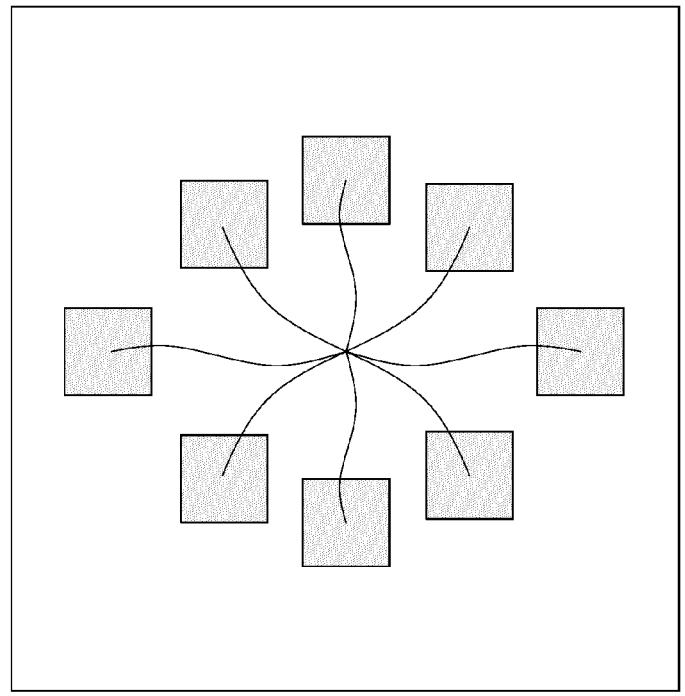
FIGS. 17A, 17B, 18A, and 18B are drawings illustrating a manner which performs dynamic assessment according to the present disclosure.

FIG. 17A is assessment for a limit of stability (LOS), which is assessment of measuring whether a user is movable to some degree in all directions in one place. A movement area of the COP and an area image of the COP may be derived as the result of the assessment.

Figure 17B:
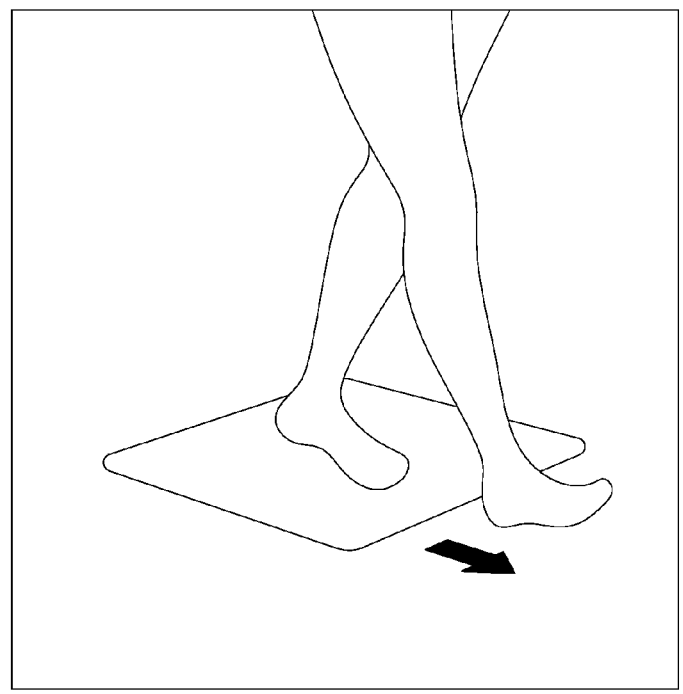

FIG. 17B is assessment for a walking state of the user. The right leg and the left leg may be distinguished. A movement direction and a pressure distribution of the COP may be derived as the result of the assessment.

The assessment for the walking state of the user may be defined as gait assessment. Upon the gait assessment, the sensing pad 1010 is placed to allow the user to step across the sensing pad 1010 to assess the walking state of the user.

At this time, the right leg and the left leg of the user should be distinguished to derive the result of the assessment. Although the user is guided to step across the sensing pad 1010 using his or her specific leg on assessment, when the user performs assessment using the other leg, there may be a problem where the result of the assessment is not accurately derived.

Thus, in the present embodiment, as an arrow displaying a direction of use is displayed on the sensing pad 1010, the user may identify it, may distinguish a direction of the sensing pad 1010 to arrange the sensing pad 1010, and may perform assessment. There is an effect where the sensing pad 1010 may sense whether the user steps across any of a right side and a left side on the sensing pad 1010 and may distinguish whether a foot where the user performs the assessment is any foot.

However, although distinguished using the location on the sensing pad 1010 to determine whether the user steps across the sensing pad 1010 using which foot, when the user steps across a right portion on the sensing pad 1010 using the left foot or when the user steps across a left portion on the sensing pad 1010 using the right foot, there may be an error in the result of the assessment.

To address it, in an embodiment, both of two feet may be allowed to be placed on the sensing pad 1010 before gait assessment, and a shape of each foot of the user may be measured using the COP, plantar pressure, and/or the like of the two feet. The user may automatically recognize a foot which performs assessment irrespective of any foot to derive the result of the assessment, without a guide speech of a disposal location of the sensing pad 1010 or a foot which should perform gait assessment based on the measured result.

Figure 18A:
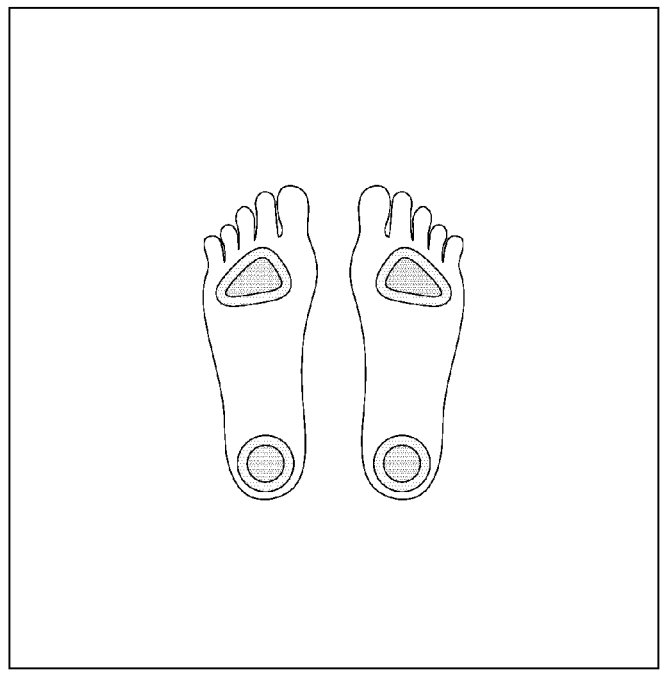
Figure 19A:
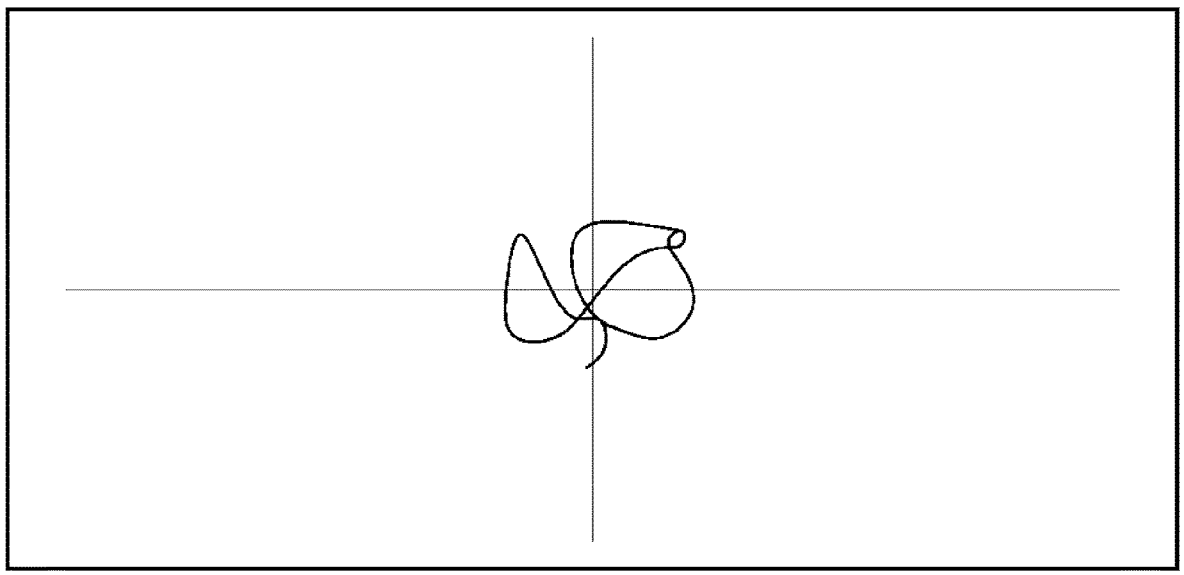
FIGS. 19A and 19B are drawings illustrating a manner which performs pressure assessment according to the present disclosure.
Figure 19B:
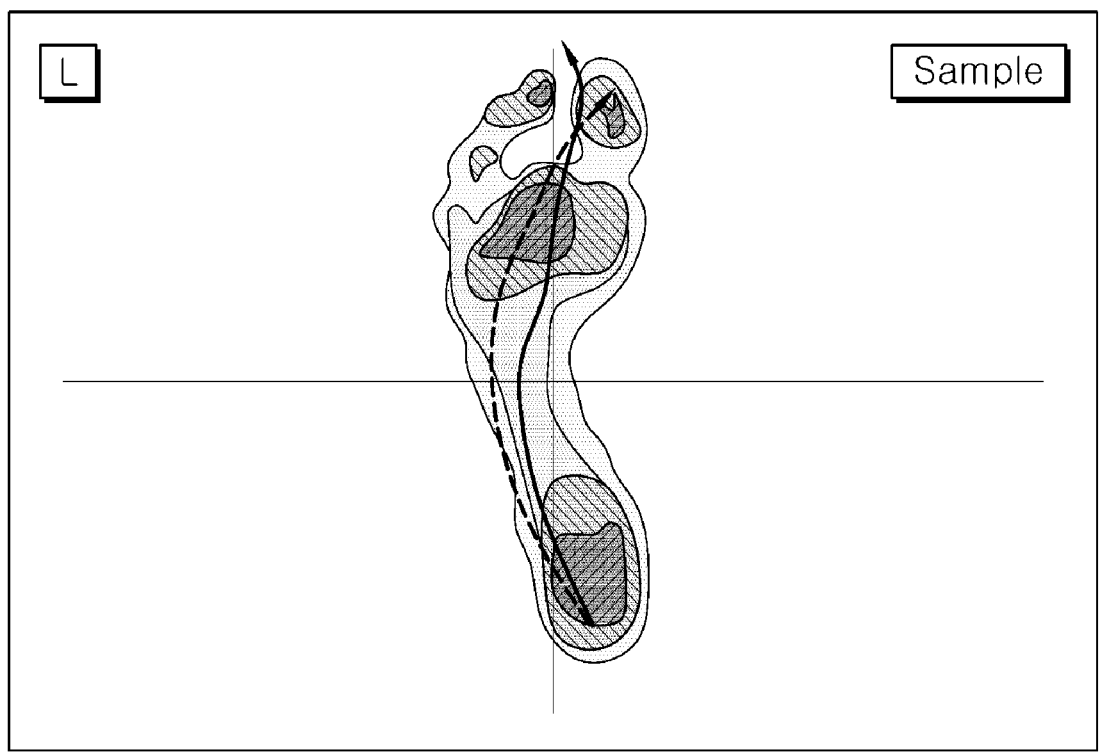

FIG. 18A is assessment for plantar pressure. A measurement time may be set. A weight support rate and a pressure distribution may be derived as the result of the assessment.

Figure 18B:
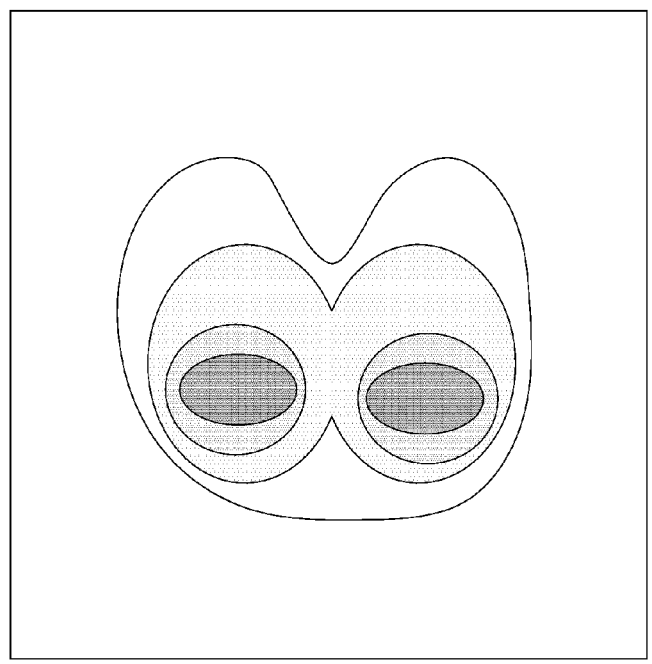

FIG. 18B is assessment for sit pressure. A measurement time may be set. A movement area, a weight support rate, and a pressure distribution of the COP may be derived as the result of the assessment.

Figure 22:
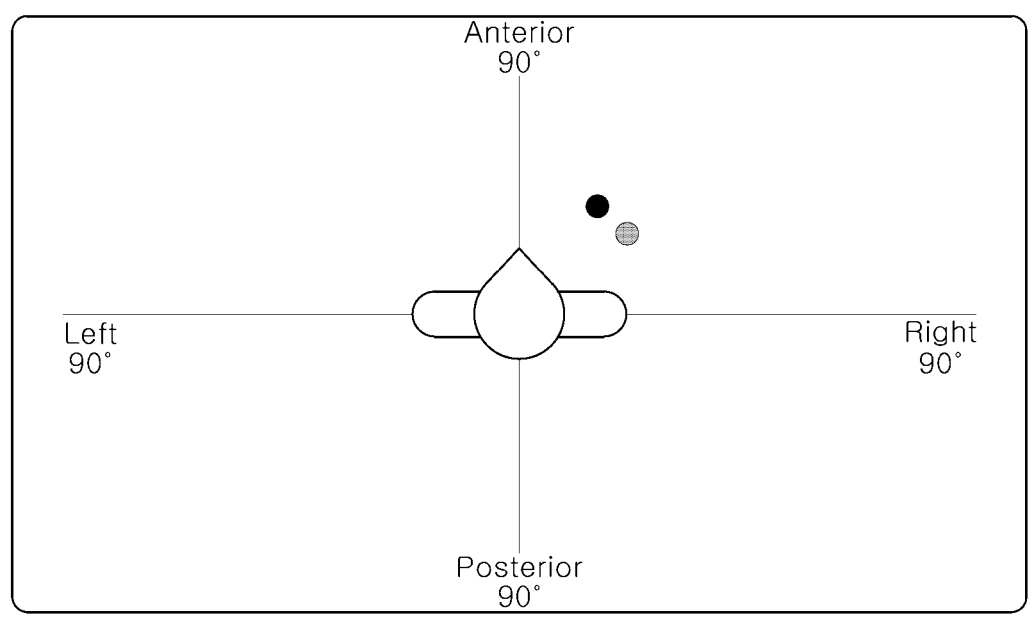

FIGS. 19A and 22 are drawings illustrating an assessment result screen according to the present disclosure.

FIGS. 19A and 19B are drawings illustrating a result of measuring the COP. It is verified that FIG. 19A illustrates a movement path of the COP and illustrates a movement length of the COP, a movement area of the COP, and an average speed of the COP and FIG. 19B illustrates a path where the COP is moved on a foot of a user.

Figure 20A:
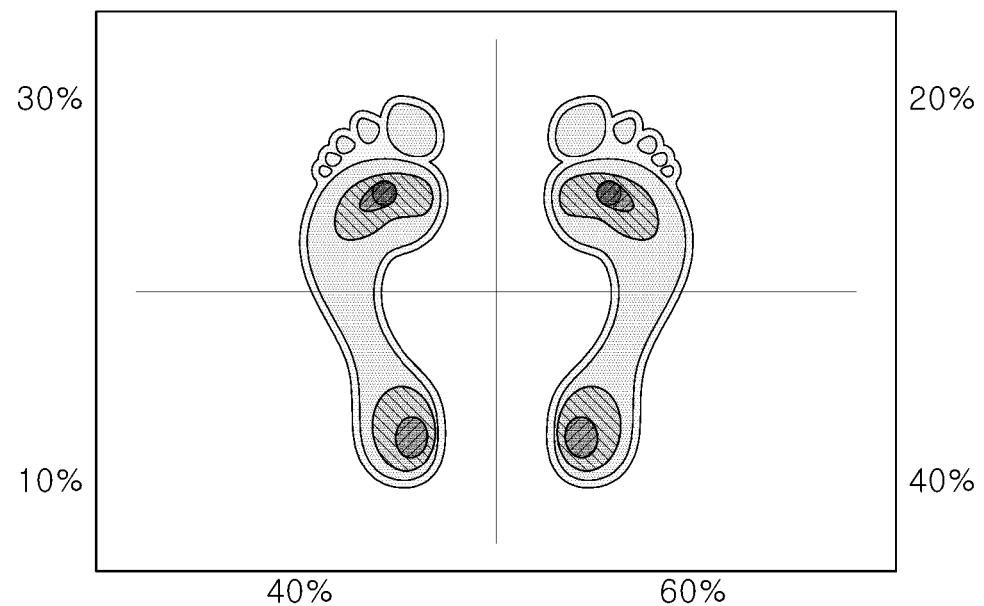
FIGS. 20A, 20B, 21, and 22 are drawings illustrating an assessment result screen according to the present disclosure.
Figure 20B:
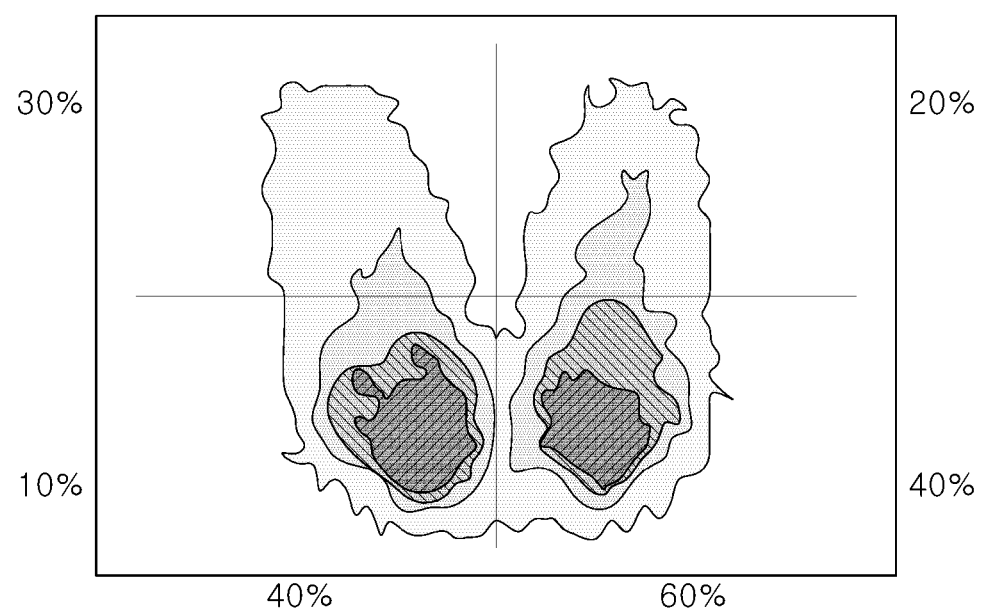

FIGS. 20A and 20B are drawings illustrating a weight support rate and a pressure distribution. It is verified that FIG. 20A illustrates a weight support rate and a pressure distribution of plantar pressure and FIG. 20B illustrates a weight support rate and a pressure distribution of sit pressure. Referring to FIGS. 20A and 20B, on a screen in the same form as a sensing pad 1010, the sensing pad 1010 may be divided into four parts to indicate a weight support rate. The pressure distribution may be displayed in color and may indicate that it corresponds to higher pressure as it goes from a blue color to a red color.

Figure 21:
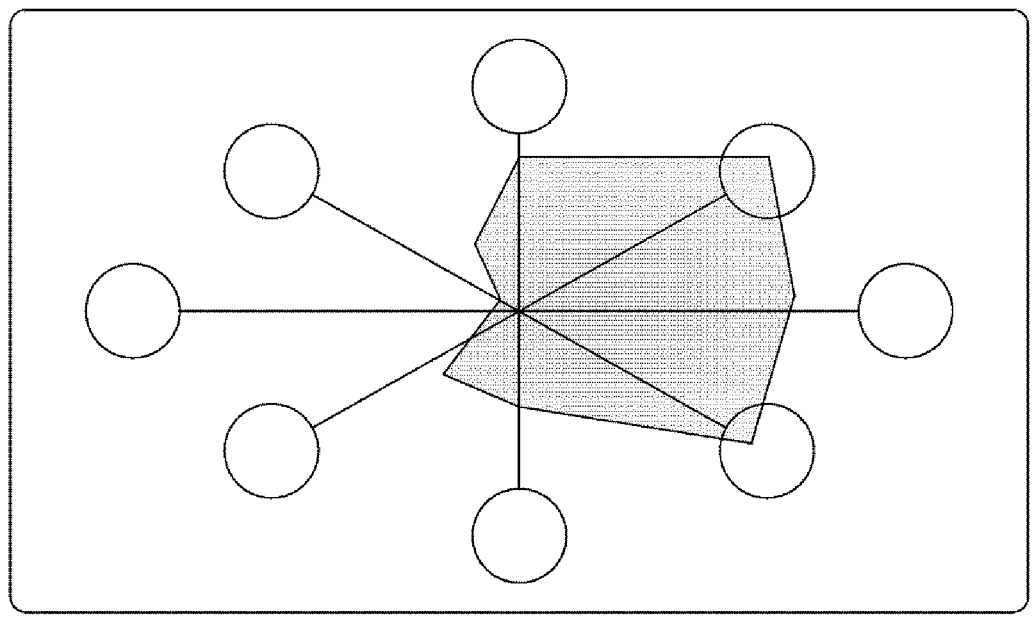

FIG. 21 is a drawing illustrating the result of assessing a LOS of FIG. 17A. It may be verified that FIG. 21 illustrates a movement area of the COP on a screen in the same form as a sensing pad 1010 and illustrates a movement area of the COP in numerical values.

FIG. 22 is a drawing illustrating a result value of tilt sensor data obtained by a body sensor module 1040. It is verified that FIG. 22 illustrates a coordinate location of tilt sensor data on a screen in the same form as a sensing pad 1010 and in numerical values.

Hereinafter, a description will be given of a method for performing balance training using a sensing device of the present disclosure and deriving the result of training.

Figure 23:
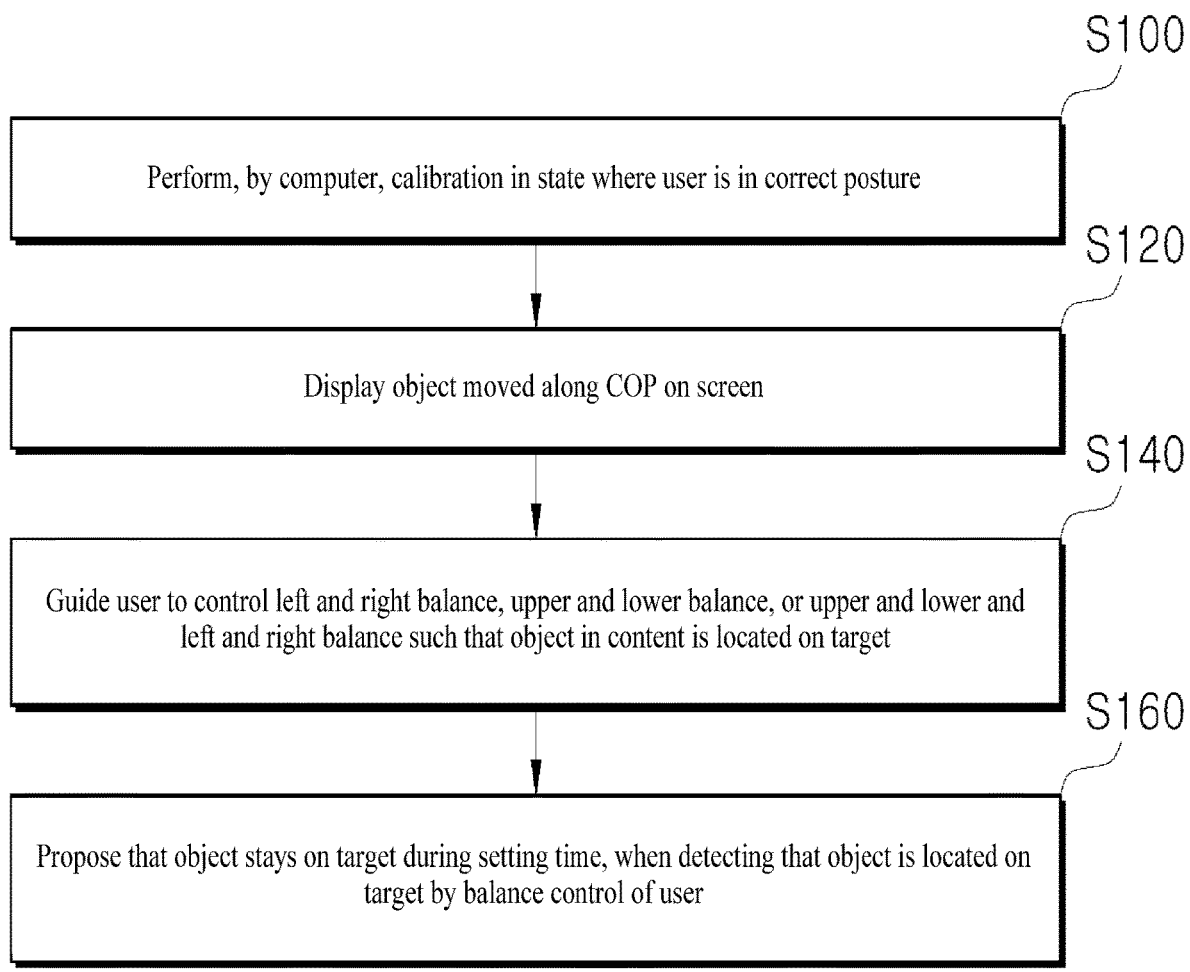
FIGS. 23, 24, and 25 are flowcharts of a training method through training content according to the present disclosure.
Figure 25:
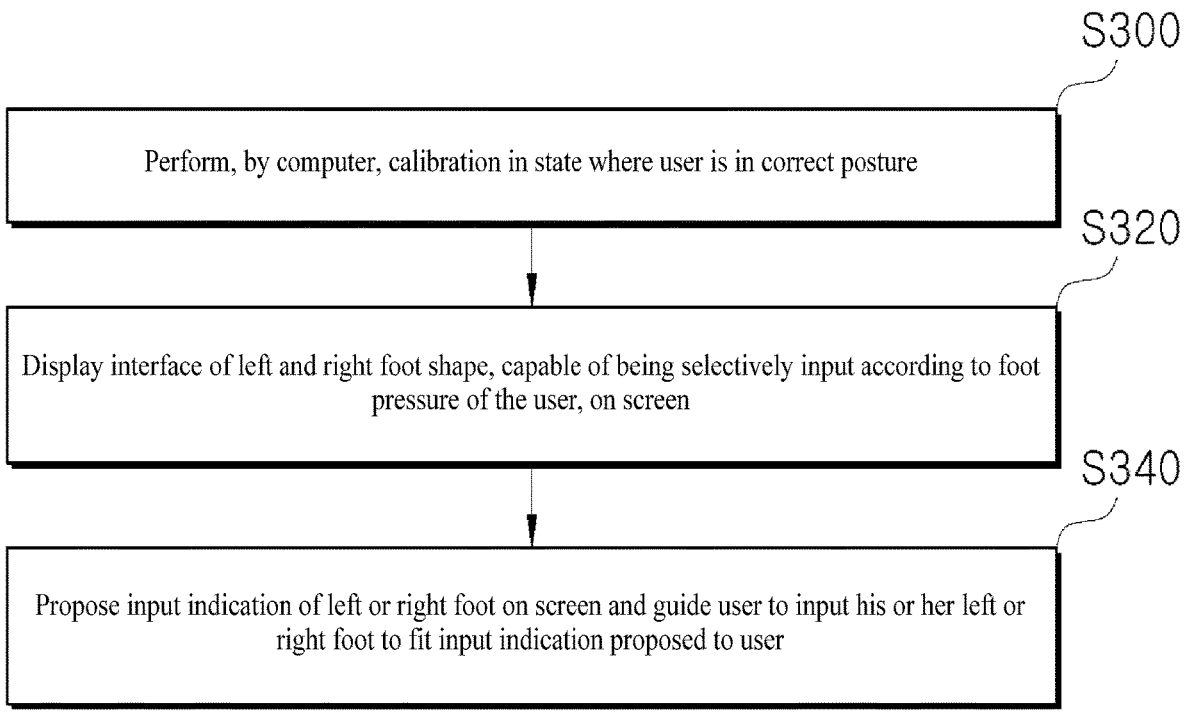

FIGS. 23 and 25 are flowcharts of a training method through training content according to the present disclosure.

In an embodiment, as types of training, static training, dynamic training, sit to stand training, and step training may be included.

Furthermore, upon balance training, a body sensor module 1040 may be worn together to obtain tilt sensor data, and only a sensing pad 1010 may be used to perform training, without the body sensor module 1040. The top and the bottom on training may correspond to the front and the rear in view of the user.

FIG. 23 is a flowchart of a training method through static training content according to the present disclosure. Static training may include performing (S100), by a computer, calibration in a state where a user is in a correct posture, displaying (S120), by the computer, an object moved along the COP on a screen, guiding (S140) the user to control left and right balance, upper and lower balance, or upper, lower, left, and right balance such that the object in content is located on a target, and proposing (S160) that the object stays on the target during a setting time, when detecting that the object is located on the target by the balance control of the user.

As the user moves only the center of mass without movement of his or her feet on a portion located on a sensing pad 1010, the static training may be performed.

In detail, the static training may include training maintaining the center of gravity (COG), while the user stands, sits, or stands with one foot on the sensing pad 1010.

In more detail, the static training may include block building training, long-lasting training in a correct posture, training maintaining a left and right balance level, or training maintaining the center.

The block building training may be training allowing a character to move to the left and right with respect to the COP and pile up blocks in a line. When the piled-up blocks do not maintain their balance and collapse, the block building training may be ended. The block building training may set a training time and a training difficulty level and may derive a training time, a training score, and a weight support rate as the result of the training.

The long-lasting training in the correct posture may be configured such that, when the COP is tilted, a corresponding character is tilted together in proportion to the angle, and such that, when the character is tilted over a certain angle, the character falls down in a corresponding direction, and should maintain front and rear and left and right tilts. The long-lasting training in the correct posture may derive a training time, a training score, a success rate, or a weight support rate as the result of the training.

In the training maintaining the left and right balance level, when the left and right balance level is different over a specific criterion, the game may be finished as failure processing. The training maintaining the left and right balance level may set a training time and may derive a training time and a weight support rate as the result of the training.

The training maintaining the center may be that the game is finished when the center is greater than or equal to a specific criterion, which may be training for a front and rear and left and right balance level. The training maintaining the center may set a training time, a training difficulty level, a holding time, and a break and may derive a training time, a movement path of the COP, a movement length of the COP, a movement area of the COP, and a movement speed of the COP as the result of the training.

Figure 24:
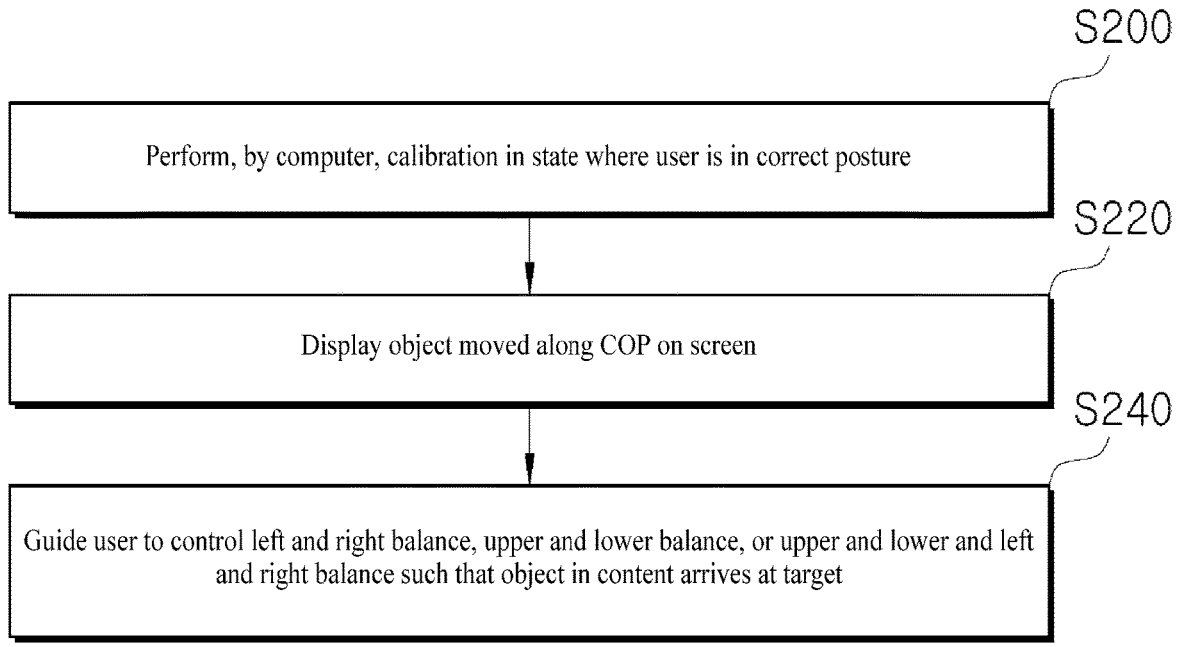

FIG. 24 is a flowchart of a training method through dynamic training content according to the present disclosure. Dynamic training may include performing (S200), by a computer, calibration in a state where a user is in a correct posture, displaying (S220) an object moved along a COP on a screen, and guiding (S240) a user to control left and right balance, upper and lower balance, or upper and lower and left and right balance such that the object in content arrives at a target.

As it is possible for the user to moves his or her feet on a portion where there are located on the sensing pad 1010, the dynamic training may be performed using the movement of the feet and movement of the center of mass.

In detail, the dynamic training may include training maintaining balance of the center of gravity in the range of the limit of stability on the sensing pad 1010 or moving over the sensing pad 1010.

In more detail, the dynamic training may include training moving a specific object up and down or from side to side away from an obstacle, training avoiding an obstacle in all directions, training moving an object moved in all directions in order, training following the center along a moving object, training moving along various types of trajectories, or training moving back and forth or from side to side to move an object.

The training moving the specific object up and down or from side to side away from the obstacle may be training avoiding an obstacle approaching such that the user may move the object configured to only move up and down or from side to side. The training moving the specific object up and down or from side to side away from the obstacle may set a training time and a training difficulty level and may derive a training time and a training score as the result of the training.

The training avoiding the obstacle in all the directions may be training voiding the object approaching in several directions in all the directions. The training avoiding the obstacle in all the directions may set a training time and a training difficulty level and may derive a training time and a training score as the result of the training.

The training moving the object moved in all the directions in order may be training allowing the user to move along a straight distance in an order where the object moves, as the object moves in the straight distance without being distinguished up and down and from side to side.

The training moving the object moved in all the directions in order may set a training difficulty level and may derive a training time and a training score as the result of the training.

The training following the center along the moving object may be training following the object while maintaining the center within the object in a certain range as the object moves.

The training following the center along the moving object may set a training time, a training difficulty level, and a holding time and may derive a training time, a movement path of the COP, a movement length of the COP, a movement area of the COP, and a movement speed of the COP as the result of the training.

The training moving along the various types of trajectories may be similar in form to the training following the center along the moving object and may be training showing the various types of trajectories and moving the center along an object moving along the corresponding trajectory.

The training moving along the various types of trajectories may set a training time, a training difficulty level, and a holding time and may derive a training time, a movement path of the COP, a movement length of the COP, a movement area of the COP, and a movement speed of the COP as the result of the training.

The training moving back and forth to move the object may be configured, when the user moves back and forth or from side to side, such that the object moves in a corresponding direction, which may be training allowing the user to move back and forth or from side to side to arrive at a location where the object should be disposed.

The training moving back and forth to move the object may set a training time, a training difficulty level, a left and right target rate, or a front and rear target rate and may derive a training time, the number of times of success, and a weight support rate as the result of the training.

The sit to stand training may correspond to training standing while maintaining a left and right weigh support rate in a posture sitting on a chair outside the sensing pad 1010, in a state where feet is placed on the sensing pad 1010.

The sit to stand training may be training sitting and perfectly standing during a countdown, may set a training time, and may derive a training time as the result of the training.

FIG. 25 is a flowchart of a training method through step training content according to the present disclosure. Step training may include performing (S300), by a computer, calibration in a state where a user is in a correct posture, displaying (S320) an interface of a left and right foot shape, capable of being selectively input according to foot pressure of the user, on a screen, and proposing (S340) a note of the left or right foot on the screen and guiding the user to input his or her left or right foot to fit the proposed note.

When the user inputs his or her left or right foot to fit the proposed input indication in the providing (S340) of the input indication of the left or right foot on the screen and guiding the user to input the left or right foot to fit the proposed input indication, it is assessed that the user synchronizes timing of proposing the input indication with timing of inputting the left or right foot to some degree.

In detail, the step training may include training walking in place using left and right plantar pressure on a sensing pad 1010.

In more detail, the step training may be training walking in place, which may be training walking with a left or right foot indicated on a screen, may set a training difficulty level and a left and right appearance rate, and may derive a training time, a training score, a success rate, and a left and right support time as the result of the training.

FIGS. 26A to 27B are drawings illustrating a training result screen according to the present disclosure.

Figure 26A:
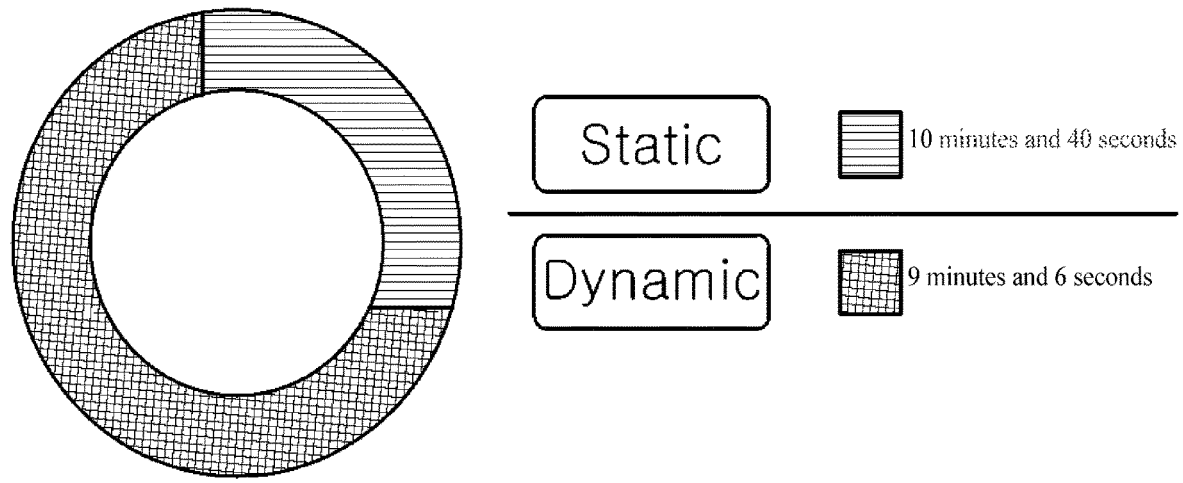
FIGS. 26A, 26B, 27A, and 27B are drawings illustrating a training result screen according to the present disclosure.

FIG. 26A illustrates a training time. Referring to FIG. 26A, the ratio of a static training time to a dynamic training time may be provided to be roughly identified, as an overall assessment, and time may be provided in numerical values.

Figure 26B:
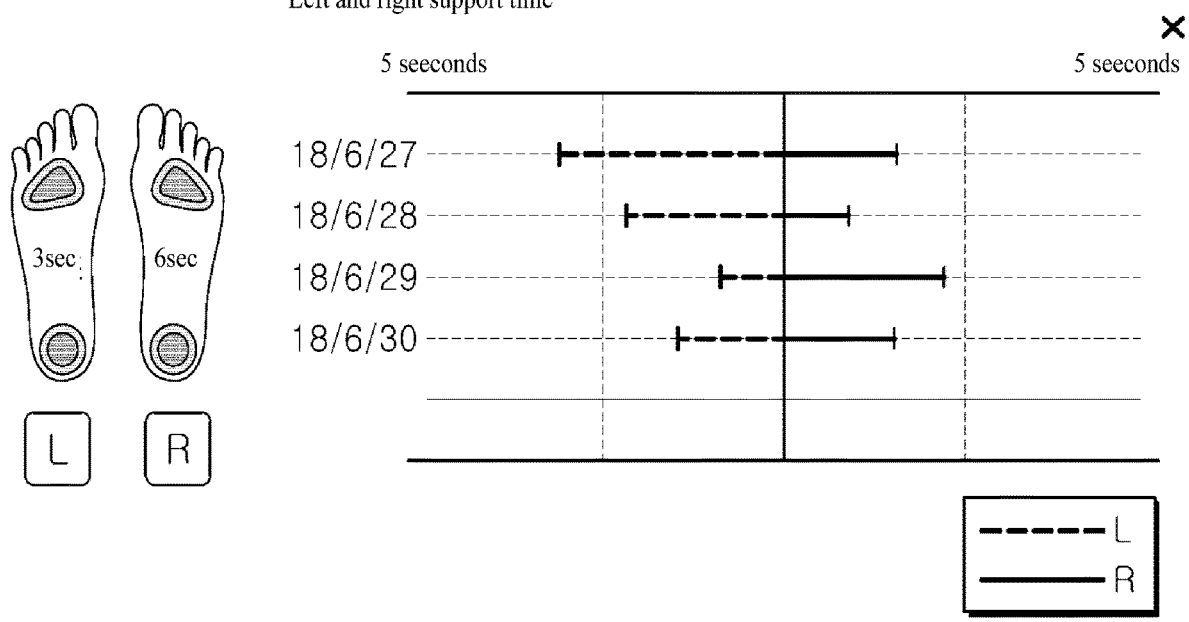

FIG. 26B illustrates a left and right support time. Referring to FIG. 26B, a graph or the like may be provided to indicate the sum of a right foot support time and a left foot support time and identify a left and right support time for each date.

Figure 27A:
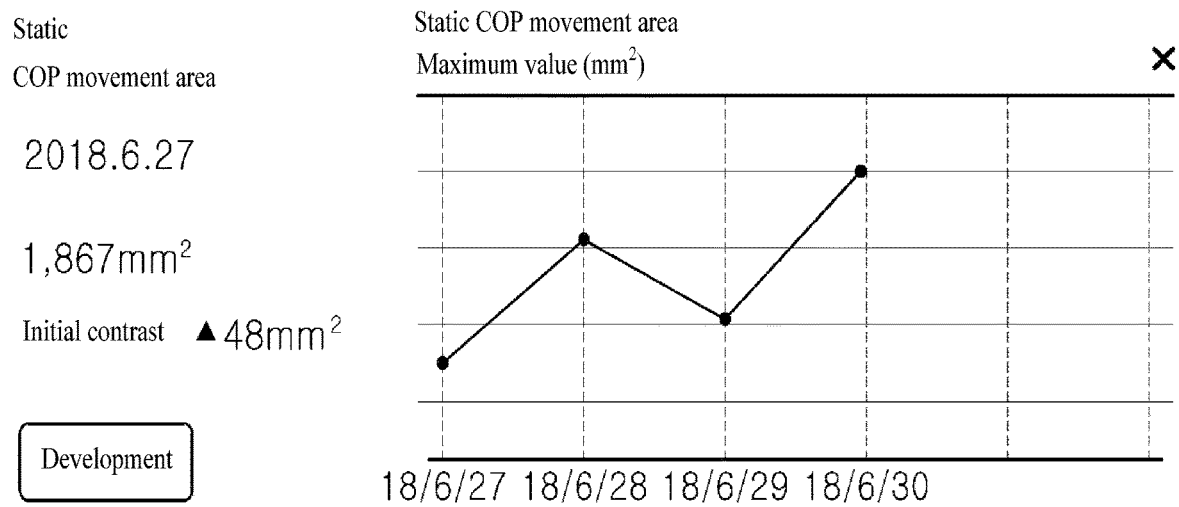

FIG. 27A illustrate a movement area of the COP. Referring to FIG. 27A, a graph or the like may be provided to indicate the movement area of the COP in numerical values and identify the movement area of the COP for each date.

Figure 27B:
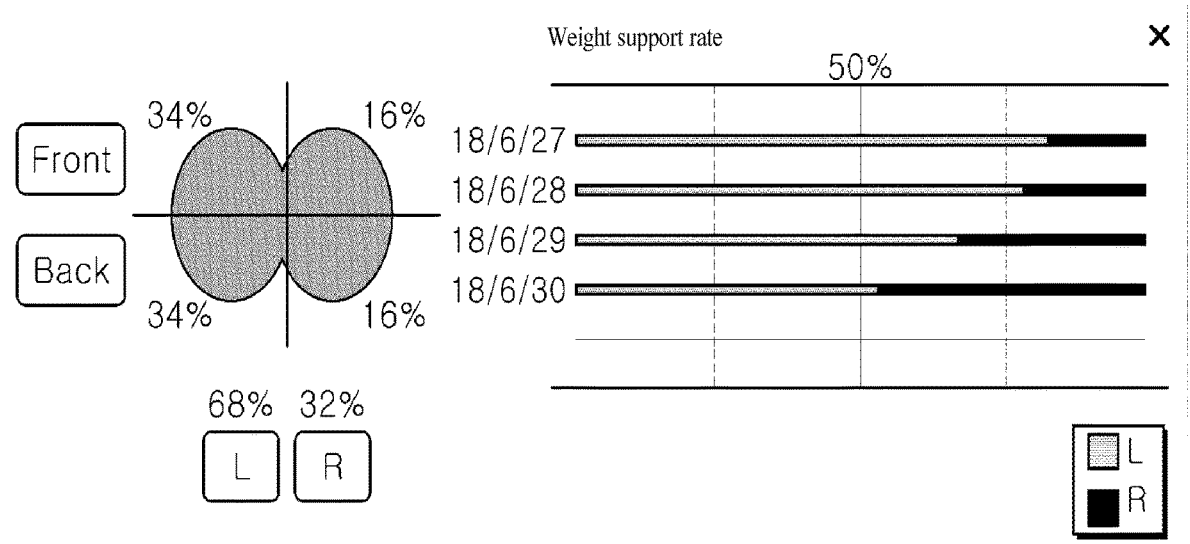

FIG. 27B illustrates a weight support rate. Referring to FIG. 27B, a graph or the like may be provided to divide a sensing pad 1010 into four parts on a screen shown in the form of the sensing pad 1010 to display the weight support rate in numerical values and identify a left and right weight support rate for each date.

Furthermore, although not illustrated in FIGS. 26A to 27B, various result values provided as training result values may also be indicated in the form of he sensing pad 1010 or may be indicated in the form of a graph.

Figure 28:
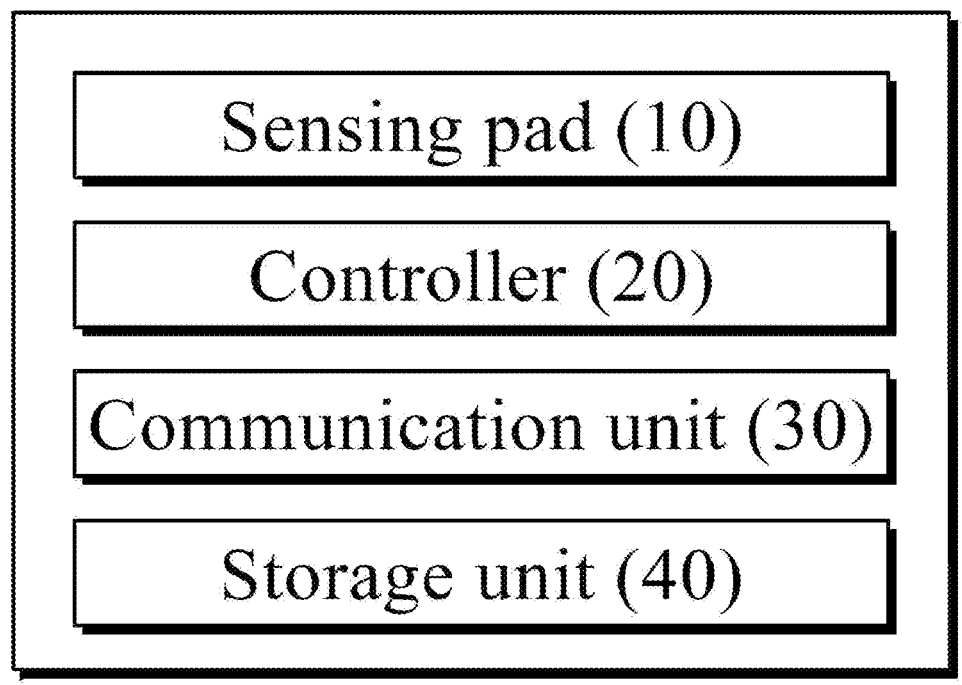
FIG. 28 is a drawing illustrating a configuration of a sensing device according to the present disclosure.

FIG. 28 is a drawing illustrating a configuration of a sensing device according to the present disclosure.

Referring to FIG. 28, a sensing device 100 according to the present disclosure may include a sensing pad 10 and a controller 20.

The sensing device 100 may include collect information such as pressure, acceleration, a tilt, temperature, humidity, light, heat, a sound, electromagnetism, or an ultrasonic wave.

As a detailed example, the sensing device 100 may be, but is not limited to, a pressure sensing device which measures pressure applied from a user.

The sensing pad 10 may include a plurality of sensors 12 to obtain sensing data 200 of the user.

Figure 29A:
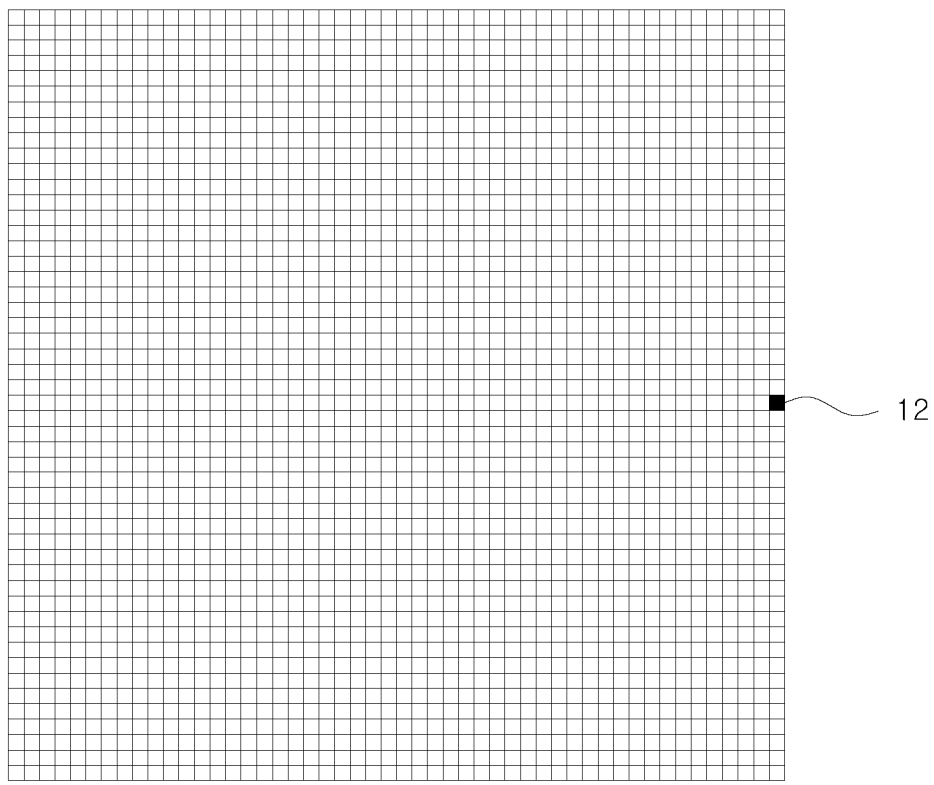
FIGS. 29A, 29B, and 29C are drawings illustrating a sensing pad of a pressure sensing device and an output screen of pressure sensing data according to the present disclosure.
Figure 29B:
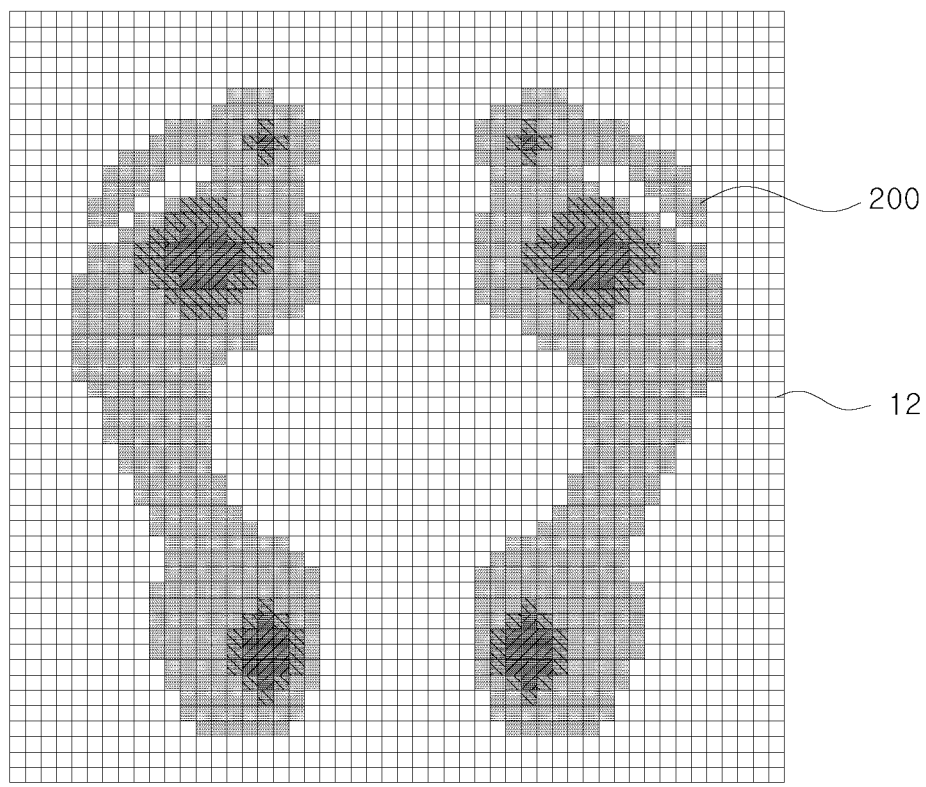
Figure 29C:
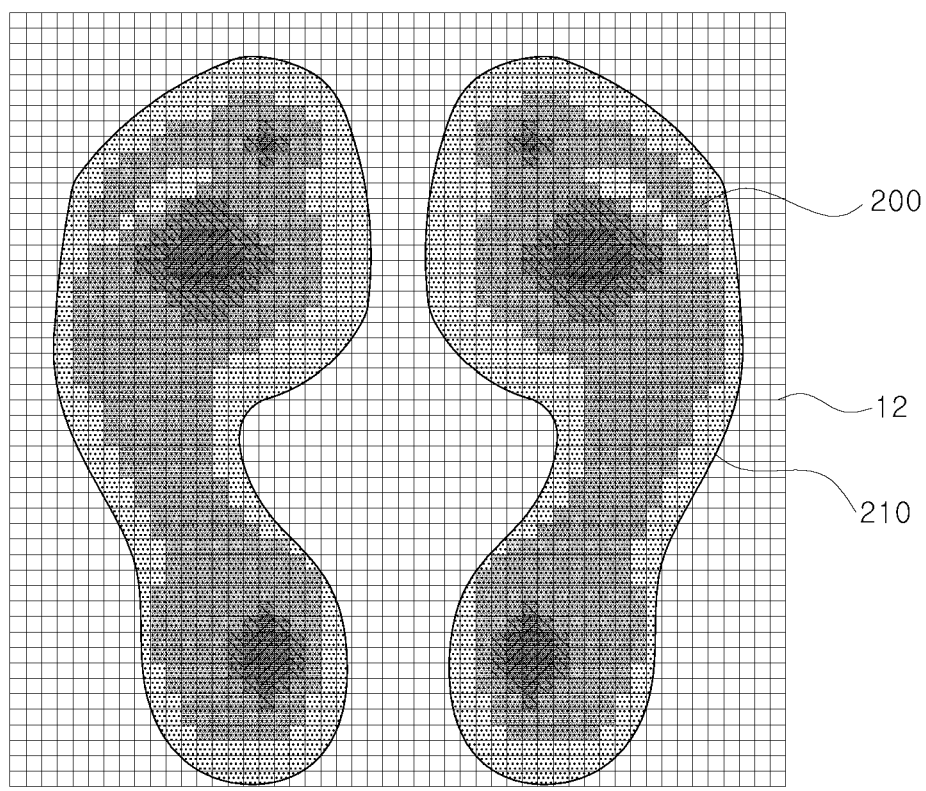

FIGS. 29A to 29C are drawings illustrating a sensing pad of a pressure sensing device and an output screen of pressure sensing data according to the present disclosure.

Referring to FIG. 29A, as a detailed example, a sensing pad 10 of the pressure sensing device may be configured such that a plurality of sensors 12 for outputting a sensing value for pressure applied to each sensor are arranged on a plane. That is, in the example of FIG. 29A, the one sensor 12 may be included for each cell in the sensing pad 10.

In an embodiment, the plurality of sensors 12 may obtain respective sensing values in a specific measurable range.

As a detailed example, the one sensor 12 may output one of consecutive sensing values included in a predetermined measurable range. That is, each of the plurality of sensors included in the sensing device may output any one of sensing values included in the same numerical value range.

For example, when a pressure sensor is configured to output any one sensing value among 0 to 99, each of the plurality of pressure sensors included in the pressure sensing device may output corresponding one sensing value among 0 to 99 depending on applied pressure.

Sensing data 200 may refer to data collected by the sensing pad 10 included in a sensing device 100.

In an embodiment, the sensing data may be raw data which does not pass through processing such as extraction or compression.

Figure 30:
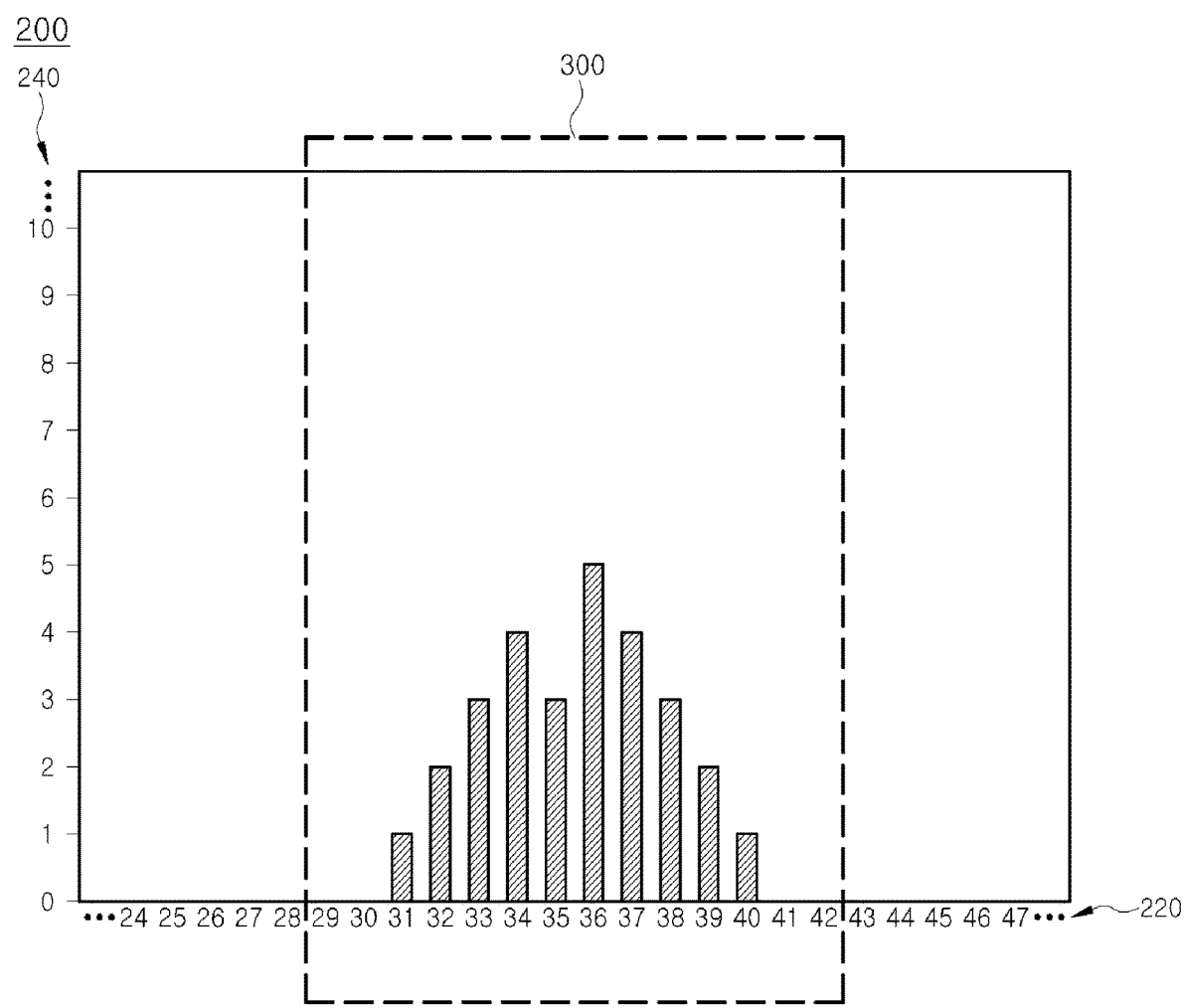
FIG. 30 is a drawing illustrating sensing data according to the present disclosure.

FIG. 30 is a drawing illustrating sensing data according to the present disclosure.

Referring to FIG. 30, in an embodiment, sensing data 200 may include number information 240 which is the number of sensors which output respective sensing values 220.

As a detailed example, in case of FIG. 30, the sensing data 200 may include the number information 240 about the respective sensing values 220, for example, that a sensor outputting a sensing value of 30 is 0, that a sensor outputting a sensing value of 31 is 1, that sensors outputting a sensing value of 32 are 2, or that sensors outputting a sensing value of 33 are 3, among a plurality of sensors 12 included in a sensing pad 10.

Furthermore, although not illustrated in the drawing, in an embodiment, the sensing data 200 may include arrangement location information about arrangement locations of the respective sensors 12 arranged on the sensing pad 10.

As a detailed example, in the sensing pad 10 of the pressure sensing device as shown in FIG. 29A, when sensors outputting a sensing value of 33 are 3, information about arrangement locations where the respective sensors 12 outputting the sensing value of 33 are positioned on the sensing pad 10 may be included.

In this case, as shown in FIG. 29B, sensing data may be output in a color corresponding to each sensing value (e.g., a blue color corresponding to the lowest sensing value in a specific range and a red color corresponding to the highest sensing value) using a sensing value and arrangement location information output from each sensor 12, which are included in sensing data. However, because this is merely illustrative, the sensing device and the sensing data of the present disclosure are not limited thereto.

A controller 20 may extract data in an extraction area 300 set in the sensing data 200 to generate extraction data 400. That is, the controller 20 may generate extraction data based on sensing data obtained by the sensing pad 10.

Furthermore, in an embodiment, prior to generating the extraction data (400 of FIGS. 32B and 32C), the controller 20 may remove a noise of the sensing data 200.

This will be described with an example of a pressure sensing device configured to include a sensing pad where a plurality of pressure sensors are arranged at a specific interval on a plane as shown in FIG. 29A and a board provided on an upper portion of the sensing pad.

When a body part (e.g., feet) of the user comes into contact with the board, as the board applies pressure to the sensing pad, the plurality of pressure sensors arranged on the sensing pad may output various sensing values. At this time, as shown in FIG. 29C, because it is able to apply pressure to the board and the sensing pad of an area 210 with which the body part of the user does not come into direct contact, the plurality of pressure sensors located on the area 210 may output sensing values and noise may be generated. Thus, there is a need to remove the generated noise to obtain only a sensing value for an area with which the body part of the user comes into direct contact.

As a detailed example, the method for removing noise may be to change a sensing value of a predetermined valid sensing value or less among sensing values output by the plurality of sensors to 0. That is, when a sensing value output by a pressure sensor of the area 210 with which the body part does not come into direct contact is generally less than a sensing value output by a pressure sensor of the area with which the body part comes into direct contact, a sensing value of a certain numerical value or less may be determined as noise to be removed.

In this case, the controller 20 may set a valid sensing value which becomes a noise determination criterion and may determine a sensing value of the set valid sensing value or less as noise to change it to 0, thus obtaining sensing data in which noise is removed, as shown in FIG. 29B.

Next, the controller 20 may extract data in the extraction area 300 set in the sensing data 200 to generate the extraction data 400.

The extraction data 400 may refer to data generated by extracting some data from the sensing data 200.

Referring to FIG. 30, the extraction area 300 may be an area set for the sensing data 200 to generate extraction data.

The extraction data may have a smaller size value than sensing data. That is, the extraction area may be set for a partial range in the entire range of the sensing data.

A transfer rate of data may vary with a size of the transmitted data. Like the above embodiment, some of the sensing data 200 obtained by the sensing device 100 may be extracted to generate the extraction data 400 of a size smaller than the sensing data and it may be transmitted to a computer to improve a data transfer rate.

As a detailed example, a size of raw sensing data obtained from a plurality of pressure sensors by a pressure sensing device may be 12 bits. When the size of the sensing data decreases to 8 bits to improve a transfer rate, an extraction area having a size of 8 bits may be set for all sensing data to generate extraction data.

In an embodiment, the sizes of the sensing data and the extraction data may be proportional to the range of sensing values included in the data (i.e., the number of the included sensing values).

As a detailed example, refer to FIGS. 3A and 3B, when sensing values included in the sensing data 200 are 0 to 99 (100) and when sensing values included in the extraction area 300 are 29 to 42 (14), a size of the extraction data 400, in which the number of the included sensing values is less, may be smaller than a size of the sensing data 200.

That is, the number of the sensing values included in the extraction area 300 may be determined in the range less than the number of all sensing values included in the sensing data 200, and this may be determined according to the size of the extraction data 400 required a cause such as a transfer rate.

Meanwhile, referring to the above-mentioned example, because the number (14) of the sensing values included in the extraction area 300 is less than the number (100) of the sensing values included in the sensing data 200, as shown in FIG. 3, there is a need to set the extraction area to include the range (31 to 40) of sensing values output by a plurality of sensors included in a sensing device. On the other hand, a description will be given below of a problem when the extraction area is configured to not include some (43 to 45) of output sensing values as shown in FIG. 6.

Hereinafter, when a size of the extraction area 300 according to the present disclosure is determined (i.e., when the number of sensing values included in the extraction area is determined), a description will be given of a detailed embodiment in which a controller 20 sets the extraction area 300 for the sensing data 200 and generates the extraction data 400. A description will be given of an example of when the range of sensing values of sensing data is 0 to 99 and when the number of sensing values included in an extraction area is 14 for convenience of description, but the present disclosure is not limited thereto.

In an embodiment, the controller 20 may set an extraction area such that a sensing value with the highest number information is located on the center of the range of sensing values included in the extraction area 300.

As a detailed example, referring to FIG. 30, when a sensing value corresponding to the highest number information, 5, is 36, the controller 20 may set the extraction area 300 having the sensing value range of 29 to 42 (or 30 to 43) to locate it on the center and may extract data in the set extraction area to generate the extraction data 400.

Figure 31:
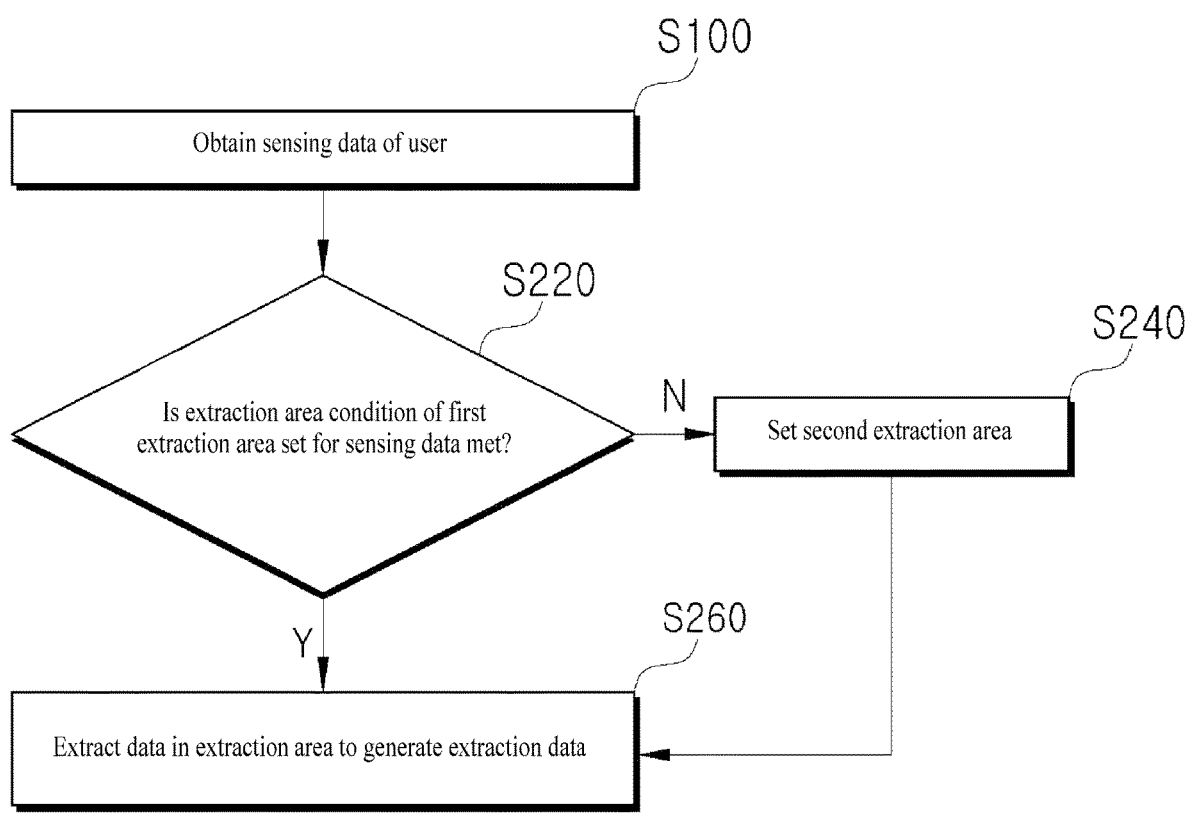
FIG. 31 is a flowchart of an algorithm for determining whether an extraction area condition of a first extraction area is met according to the present disclosure.

FIG. 31 is a flowchart of an algorithm for determining whether an extraction area condition of a first extraction area is met according to the present disclosure.

Referring to FIG. 31, in another embodiment, a controller 20 may determine whether an extraction area condition of a first extraction area (320 of FIG. 32A) set for sensing data 200 is met (S220), may extract data in the first extraction area 320 to generate extraction data 400 (S260), when the extraction area condition of the first extraction area 320 is met, and may set a second extraction area (340 of FIG. 35) (S240), when the extraction area condition of the first extraction area 320 is not met.

First of all, the controller 20 may determine whether the extraction area condition of the first extraction area 320 for the sensing data 200 is met. The first extraction area 320 may refer to an extraction area initially set for the sensing data 200.

In an embodiment, the first extraction area 320 may be set with regard to the average of sensing data for a plurality of users.

As a detailed example, for a pressure sensing device shown in FIGS. 29A to 29C, the first extraction area 320 may be preset to include it with regard to the range of output sensing values of an average user for the pressure sensing device.

In another embodiment, the first extraction area 320 may be set with regard to user information about a user who obtains sensing data.

As a detailed example, the first extraction area 320 may be preset to include it with regard to the range of output sensing values of an average user of a gender and an age similar to a gender and an age of the user who obtains the sensing data.

In an embodiment, the extraction area condition may be set based on number information about each sensing value included in the extraction area 300.

Figure 32A:
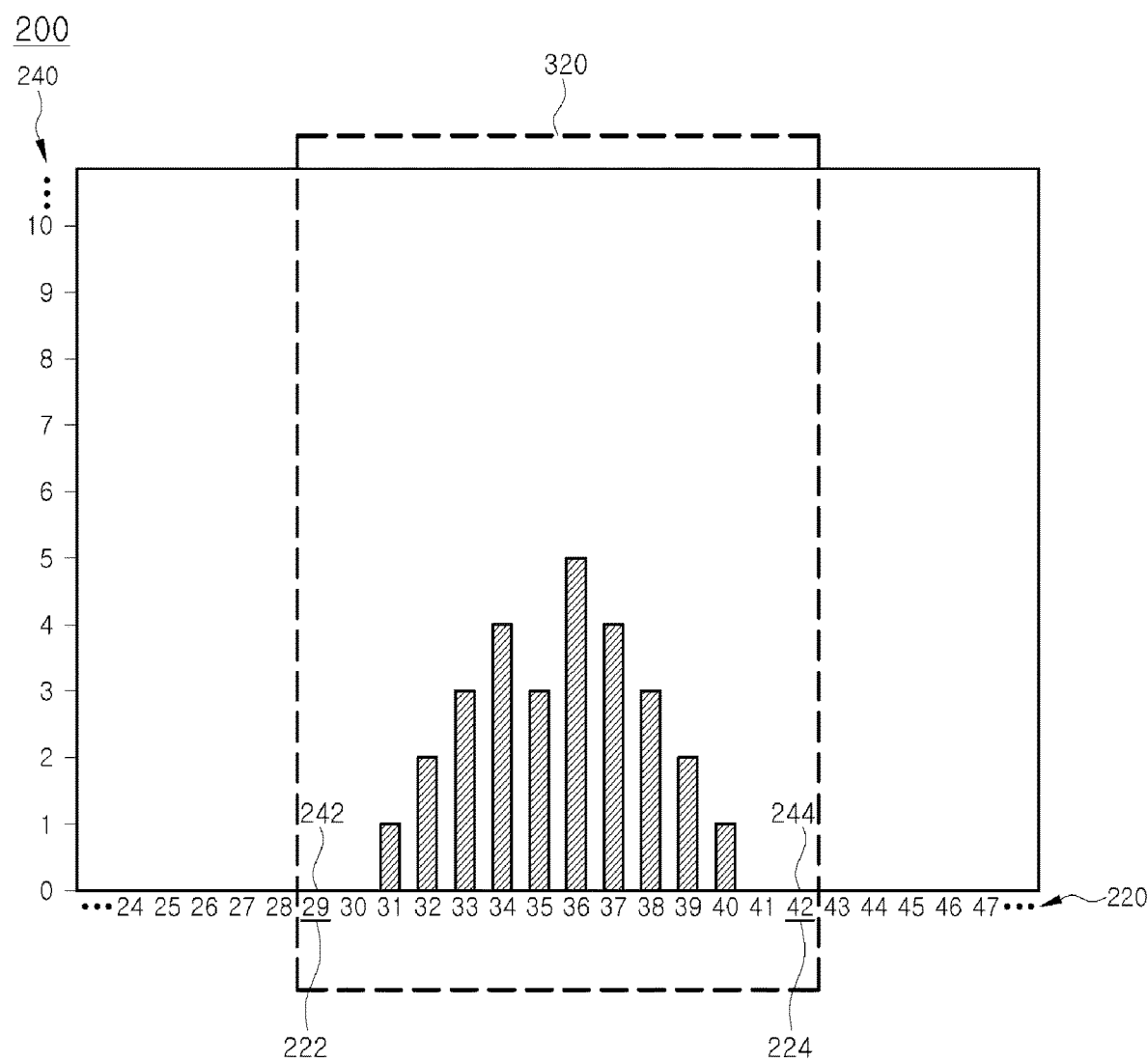
FIGS. 32A, 32B, and 32C are drawings illustrating an extraction area condition and extraction data according to the present disclosure.
Figure 32B:
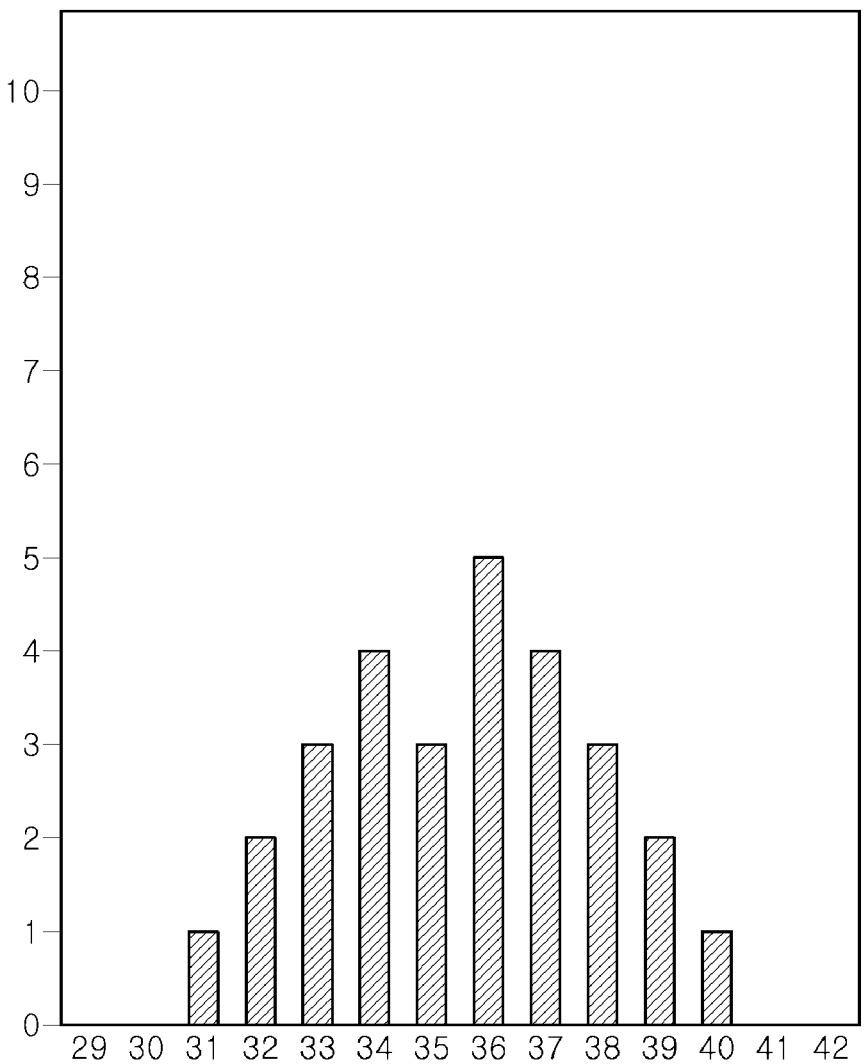
Figure 32C:
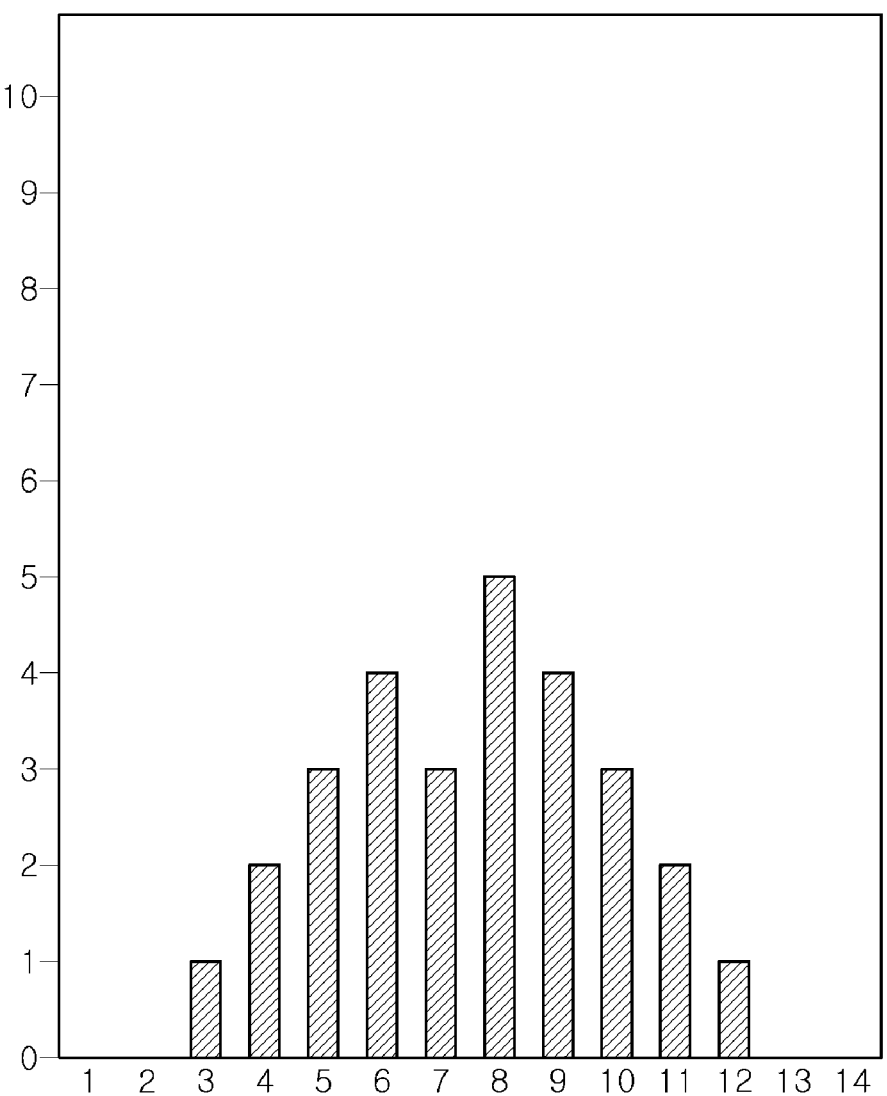
Figure 33:
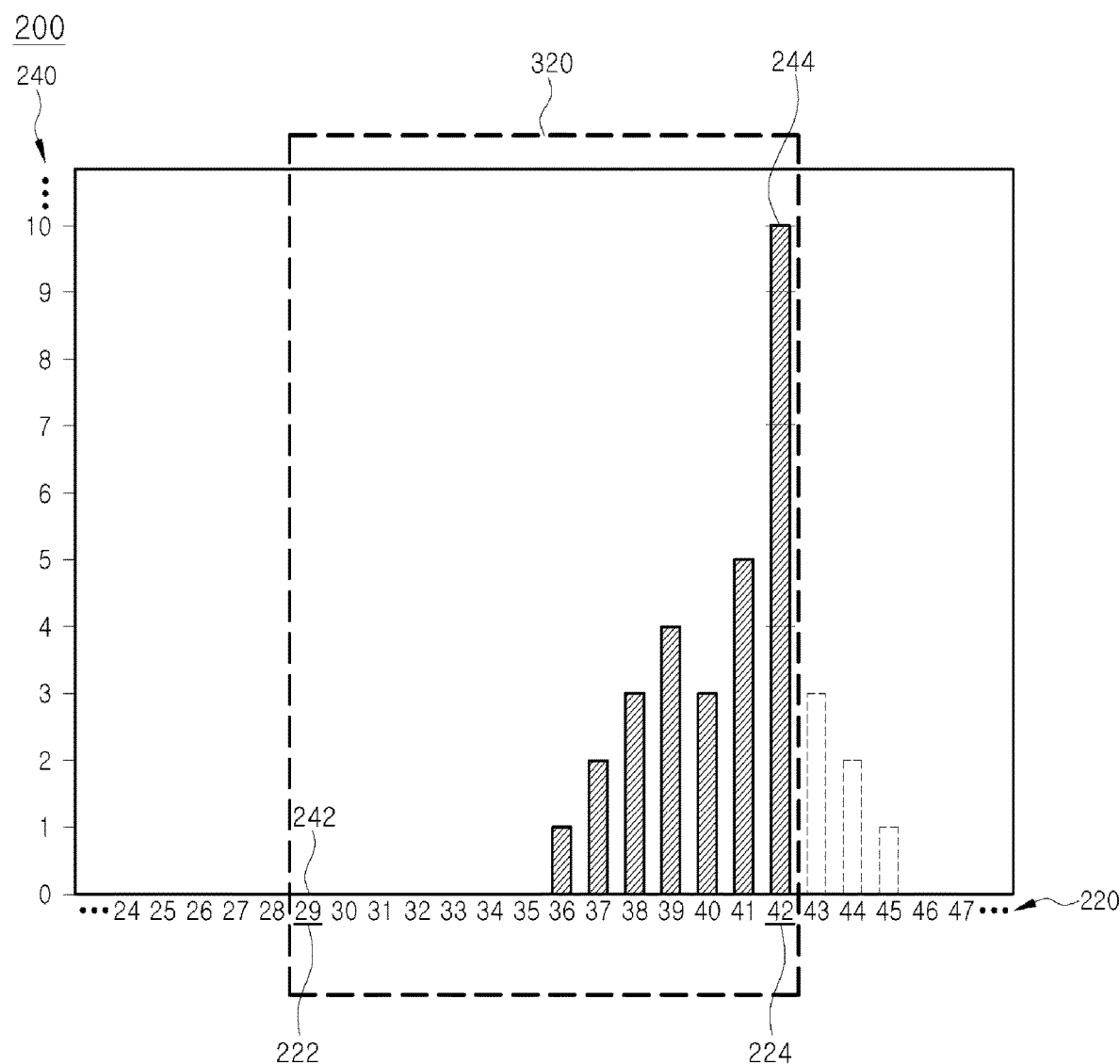
FIGS. 33 and 34 are drawings illustrating a first extraction area which does not meet an extraction area condition according to the present disclosure.
Figure 34:
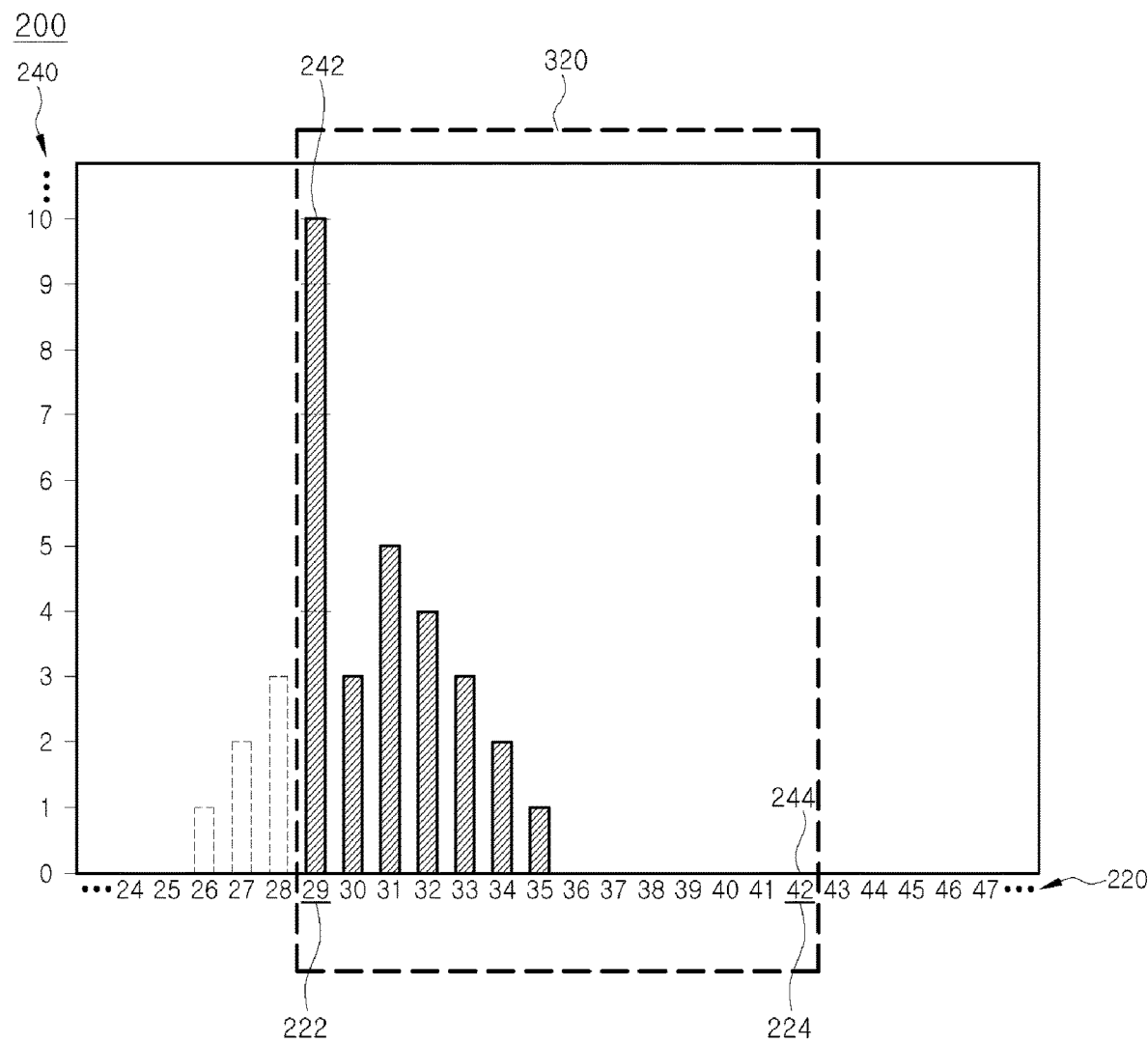

FIGS. 32A to 32C are drawings illustrating an extraction area condition and extraction data according to the present disclosure. FIGS. 33 and 34 are drawings illustrating a first extraction area which does not meet an extraction area condition according to the present disclosure. Hereinafter, the extraction area condition according to the present disclosure will be described with reference to FIGS. 33 and 34.

Referring to FIG. 32A, as a detailed example, the extraction area condition may be set based on first number information 242 and second number information 244.

At this time, the first number information 242 may be obtained by adding number information 240 about sensing values of a first sensing value 222 or less among a plurality of sensing values in sensing data 200, and the first sensing value 222 may be a sensing value with the least numerical value among a plurality of sensing values 220 in an extraction area 300.

Furthermore, the second number information 244 may be obtained by adding number information 240 about sensing values of a second sensing value 224 or more among the plurality of sensing values in the sensing data 200, and the second sensing value 224 may be a sensing value with the largest numerical value among the plurality of sensing values 220 in the extraction area 300.

That is, when the extraction area 300 is set not to include a portion of the range of the sensing values 220 output by a plurality of sensors 12, as number information about a plurality of sensing values which are not included in the extraction area 300 is added to number information (first number information or second number information) of the closest sensing value (a first sensing value or a second sensing value) among the sensing values included in the extraction area 300, extraction data 400 may be generated.

For example, in the example of FIGS. 32A to 34, the first sensing value 222 may be 29 and the second sensing value 224 may be 42.

Furthermore, the first number information 242 obtained by adding number information about sensing values of the first sensing value 222, 29, or less may be 0 in FIGS. 5 and 6 and may be 10 in FIG. 7.

Furthermore, the second number information 244 obtained by adding number information about sensing values of the second sensing value 224, 42, or more may be 0 in FIGS. 5 and 7 and may be 10 in FIG. 6.

As a detailed example, an extraction area condition may be that the first number information 242 and the second number information 244 are less than or equal to a predetermined threshold.

As another detailed example, the extraction area condition may be that the first number information 242 and the second number information 244 are 0.

That is, as shown in FIG. 33 or 34, when a first extraction area 320 is set not to include some of sensing values output by the plurality of sensors 12, because the first number information 242 or the second number information 244 shows a high numerical value, a controller 20 may set 'that the first number information 242 or the second number information 244 is less than or equal to a threshold or is 0' as the extraction area condition.

As another detailed example, the extraction area condition may be that a difference between the smallest sensing value among sensing values, each of which has number information which is not 0 in the sensing data 200, and the first sensing value 222 is equal to a difference between the largest sensing value and the second sensing value 224.

For example, in case of FIG. 32A, because a difference between the smallest sensing value, 31, among the sensing values 220, each of which has number information 240 which is not 0 in the sensing data 200, and the first sensing value 222, 29, is 2 and because a difference between the largest sensing value, 40, among the sensing values, each of which has number information which is not 0, and the second sensing value 224, 42, is 2, the first extraction area 320 of FIG. 32A may meet the extraction area condition. In the embodiment above, the extraction area condition may be set to place the range of the sensing values 220 output by the plurality of sensors 12 on the center of the extraction area 300.

When the extraction area condition is met for the set first extraction area condition 320, the controller 20 may extract data in the extraction area 300 to generate the extraction data 400.

As a detailed example, referring to FIGS. 32A to 32C, when it is determined that the first extraction area 320 set in FIG. 32A meets the extraction area condition, as shown in FIG. 32B or 32C, the sensing data 200 included in the first extraction area 320 may be extracted to generate the extraction data 400. In this case, as the range (29 to 42) of the sensing values of the extraction data 400 includes the range (31 to 40) of the sensing values output by the plurality of sensors 12, the extraction data 400 may be smaller in data size than all the sensing data 200.

In an embodiment, when generating the extraction data 400, the controller 20 may generate the extraction data 400 to maintain sensing values included in the extraction data

300. For example, as shown in FIG. 32B, the extraction data 400 may be generated to maintain the existing sensing value range 29 to 42 of the first extraction area 320.

In another embodiment, when generating the extraction data 400, the controller 20 may change the sensing values 220 included in the extraction area 300 to predetermined sensing values to generate the extraction data 400. For example, as shown in FIG. 32C, the extraction data 400 may be generated such that the existing sensing value range 29 to 42 of the first extraction area 320 is changed to a predetermined sensing value range 1 to 14.

Meanwhile, when the extraction area condition of the first extraction area 320 is not met, the controller 20 may set a second extraction area 340.

Figure 35:
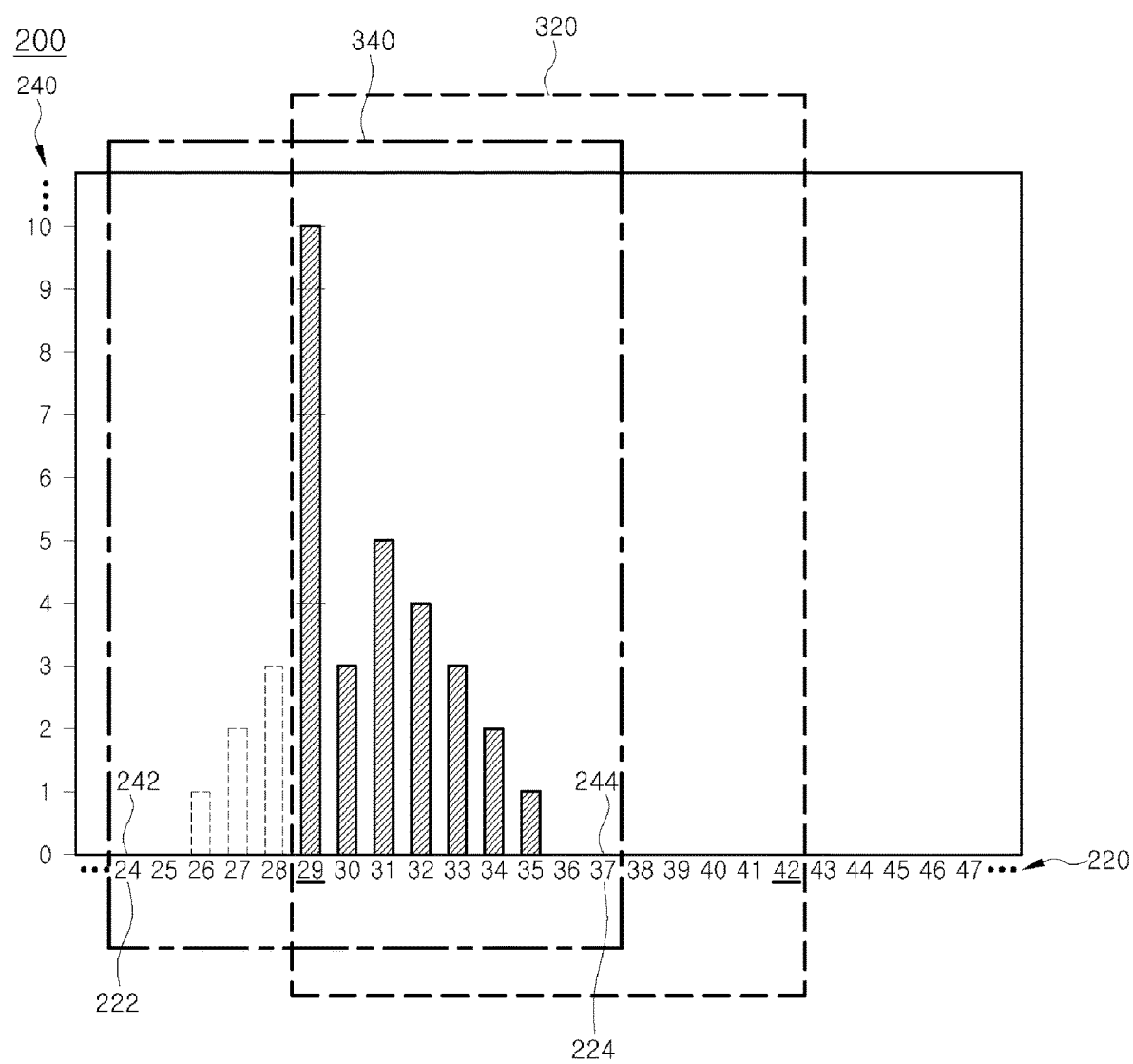
FIG. 35 is a drawing illustrating a setting of a second extraction area according to the present disclosure.

FIG. 35 is a drawing illustrating a setting of a second extraction area according to the present disclosure.

Referring to FIG. 35, in an embodiment, a second extraction area 340 may be set to be the same in size as the first extraction area 320 (i.e., to be the same in the number of included sensing values) and to be different in a range of the included sensing values from the first extraction area 320.

Furthermore, in an embodiment, a setting of the second extraction area 340 may be to first set the second extraction area 340 different from the first extraction area 320 and thus determine whether the set second extraction area 340 meets an extraction area condition.

As a detailed example, in case of FIG. 34, the first extraction area 320 which does not meet the extraction area condition may move to the left by 1 to set the second extraction area 340, it may be determined whether the second extraction area 340 meets the extraction area condition, and it may repeat until the condition is met, but not limited thereto.

In another embodiment, the setting of the second extraction area 340 may be to set the second extraction area 340 to meet the extraction area condition.

As a detailed example, when it is determined that the first extraction area 320, which is initially set, does not meet the extraction area condition, a sensing value range meeting the extraction area condition may be set to the second extraction area 340.

For example, like the above-mentioned embodiment, when the extraction area condition is 'that the difference between the smallest sensing value among the sensing values, each of which has the number information which is not 0 in the sensing data, and the first sensing value is equal to the difference between the largest sensing value and the second sensing value', as shown in FIG. 35, a sensing value range of 24 to 37 meeting the extraction area condition may be set to the second extraction area 340.

When the second extraction area 340 is set to meet the extraction area condition, a controller 20 may extract data in the second extraction area 340 to generate extraction data 400.

Meanwhile, like the example of FIG. 29B, when there are a plurality of sensors (colorlessness), each of which has a sensing value of 0 (does not output a sensing value), among a plurality of sensors 12, the handling of the sensing value which is 0 may become a problem in the above-mentioned extraction area condition. In detail, in this case, this is because a first sensing value may always be 0.

To address it, in an embodiment, when it is determined whether the set extraction area 300 meets the extraction area condition, number information 240, the sensing value 220 of which is 0, may be excluded (i.e., a first sensing value is not 0). When the extraction data 400 is generated for the range of sensing values except for 0 like the above-mentioned examples based on it, it may be determined that the other sensors except for sensors which output sensing values which are not 0 among the plurality of sensors 12 do not output sensing values (e.g., pressure is not applied).

In another embodiment, when it is determined whether the set extraction area 300 meets the extraction area condition, likewise, the number information 240, the sensing value 220 of which is 0, may be excluded. Upon generation of the extraction data 400, data with the sensing value of 0 may be extracted together as well as data in the extraction area 300 to generate the extraction data 400 to include it.

In an embodiment, a sensing device 100 may further include a communication unit 30 which transmits the generated extraction data 400 to a computer.

The communication unit 30 may be connected with the computer in a wired or wireless manner. For example, the communication unit 30 may communicate with the computer using, but not limited to, Bluetooth® communication, Bluetooth® low energy (BLE) communication, near field communication, WLAN (Wi-Fi) communication, Zigbee communication, infrared data association (IrDA) communication, Wi-Fi direct (WFD) communication, ultra wideband (UWB) communication, ANT+ communication, or a WIFI communication method.

Furthermore, in an embodiment, the computer may output the extraction data 400, transmitted in real time, in real time as shown in FIG. 29B.

For example, when a different color is matched for each sensing value such that the lowest sensing value among the plurality of sensing values 220 included in the extraction data 400 corresponds to a blue color and such that the highest sensing value corresponds to a red color and when it is displayed in colors matched to the sensing values 220 respectively output from the plurality of sensors 12, it is shown that the extraction data 400 display as shown in FIG. 29B includes the range of the sensing values 220 output by the plurality of sensors 12.

On the other hands, assuming that the extraction data 400 is generated as shown in FIG. 33, because the sensors 12, which output the sensing values 220 of 42 to 45 when outputting the extraction data 400, are output in the same color (red), there may be a problem in which it is unable to know a difference therebetween.

Furthermore, assuming that the extraction data 400 is generated as shown in FIG. 34, the sensors 12, which output the sensing values 220 of 26 to 29 when outputting the extraction data 400, may be output in the same color (blue).

Thus, to improve a data transfer rate, the communication unit 30 may transmit the extraction data obtained by extracting some of the sensing data 200 to the computer. To address the above-mentioned problem, the communication unit 30 may set the extraction area 300 to include the range of the sensing values 220 output by the plurality of sensors 12.

Figure 36A:
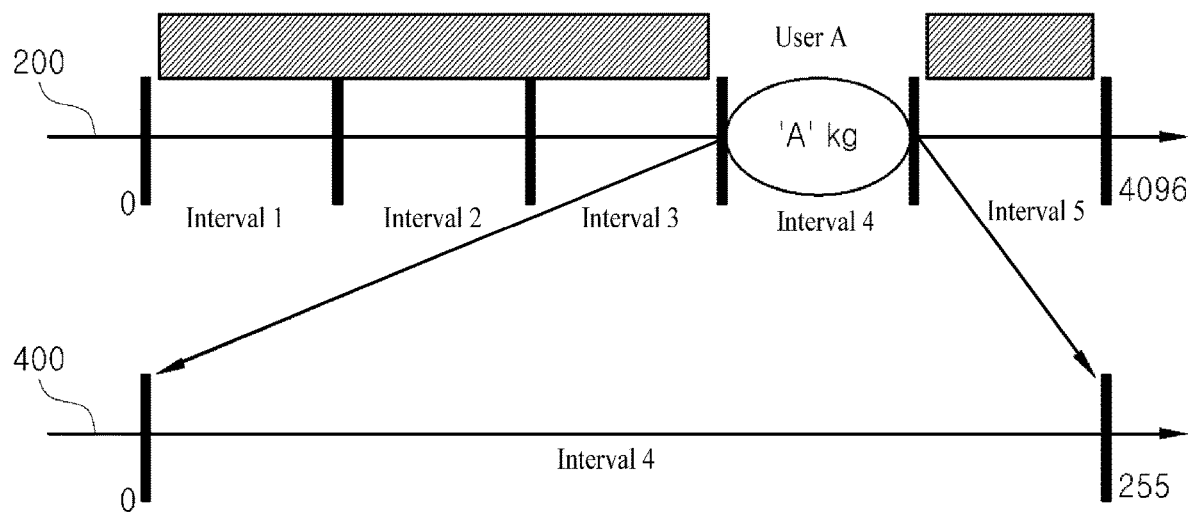
FIGS. 36A and 36B are drawings illustrating setting a different extraction area for each user and generating extraction data according to the present disclosure.
Figure 36B:
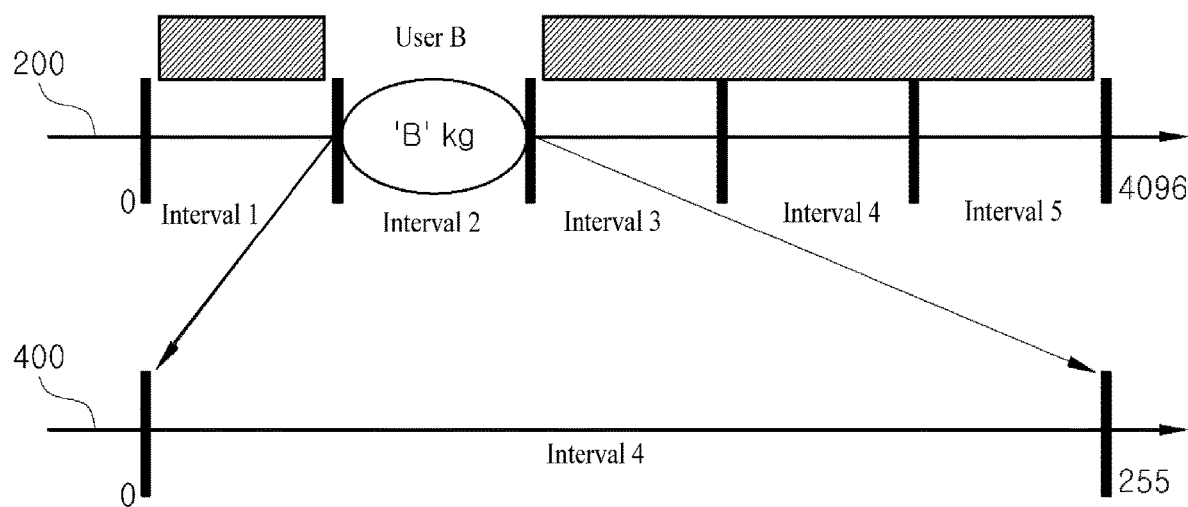

FIGS. 36A and 36B are drawings illustrating setting a different extraction area for each user and generating extraction data according to the present disclosure. The present disclosure will be described in detail with reference to FIGS. 29A to 29C and FIGS. 36A and 36B.

Giving an example of a pressure sensing device which measures and outputs plantar pressure of a user as shown in FIG. 29A, to move the center of mass of the user or measure balance, although users with different weights use pressure sensing devices, respectively, there is a need to output various colors of plantar pressure screens as shown in FIG. 29B for each user. That is, irrespective of a weight of the user who uses the pressure sensing device, there is a need to display an area on which relatively more weight is put in red for each user and display an area on which relatively less weight is put in blue.

Referring to FIGS. 36A and 36B, a sensing device according to the present disclosure may extract data of a specific interval where sensing values are distributed according to a weight of a specific user in the sensing value range of all sensing data 200 to generate extraction data 400. In detail, data of interval 4 may be extracted for user A and data of interval 2 may be extracted for user B to generate the extraction data 400.

Thereafter, as a different color is matched and output for each sensing value such that the lowest value among sensing values included in the extracted extraction data 400 corresponds to a blue color and such that the highest sensing value corresponds to a red color, various colors of plantar pressure screens may be output for each user. In detail, a plantar pressure screen may be output such that the lowest sensing value is matched to a blue color and the highest sensing value is matched to a red color in interval 4 upon use of user A and such that the lowest sensing value is matched to the blue color and the highest sensing value is matched to the red color in interval 2 upon use of user B. Thus, when the center of mass moves for each user irrespective of a weight of the user (e.g., when the user sits and stands), there is an effect capable of identifying movement of the center of mass through a change in color of the plantar pressure output screen.

In an embodiment, a sensing device 100 may further include a storage unit 40 which stores extraction area information about the measured user.

The storage unit 40 may store extraction area information generating the extraction data 400 for the user. When the sensing data 200 for the same user is additionally obtained, a controller 20 may generate the extraction data 400 based on the extraction area information stored in the storage unit 40.

In an embodiment, the extraction area condition may include information about the range of sensing values 330 included in an extraction area 300 set to meet an extraction area condition for a specific user.

As a detailed example, for a pressure sensing device shown in FIGS. 29A to 29C, a time when the sensing data 200 is obtained for the specific user is varied, it is common practice that the range of the sensing values 220 output by a plurality of sensors 12 is not considerably changed for a certain posture (e.g., a standing posture). Thus, information about the extraction area 300 set to meet the extraction area condition for the specific user may be stored. Thereafter, when the sensing data 200 for the same user is additionally obtained, as the extraction data 400 is generated based on the stored extraction area information without passing through a separate operation of setting the extraction area, processing of sensing data may be more efficiently performed.

To this end, the above-mentioned sensing pad 10 according to the present disclosure may obtain the sensing data 200 of the user in a reference environment.

As a detailed example, for the pressure sensing device shown in FIGS. 29A to 29C, the sensing data 200 may be obtained in a reference posture (e.g., a standing posture) using the corresponding pressure sensing device. Furthermore, to this end, the sensing device or a computer connected with the sensing device may output a notification for guiding the user to maintain the reference posture.

In another embodiment, when there is a request of the user or when the generated extraction data 400 does not meet the extraction area condition, it is possible to set the extraction area 300 or generate the extraction data 400 again.

Figure 37:
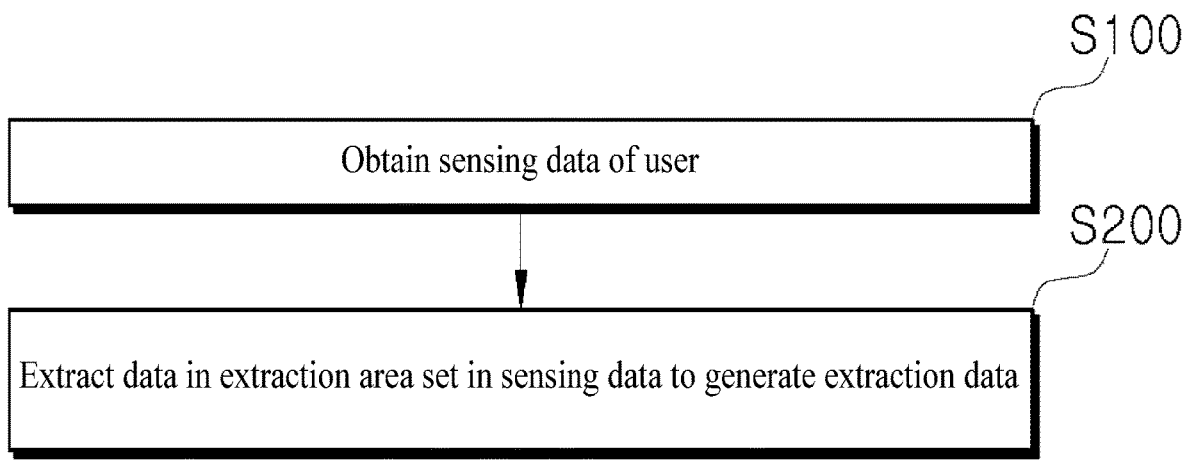
FIG. 37 is a flowchart of a method for processing sensing data according to the present disclosure.

FIG. 37 is a flowchart of a method for processing sensing data according to the present disclosure.

Referring to FIG. 37, the method for processing the sensing data according to the present disclosure may include obtaining (S100) sensing data 200 of a user and extracting (S200) data in an extraction area 300 set in the sensing data 200 to generate extraction data 400.

Operation S100 may be an operation of obtaining, by a sensing pad 10, the sensing data 200 of the user using a plurality of sensors 12.

Furthermore, in an embodiment, although not illustrated in the drawing, the method for processing the sensing data according to the present disclosure may further include removing, by a controller 20, a noise of the sensing data 200 prior to operation S200.

Operation S200 may be an operation of extracting, by the controller 20, the data in the extraction area 300 set in the sensing data 200 to generate the extraction data 400, based on the sensing data 200 received from the sensing pad 10.

Referring to FIG. 31, in an embodiment, operation S200 may include determining (S220) whether an extraction area condition of a first extraction area 320 set for the sensing data 200 is met, extracting (S260) data in the first extraction area 320 to generate the extraction data 400, when the condition is met, and setting (S240) a second extraction area 340, when the condition is not met.

That is, the controller 20 may determine whether the extraction area condition of the first extraction area 320 set for the sensing data 200 is met (S220). When the condition is met as a result of the determination, the controller 20 may extract the data in the first extraction area 320 to generate the extraction data (S260). When the condition is not met, the controller 20 may set the second extraction area 340 different from the first extraction area 320 (S240).

Figure 38:
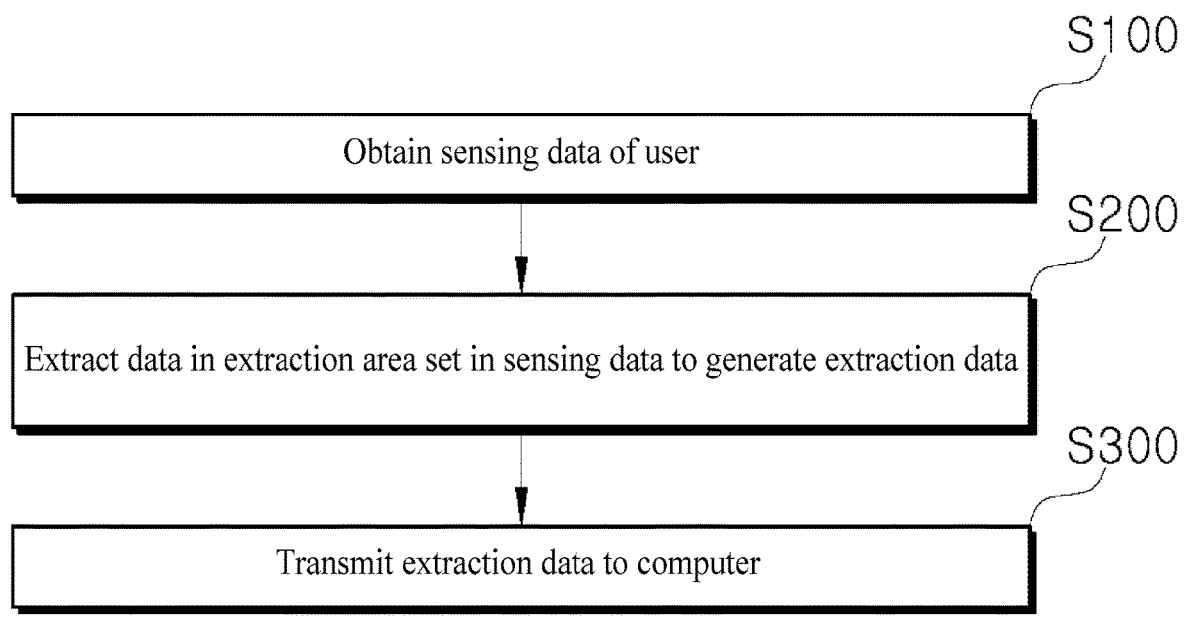
FIG. 38 is a flowchart of a method for processing sensing data, which further includes transmitting extraction data, according to the present disclosure.
Figure 39:
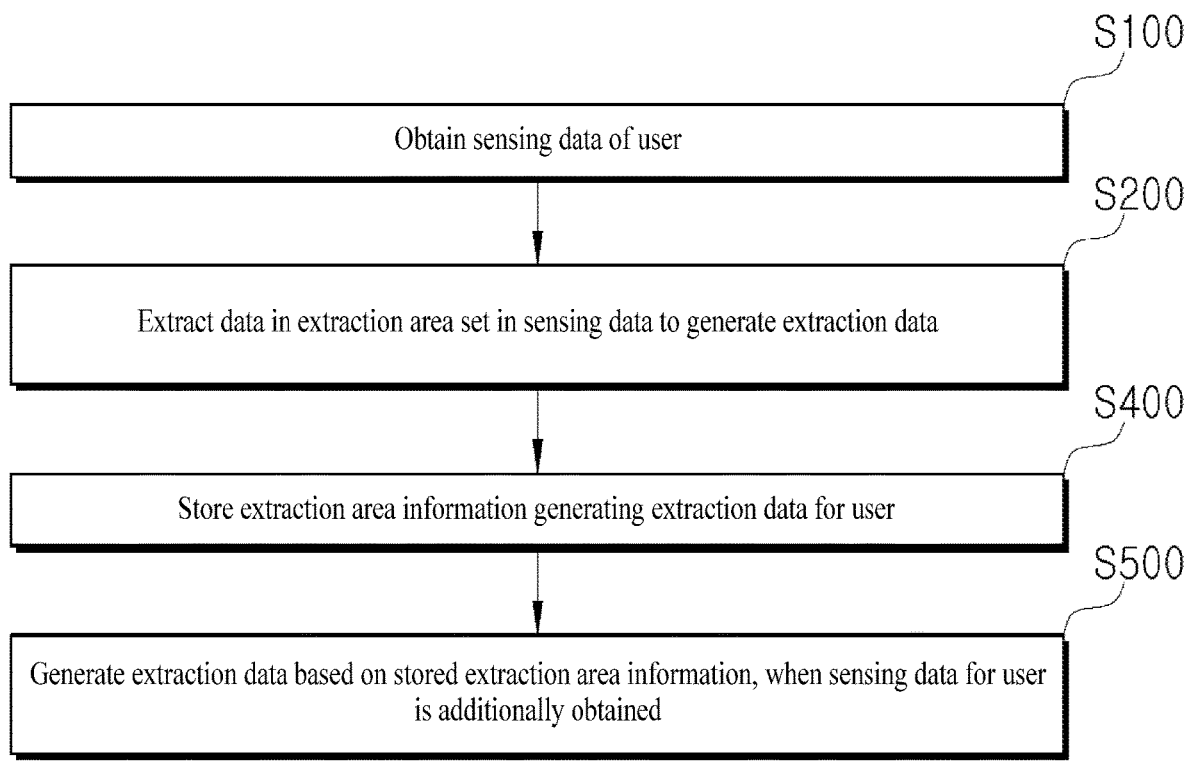
FIG. 39 is a flowchart of a method for processing sensing data, which further includes storing and calibrating extraction data, according to the present disclosure.

FIG. 38 is a flowchart of a method for processing sensing data, which further includes transmitting extraction data, according to the present disclosure. FIG. 39 is a flowchart of a method for processing sensing data, which further includes storing and calibrating extraction data, according to the present disclosure.

Referring to FIG. 38, the method for processing the sensing data according to the present disclosure may further include transmitting (S300), by a communication unit 30, extraction data 400 generated in operation S200 to a computer.

Referring to FIG. 39, the method for processing the sensing data according to the present disclosure may further include storing (S400) extraction area information generating extraction data 400 for a user and generating (S500) the extraction data 400 based on the stored extraction area information, when sensing data 200 for the same user is additionally obtained.

Operation S400 may be an operation of storing, by a storage unit 40, information about the extraction area 300 generating the extraction data 400 for the sensing data 200 of a specific user in operation S200.

When a sensing pad 10 additionally obtains the sensing data 200 for the same user as the extraction area information stored in storage unit 40 in operation S400, operation S500 may be to generate, by the controller 20, the extraction data 400 based on the extraction area information stored in the storage unit 40 without newly setting the extraction area 300 for the additionally added sensing data 200 and determining the extraction area condition.

Detailed contents of each operation are duplicated with the above-mentioned contents, they will be omitted.

Furthermore, the above-mentioned method for processing the sensing data according to the present disclosure may be combined with a computer which is hardware and may be stored in a medium to be implemented as a program (or application) to be executed.

For the computer to read the program and execute the methods implemented with the program, the program may include a code coded into a computer language such as C, C++, Java, or a machine language readable through a device interface of the computer by a processor (CPU) of the computer. Such a code may include a functional code associated with a function and the like defining functions necessary for executing the methods and may include a control code associated with an execution procedure necessary for the processor of the computer to execute the functions according to a procedure. Further, such a code may further include a code associated with memory reference about whether additional information or media necessary for the processor of the computer to execute the functions is referred at any location (address number) of an internal or external memory of the computer. Further, if it is necessary for the processor of the computer to communicate with any computer or server located in a remote place to execute the functions, the code may further include a communication related code about how communication is performed with any computer or server located in a remote place using a communication module of the computer and whether to transmit and receive any information or media upon communication.

The medium may refer to a device-readable medium which stores data on a semipermanent basis rather than a medium, such as a register, a cache, or a memory, which stores data during a short moment. The medium may refer to a device-readable medium which stores data on a semipermanent basis rather than a medium, such as a register, a cache, or a memory, which stores data during a short moment. In other words, the program may be stored in various storage media on various servers accessible by the computer or various storage media on the computer of the user. Further, the medium may be distributed to a computer system connected over a network and may store a computer-readable code on a distributed basis.

Operations of the method or algorithm described in connection with an embodiment of the present disclosure may be directly implemented in hardware, may be implemented with a software module executed by hardware, or may be implemented by a combination of the hardware and the software module. The software module may reside on a random access memory (RAM), a read only memory (ROM), an erasable programmable ROM (EPROM), an electrically erasable programmable ROM (EEPROM), a flash memory, a hard disc, a removable disc, a CD-ROM, or any type of computer-readable storage medium which is well known in the technical field to which the present disclosure pertains.

Hereinafter, a sensing device according to the present disclosure will be described in detail with reference to the accompanying drawings.

Figure 40:
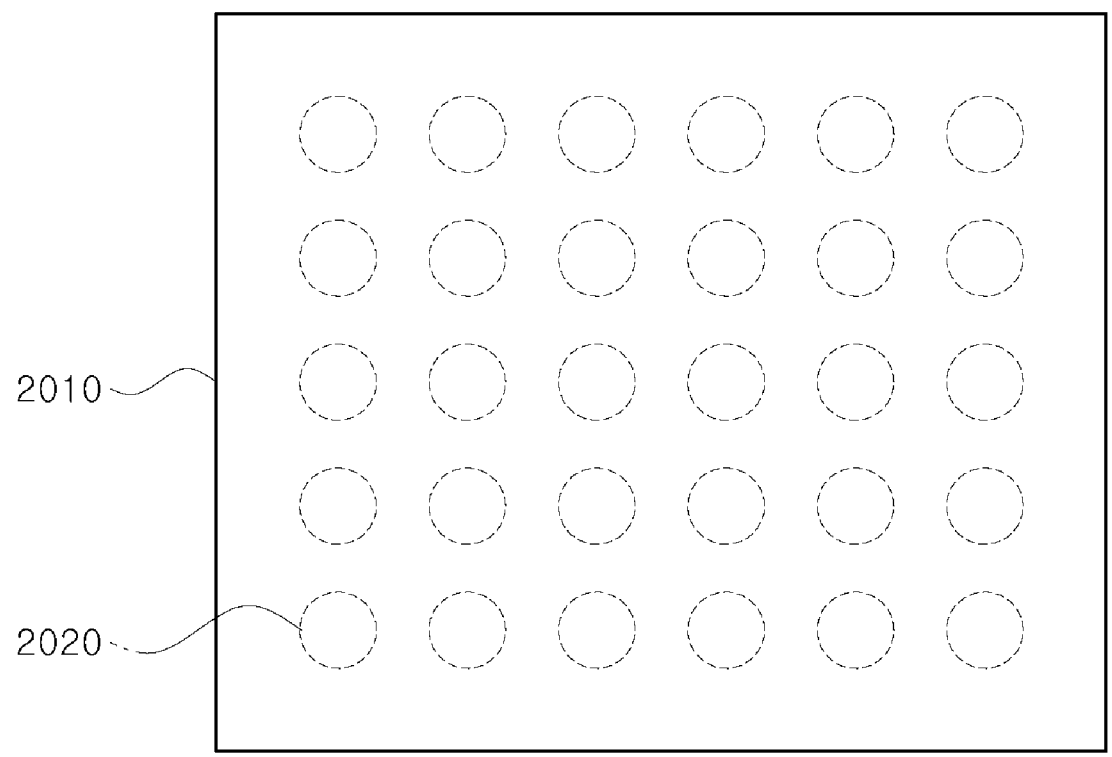
FIG. 40 is a block diagram illustrating a sensing device of a sensing device according to the present disclosure.
Figure 41:
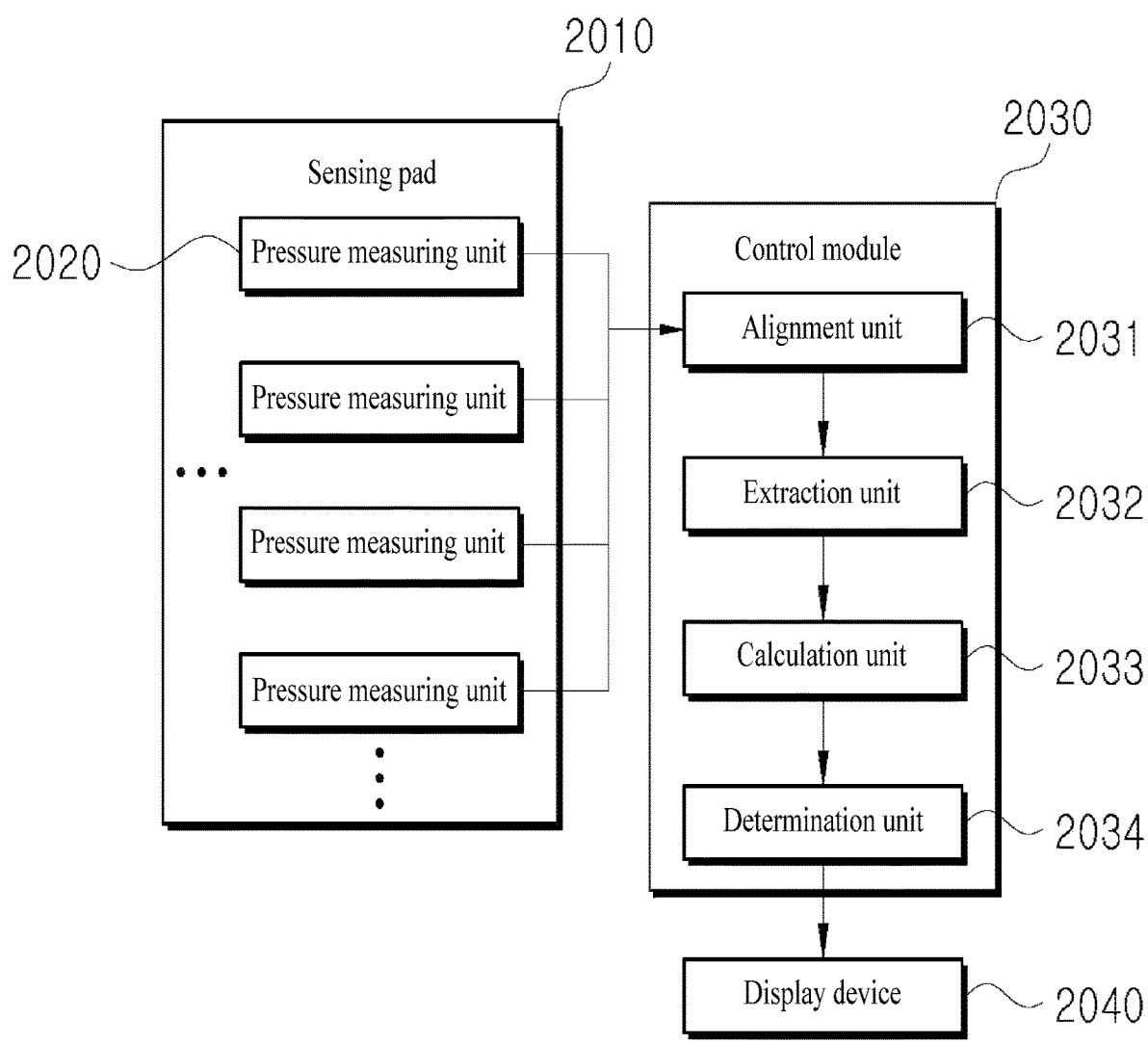
FIG. 41 is a block diagram illustrating a sensing device according to the present disclosure.

FIG. 40 is a block diagram illustrating a sensing module of a sensing device according to the present disclosure. FIG. 41 is a block diagram illustrating a sensing device according to the present disclosure.

As shown in FIGS. 40 and 41, the sensing device according to the present disclosure may include a sensing module, a control module 2030, and a display device 2040.

In the sensing device according to the present disclosure as a whole, when a load of both feet is applied to a sensing pad 2010 of the sensing module, a pressure measuring unit 2020 of the sensing module may measure plantar pressure by the load of both the feet applied to the sensing pad 2010 to generate plantar pressure data. The control module 2030 may align the plantar pressure data in a matrix and may filter target data in the plantar pressure data matrix, which is less than a unique reference value, as noise. The display device 2040 may display the plantar pressure data (or the plantar pressure data matrix), in which the filtering of the noise is completed, on a screen.

The sensing module may measure plantar pressure by a load of both feet and may deliver the measured plantar pressure to the control module 2030, which may include the sensing pad 2010 and the pressure measuring unit 2020.

The sensing pad 2010 may be placed by both feet, and a load of both the feet may be applied to the sensing pad 2010.

It is preferable that the sensing pad 2010 is formed of a material with good durability, such as chrome, rubber, acrylic, or tempered glass, to bear the load of both the feet (i.e., a load of the human body).

The plurality of pressure measuring units 2020 may be provided under the sensing pad 2010, and the load of both the feet applied to the sensing pad 2010 may be delivered to the plurality of pressure measuring units 2020. At this time, the load of both the feet applied to the sensing pad 2010 may be delivered to the plurality of pressure measuring units 2020 through a change (i.e., expansion or contraction) in the shape of the sensing pad 2010. Furthermore, a supporter (not shown) for supporting the sensing pad 2010 may be installed under the sensing pad 2010.

The sensing pad 2010 and the pressure measuring units 2020 may be implemented as a touch screen, and a description thereof will be given below.

The pressure measuring units 2020 may play a role in measuring plantar pressure by a load of both feet applied to the sensing pad 2010 to generate plantar pressure data.

Pressure sensors, piezoelectric sensors, force sensors, and the like may be used as the pressure measuring units 2020, but it is merely illustrative, but not particularly limited thereto.

The pressure measuring units 2020 may be provided under the sensing pad 2010. For example, the pressure measuring units 2020 may be fixed under the sensing pad 2010, and sockets (not shown) for fixing the pressure measuring units 2020 may be formed under the sensing pad 2010. Furthermore, the pressure measuring units 2020 may be spaced apart from each other at a certain distance under the sensing pad 2010.

The pressure measuring units 2020 may be arranged in a matrix (i.e., in the form of a matrix). In detail, the pressure measuring units 2020 may be arranged in a rectangular matrix or a square matrix. Such pressure measuring units 2020 may be assigned unique numbers based on locations on the matrix. For example, the pressure measuring unit 2020 located in a first column and a first row with respect to the matrix on which the pressure measuring units 2020 are arranged may be assigned unique number 1-1. Furthermore, the pressure measuring unit 2020 located in a second column and a second row with respect to the matrix on which the pressure measuring units 2020 are arranged may be assigned unique number 2-2. Coordinates of each pressure measuring unit 2020 may be accurately identified through such a unique number.

The control module 2030 may play a role in determining whether there is noise among plantar pressure data measured by the pressure measuring units 2020 and filtering the noise.

A computer or a smartphone may be used as the control module 2030, and it is merely illustratively, but not particularly limited thereto.

The control module 2030 may include an alignment unit 2031, an extraction unit 2032, a calculation unit 2033, and a determination unit 2034. Such an alignment unit 2031, an extraction unit 2032, a calculation unit 2033, and a determination unit 2034 may be an application or a program installed in the control module 2030.

The alignment unit 2031 may align plantar pressure data obtained from the pressure measuring units 2020 in a plantar pressure data matrix depending on coordinates of the pressure measuring units 2020. As an example, the alignment unit 2031 may align plantar pressure data measured by the pressure measuring unit 2020 located in a first column and a first row of the sensing pad 2010 in a first column and a first row of a plantar pressure data matrix, on the basis of coordinates of the pressure measuring units 2020 provided in the sensing pad 2010. Plantar pressure data measured by the pressure measuring unit 2020 located in a second column and a second row of the sensing pad 2010 may be aligned in a second column and a second row of the plantar pressure data matrix.

The extraction unit 2032 may extract first maximum data having a maximum value in n rows and second maximum data having a maximum value in m columns, on the basis of target data of the n rows and the m columns in the plantar pressure data matrix.

The calculation unit 2033 may determine one of the first maximum data and the second maximum data as reference data and may calculate a unique reference value based on the reference data. Herein, the reference data may be a smaller value between the first maximum data and the second maximum data, and the unique reference value may be a value obtained by assigning a weight to reference data and may be used as a value for determining whether there is a noise of target data. Herein, assigning the weight may refer to multiplying a specific numerical value by the reference data.

Such a weight may vary with properties of a material forming the sensing pad 2010 and may vary with, for example, surface resistivity of the material forming the sensing pad 2010.

As an example, when the sensing pad 2010 is formed of a material with large surface resistivity, a strain of the sensing pad 2010 by a load of both feet may be small. Due to this, because sensitivity of the pressure measuring units 2020 which measure pressure through deformation of the sensing pad 2010 is small, the calculation unit 2033 may assign a weight as a value greater than a predetermined value.

As another example, when the sensing pad 2010 is formed of a material with relatively small surface resistivity, a strain of the sensing pad 2010 by the load of both the feet may be relatively large. Due to this, because sensitivity of the pressure measuring units 2020 which measure pressure through deformation of the sensing pad 2010 is relatively large, the calculation unit 2033 may assign a weight as a value less than the predetermined value.

As another example, when the sensing pad 2010 is formed of a material of surface resistivity of 50,000 Ohms/sq or less, a weight assigned by the calculation unit 2033 may be 0.5 to 0.7. Herein, when the weight is less than 0.5, as a unique reference value, which is a noise determination condition of target data, is considerably reduced, a number where the determination unit 2034 determines noise among the target data may be significantly reduced and little filtering of noise may be performed. When the weight assigned to reference data by the calculation unit 2033 is greater than 0.7, as the unique reference value, which is the noise determination condition of the target data, is considerably increased, a number where the determination unit 2034 determines noise among the target data may be significantly increased and a thing other than noise may be filtered. Therefore, when the sensing pad 2010 is formed of a material of surface resistivity of 50,000 Ohms/sq or less, it is preferable that the weight assigned by the calculation unit 2033 is limited to the above-mentioned numerical values.

The determination unit 2034 may determine whether the target data is noise based on the unique reference value.

As an example, when a condition where the target data is less than the unique reference value is met, the determination unit 2034 may determine the target data as noise and may filter the noise. At this time, the filtering may be processing the target data as 0.

Meanwhile, as the larger the weight assigned to the reference data by the control module 2030, the larger the unique reference value which is the noise determination condition of the target data, a number where the control module 2030 determines noise among target data may be increased. On the other hand, as the smaller the weight assigned to the reference data by the control module 2030, the smaller the unique reference value which is the noise determination condition of the target data, a number where the control module 2030 determines noise among the target data may be reduced.

The display device 2040 may visually display the plantar pressure data matrix, in which the filtering of the noise is completed by the determination unit 2034, on a screen. As the screen is partitioned into areas corresponding to the plantar pressure data matrix, such a display device 2040 may display a color corresponding to a value of unit data for each region of the screen.

Figure 42:
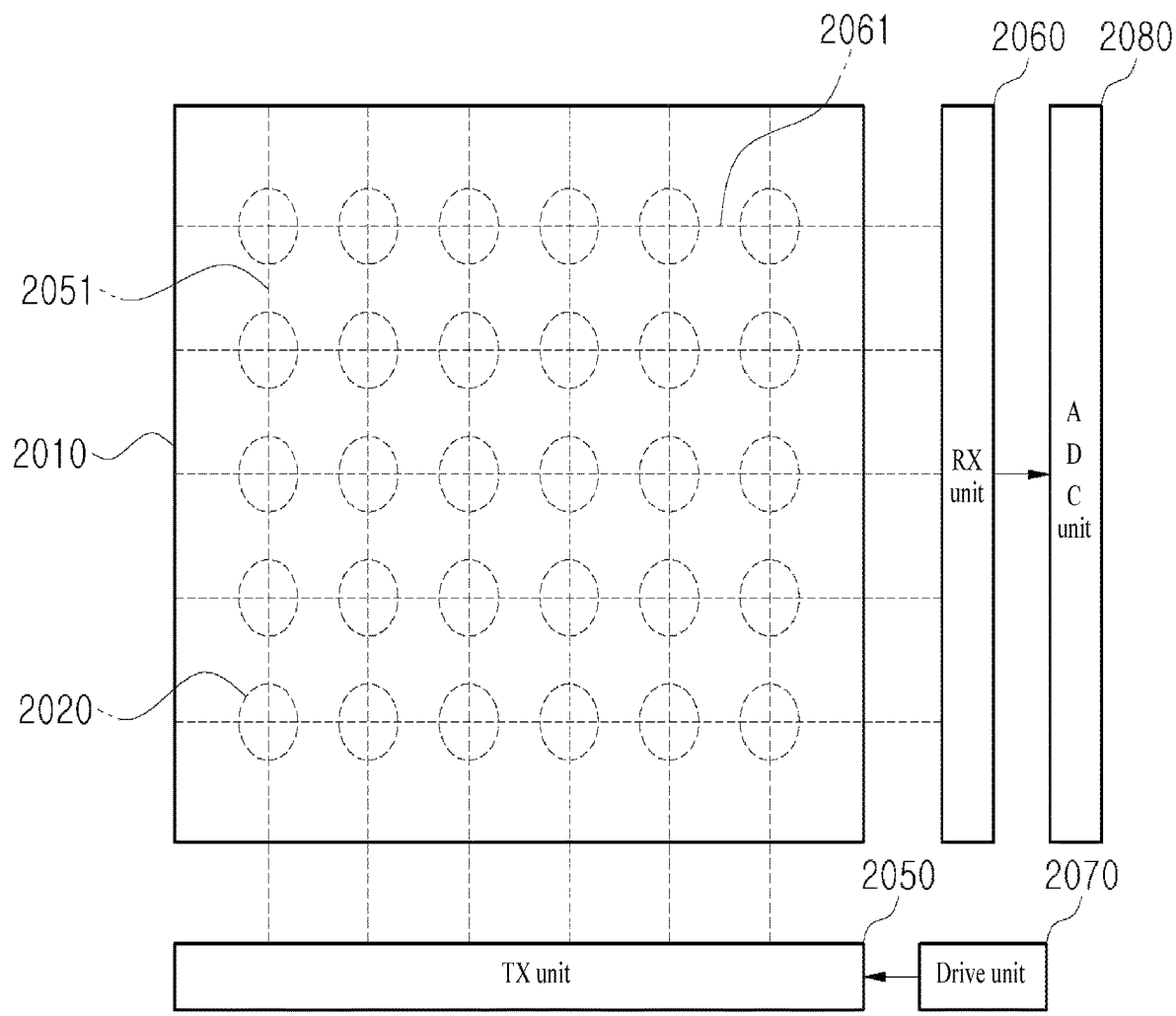
FIG. 42 is a drawing schematically illustrating an example where a sensing device of a sensing device is implemented as a touch screen according to the present disclosure.

FIG. 42 is a drawing schematically illustrating an example where a sensing module of a sensing device is implemented as a touch screen according to the present disclosure.

As shown in FIG. 42, a sensing pad 2010 and pressure measuring units 2020 of a sensing module of the sensing device according to the present disclosure may be implemented as a touch screen. To this end, a TX unit 2050, an RX unit 2060, a drive unit 2070, and an ADC unit 2080 may be further included.

The TX unit 2050 may have a plurality of TX lines 2051 (i.e., transmit lines) arranged in one between a column direction and a row direction.

The RX unit 2060 may have a plurality of RX lines 2061 (i.e., receive lines) arranged in the other between the column direction and the row direction.

A pressure measuring unit 2020 may be electrically connected to a crossing portion of the TX line 2051 and the RX line 2061.

The drive unit 2070 may provide a drive pulse to the TX line 2051 in response to a setup signal of the control module 2030.

The ADC unit 2080 may convert plantar pressure data of an analog state, which is measured by the pressure measuring unit 2020 and is received through the RX line 2061, into plantar pressure data of a digital state to deliver the plantar pressure data of the digital state to a control module 2030.

Hereinafter, a method for processing sensing data according to the present disclosure will be described in detail with reference to the accompanying drawings.

Figure 43:
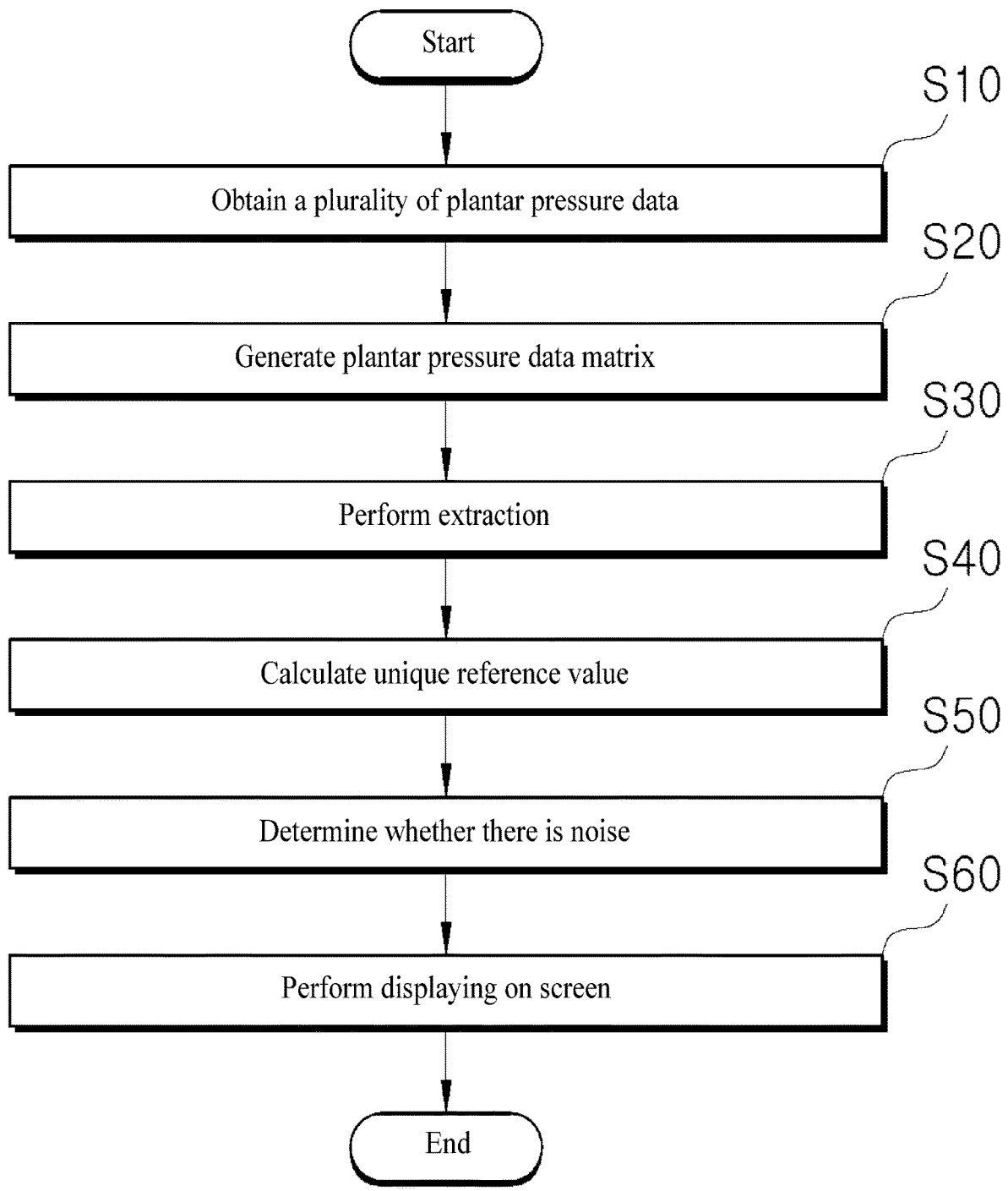
FIG. 43 is a flowchart illustrating a method for processing sensing data according to the present disclosure.

FIG. 43 is a flowchart illustrating a method for processing sensing data according to the present disclosure.

As shown in FIG. 43, the method for processing the sensing data according to the present disclosure may include obtaining (S10) a plurality of plantar pressure data, generating (S20) a plantar pressure data matrix, performing (S30) extraction, calculating (S40) a unique reference value, determining (S50) whether there is noise, and performing (S60) displaying on a screen.

In the obtaining (S10) the plurality of plantar pressure data, a control module may obtain the plurality of plantar pressure data from a plurality of pressure measuring units provided in a matrix on a sensing pad to which a load of both feet is applied.

Herein, both the feet may be put on the sensing pad, and the sensing pad may be changed in shape (i.e., expanded or contracted) by the load of both the feet. Furthermore, the plurality of pressure measuring units may be provided under the sensing pad, and the pressure measuring units may measure the load of both the feet applied to the sensing pad and may transmit the measured load to a control module. Furthermore, the control module may be, but is not particularly limited to, a computer or a smartphone.

In the generating (S20) of the plantar pressure data matrix, the control module may generate the plantar pressure data matrix in which the plantar pressure data measured by the pressure measuring units are aligned according coordinates of the pressure measuring units.

As an example, in the generating (S20) of the plantar pressure data matrix, plantar pressure data measured by the pressure measuring unit located in a first column and a first row of the sensing pad with respect to coordinates of the pressure measuring units provided on the sensing pad may be aligned in a first column and the first row of the plantar pressure data matrix. Furthermore, plantar pressure data measured by the pressure measuring unit 2020 located in a second column and a second row of the sensing pad may be aligned in a second column and a second row of the plantar pressure data matrix.

In the performing (S30) of the extraction, the control module may extract first maximum data having a maximum value in n rows and second maximum data having a maximum value in m columns, on the basis of target data of the n rows and the m columns in the plantar pressure data matrix.

In the calculating (S40) of the unique reference value, the control module may determine one of the first maximum data and the second maximum data as reference data and may calculate a unique reference value based on the reference data.

Herein, the reference data may be a smaller value between the first maximum data and the second maximum data, and the unique reference value may be a value obtained by assigning a weight to reference data and may be used as a value for determining whether target data is noise. Herein, assigning the weight may refer to multiplying a specific numerical value by the reference data. For example, the weight in the present embodiment may be 0.5 to 0.7.

In the determining (S50) of whether there is noise, the control module may determine whether the target data is noise based on the unique reference value.

As an example, in the determining (S50) of whether there is noise, the control module may determine the target data as noise and may filter the noise, when a condition where the target data is less than a unique reference value is met. Herein, the filtering may be processing the target data as 0.

In addition, a condition where target data in the plantar pressure data matrix is less than the unique reference value may be indicated as Equation 1 below.

$$Val[n][m] < A*Min[MaxY[n], MaxX[m]] \qquad \text{[Equation 1]}$$

Herein, Val[n] [m] denotes the target data of n rows and m columns in the plantar pressure data matrix, A*Min[MaxY[n], MaxX[m]] denotes the unique reference value of the target data of n rows and m columns in the plantar pressure data matrix, A denotes the weight, MaxY[n] denotes the maximum value of n rows in the plantar pressure data matrix, MaxX[m] denotes the maximum value of m columns in the plantar pressure data matrix, and Min[MaxY[n], MaxX[m]] denotes a smaller value between MaxY[n] and MaxX[m].

In the performing (S60) of the displaying on the screen, the plantar pressure data matrix, in which the filtering of the noise is completed, may be displayed on a screen of the display device.

Herein, a monitor, a smartphone, a TV, or the like may be used as the display device. Furthermore, as the screen is partitioned into areas corresponding to the plantar pressure data matrix, the display device may display a color corresponding to a value of unit data for each area of the screen.

Hereinafter, a description will be given in detail of the performing (S30) of the extraction, the calculating (S40) of the unique reference value, and the determining (S50) of whether there is noise, with reference to Table 1 which is an example of the plantar pressure data matrix.

TABLE 1

|  | First row | Second row | Third row | Fourth row | Fifth row |
| --- | --- | --- | --- | --- | --- |
| First column | 10 | 0 | 0 | 19 | 0 |
| Second column | 29 | 19 | 2 | 34 | 24 |
| Third column | 23 | 7 | 4 | 32 | 12 |
| Fourth column | 12 | 8 | 0 | 30 | 0 |

As an example, when target data in the plantar pressure data matrix is in a second row and a fourth column of Table 1, in the performing (S30) of the extraction, the control module may extract 19 having the maximum value in a second row of Table 1 as first maximum data on the basis of the target data of the second row and the fourth column of Table 1, 10, and may extract 30 having the maximum value in a fourth column of Table 1 as second maximum data. Thereafter, in the calculating (S40) of the unique reference value, the control module may determine a smaller value, 19, between the first maximum data, 19, and the second maximum data, 30, as reference data and may assign a weight to the reference data, 19, to calculate the unique reference value. At this time, assuming that the weight is 0.6, the unique reference value may be 11.4 obtained by multiplying the weight, 0.6, by the reference data, 19.

Thereafter, in the determining (S50) of whether there is the noise, the control module may identify that a condition where the target data of the second row and the fourth column of Table 1, 10, is less than the unique reference value, 11.4, is met and may determine the target data of the second row and the fourth column, 10, as noise to process the target data as 0.

As another example, in the performing (S30) of the extraction, when target data in the plantar pressure data matrix is in a first row and a third column, the control module may extract 29 having the maximum value in a first row of Table 1 as first maximum data and may extract 32 having the maximum value in a fourth column of Table 1 as second maximum data, with respect to the target data of the first row and the third column, 23.

Thereafter, in the calculating (S40) of the unique reference value, the control module may determine a smaller value, 29, between the first maximum data, 29, and the second maximum data, 32, as reference data and may assign a weight, 7, to the reference data, 29, to calculate the unique reference value. At this time, assuming that the weight is 0.6, the unique reference value may be 17.4 obtained by multiplying the weight, 0.6, by the reference data, 29.

Thereafter, in the determining (S50) of whether there is the noise, the control module may identify that a condition where the target data of a first row and a third column of Table 1, 23, is less than the unique reference value, 17.4, is not met and may determine that the target data of the first row and the third column, 23, is not noise to maintain the value.

Meanwhile, as the larger the weight assigned to the reference data by the control module, the larger the unique reference value which is the noise determination condition of the target data, a number where the control module determines noise among the target data may be increased. On the other hand, as the smaller the weight assigned to the reference data by the control module, the smaller the unique reference value which is the noise determination condition of the target data, a number where the control module determines noise among the target data may be reduced.

Herein, when the weight assigned to the reference data by the control module in the present embodiment is less than 0.5, as the unique reference value which is the noise determination condition of the target data is considerably reduced, a number where the determination unit determines noise among the target data may be significantly reduced and little filtering of noise may be performed.

When the weight assigned to reference data by the control module in the present embodiment is greater than 0.7, as the unique reference value which is the noise determination condition of the target data is considerably increased, a number where the determination unit determines noise among the target data may be significantly increased and a thing other than noise may be filtered.

Thus, it is preferable that the weight assigned to the reference data by the control module is 0.5 to 0.7.

Figure 44A:
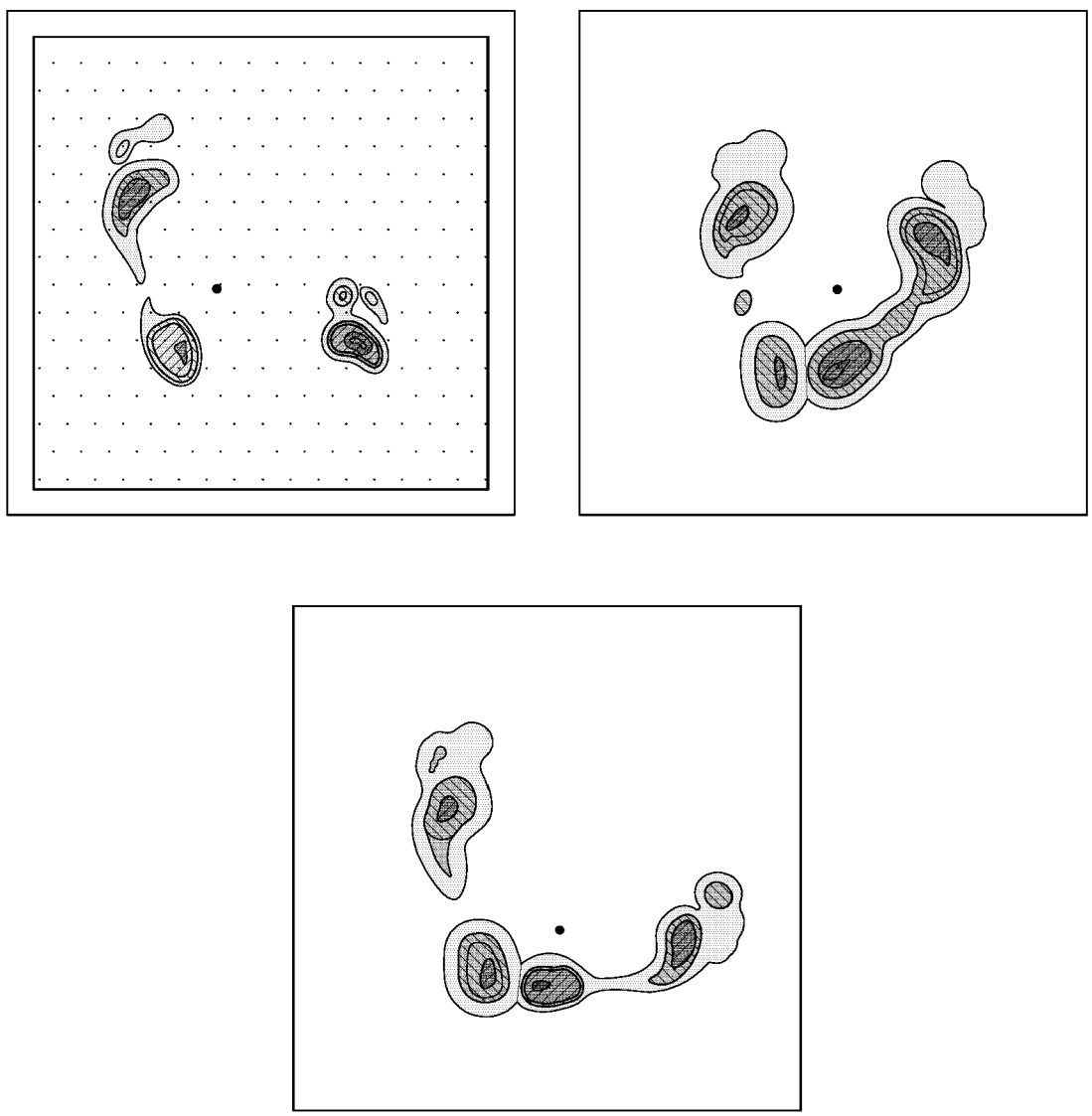
FIG. 44A is a screen of a display device indicating a result of measuring plantar pressure by a method for processing sensing data according to the present disclosure.
Figure 44B:
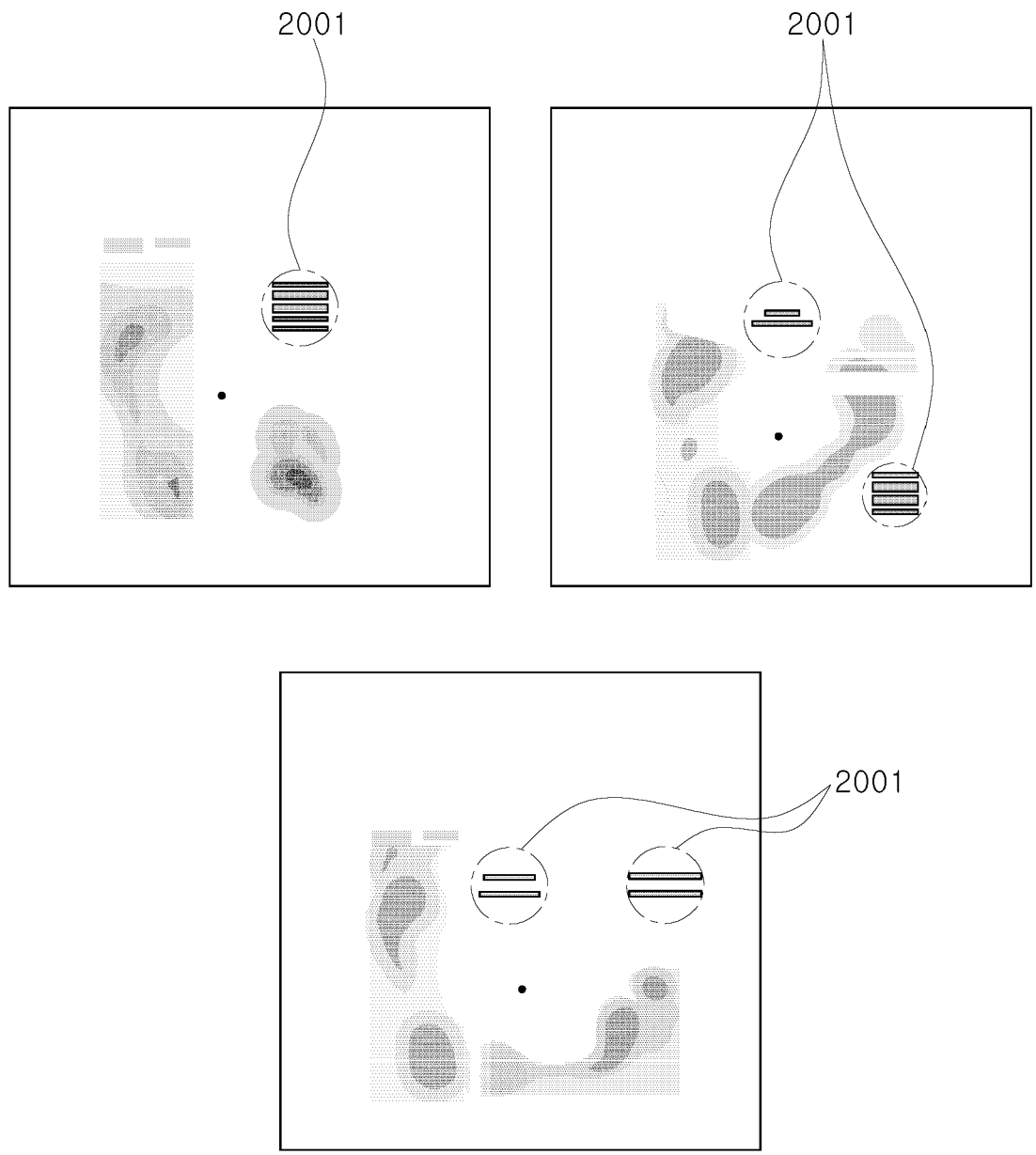
FIG. 44B is a screen of a display device indicating a result of measuring plantar pressure by a conventional method for processing sensing data.

FIG. 44A is a screen of a display device indicating a result of measuring plantar pressure by a method for processing sensing data according to the present disclosure. FIG. 44B is a screen of a display device indicating a result of measuring plantar pressure by a conventional method for processing sensing data.

As shown in FIG. 44A, in the method for processing the sensing data according to the present disclosure, it may be verified that a control module filters noise 2001 included in plantar pressure data measured by pressure measuring units to improve accuracy of the plantar pressure data.

On the other hand, as shown in FIG. 44B, in the conventional method for processing the sensing data (i.e., a method for not filtering noise included in plantar pressure data), as noise 2001 included in plantar pressure data measured by pressure sensors is maintained, it may be verified that accuracy of the plantar pressure data is degraded.

Meanwhile, the reason why the noise 2001 is included in the plantar pressure data measured by the pressure measuring units is because, as both feet applying a load to a sensing pad apply the load to three vertices of a rectangle of the sensing pad, when there is a portion where one vertex of the rectangle of the sensing pad is relatively weakly pressed, the portion is measured as noise.

Meanwhile, the method for processing the sensing data according to the present disclosure may be combined with a computer which is hardware and may be stored in a medium to be implemented as a program (or application) to be executed.

For the computer to read the program and execute the methods implemented with the program, the program may include a code coded into a computer language such as C, C++, Java, or a machine language readable through a device interface of the computer by a processor (CPU) of the computer. Such a code may include a functional code associated with a function and the like defining functions necessary for executing the methods and may include a control code associated with an execution procedure necessary for the processor of the computer to execute the functions according to a procedure. Further, such a code may further include a code associated with memory reference about whether additional information or media necessary for the processor of the computer to execute the functions is referred at any location (address number) of an internal or external memory of the computer. Further, if it is necessary for the processor of the computer to communicate with any computer or server located in a remote place to execute the functions, the code may further include a communication related code about how communication is performed with any computer or server located in a remote place using a communication module of the computer and whether to transmit and receive any information or media upon communication.

The medium may refer to a device-readable medium which stores data on a semipermanent basis rather than a medium, such as a register, a cache, or a memory, which stores data during a short moment. The medium may refer to a device-readable medium which stores data on a semipermanent basis rather than a medium, such as a register, a cache, or a memory, which stores data during a short moment. In other words, the program may be stored in various storage media on various servers accessible by the computer or various storage media on the computer of the user. Further, the medium may be distributed to a computer system connected over a network and may store a computer-readable code on a distributed basis.

Operations of the method or algorithm described in connection with an embodiment of the present disclosure may be directly implemented in hardware, may be implemented with a software module executed by hardware, or may be implemented by a combination of the hardware and the software module. The software module may reside on a random access memory (RAM), a read only memory (ROM), an erasable programmable ROM (EPROM), an electrically erasable programmable ROM (EEPROM), a flash memory, a hard disc, a removable disc, a CD-ROM, or any type of computer-readable storage medium which is well known in the technical field to which the present disclosure pertains.

According to the sensing device according to the present disclosure, portability of the sensing device may be improved and the user may perform training and assessment using the sensing device in various environments.

Furthermore, according to the sensing device according to the present disclosure, as a load applied to the sensing pad is concentrated on a sensor, a more accurate balance training and assessment result may be provided to the user.

Furthermore, according to the sensing device according to the present disclosure, an initial location for balance training and assessment may be simply guided to users of various groups, each of which has a different physical feature.

Furthermore, according to the sensing device and the method for processing the sensing data according to the present disclosure, some of all sensing data are extracted and transmitted to improve a data transfer rate. As data is extracted and transmitted with regard to the range of data sensed for each user, damage of data necessary for output or analysis may be reduced to improve reliability of sensing data.

Furthermore, according to the sensing device and the method for processing the sensing data according to the present disclosure, as the range of extracting sensing data for a specific user is stored, processing of the sensing data may be more efficiently performed.

Furthermore, according to the sensing device and the method for processing the sensing data according to the present disclosure, the control module may filter noise included in plantar pressure data measured by pressure measuring units, thus improving accuracy of the plantar pressure data.

The effects of the present disclosure are not limited to the above-described effects and other effects which are not described herein will become apparent to those skilled in the art from the following description.

While the present disclosure has been described with reference to embodiments, it will be apparent to those skilled in the art that various changes and modifications may be made without departing from the spirit and scope of the present disclosure. Therefore, it should be understood that the above embodiments are not limiting, but illustrative.

What is claimed is:

1. A sensing device, comprising:
   a sensing pad that is a touch screen; and
   a control module,
   wherein the sensing pad comprises:
      a plurality of pressure measuring units arranged in a matrix and configured to measure pressure applied by loads of both feet;
      a plurality of transmission lines arranged in a column direction of the matrix and configured to provide a drive pulse to the plurality of pressure measuring units, in response to a setup signal from the control module; and
      a plurality of reception lines arranged in a row direction of the matrix and configured to receive a plurality of plantar pressure data having an analog state, from the plurality of pressure measuring units,
      wherein each pressure measuring unit of the plurality of pressure measuring units is electrically connected to a crossing point of one transmission line of the plurality of transmission lines and one reception line of the plurality of reception lines, and
   wherein the control module is configured to:
      receive the plurality of plantar pressure data having a digital state, converted from the plurality of plantar pressure data having the analog state;
      generate a plantar pressure data matrix obtained by aligning the plantar pressure data depending on coordinates of the pressure measuring units, each of which is connected to the crossing point of one transmission line of the plurality of transmission lines and one reception line of the plurality of reception lines;
      obtain first maximum data having a maximum value in n rows and second maximum data having a maximum value in m columns, on the basis of target data of the n rows and the m columns in the plantar pressure data matrix;
      determine one of the first maximum data and the second maximum data as reference data and calculate a unique reference value based on the reference data; and
      determine whether the target data is noise based on the unique reference value.

2. The sensing device of claim 1, wherein the reference data is a smaller value between the first maximum data and the second maximum data.

3. The sensing device of claim 1, wherein the unique reference value is a value obtained by assigning a weight to the reference data.

4. The sensing device of claim 3, wherein the weight is 0.5 to 0.7.

5. The sensing device of claim 3, wherein, the sensing pad is formed of a first material that has a first surface resistivity that is greater than a predetermined surface resistivity value, such that the weight has a first weight value that is greater than a predetermined weight value, or
   wherein, the sensing pad is formed of a second material that has a second surface resistivity that is equal to or smaller than the predetermined surface resistivity value, such that the weight has a second weight value that is less than the predetermined weight value.

6. The sensing device of claim 1, further comprising:
   a display device configured to display the plantar pressure data matrix, in which filtering of the noise is completed in the control module, on a screen.

7. The sensing device of claim 1, further comprising:
   a display device configured to display a pressure map of the both feet, in which the noise is filtered.

8. A method for processing sensing data, performed by a sensing device having a sensing pad that is a touch screen, and a control module, the method comprising:
   measuring pressure applied by loads of both feet, by a plurality of pressure measuring units of the sensing pad, arranged in a matrix;
   providing a drive pulse to the plurality of pressure measuring units, in response to a setup signal from the control module, by a plurality of transmission lines arranged in a column direction of the matrix;
   receiving a plurality of plantar pressure data having an analog state, from the plurality of pressure measuring units, by a plurality of reception lines arranged in a row direction of the matrix,
   wherein each pressure measuring unit of the plurality of pressure measuring units is electrically connected to a crossing point of one transmission line of the plurality of transmission lines and one reception line of the plurality of reception lines;
   receiving, by the control module, the plurality of plantar pressure data having a digital state, converted from the plurality of plantar pressure data having the analog state;
   generating, by the control module, a plantar pressure data matrix obtained by aligning the plantar pressure data depending on coordinates of the pressure measuring units, each of which is connected to the crossing point of one transmission line of the plurality of transmission lines and one reception line of the plurality of reception lines;

obtaining, by the control module, first maximum data having a maximum value in n rows and second maximum data having a maximum value in m columns, on the basis of target data of the n rows and the m columns in the plantar pressure data matrix;

determining, by the control module, one of the first maximum data and the second maximum data as reference data and calculating, by the control module, a unique reference value based on the reference data; and determining, by the control module, whether the target data is noise based on the unique reference value.

9. The method of claim 8, wherein the reference data is a smaller value between the first maximum data and the second maximum data.

10. The method of claim 8, wherein the unique reference value is a value obtained by assigning a weight to the reference data.

11. The method of claim 10, wherein the weight is 0.5 to 0.7.

12. The method of claim 10, wherein, the sensing pad is formed of a first material that has a first surface resistivity that is greater than a predetermined surface resistivity value, such that the weight has a first weight value that is greater than a predetermined weight value, or wherein, the sensing pad is formed of a second material that has a second surface resistivity that is equal to or smaller than the predetermined surface resistivity value, such that the weight has a second weight value that is less than the predetermined weight value.

13. The method of claim 8, wherein the determining of whether the target data is the noise includes:

determining, by the control module, the target data as the noise and filtering, by the control module, the noise, when a condition where the target data is less than the unique reference value is met.

14. The method of claim 13, further comprising:

displaying the plantar pressure data matrix, in which filtering of the noise is completed in the control module, on a screen of a display device.

15. The method of claim 13, further comprising:

displaying a pressure map of the both feet, in which the noise is filtered, on a screen of a display device.

* * * * *